United States Patent
King et al.

(10) Patent No.: US 6,759,509 B1
(45) Date of Patent: *Jul. 6, 2004

(54) BRANCHED PEPTIDE LINKERS

(75) Inventors: Dalton King, Hamden, CT (US); Raymond A. Firestone, Stanford, CT (US); Gene M. Dubowchik, Middlefield, CT (US)

(73) Assignee: Bristol-Myers Squibb Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,348

(22) Filed: Oct. 31, 1997

Related U.S. Application Data

(60) Provisional application No. 60/030,367, filed on Nov. 5, 1996.

(51) Int. Cl.[7] .............................................. C07K 5/10
(52) U.S. Cl. ............................ 530/330; 514/2; 514/18; 514/19; 530/331; 530/399; 530/345; 424/178.1; 424/179.1; 424/181.1
(58) Field of Search ............................... 514/18, 19, 2; 530/330, 331, 399, 345; 424/178.1, 179.1, 181.1

(56) References Cited

U.S. PATENT DOCUMENTS

| | | | |
|---|---|---|---|
| 4,975,278 A | 12/1990 | Senter et al. ............... 424/94.3 |
| 5,017,693 A | 5/1991 | Hylarides et al. ............ 530/390 |
| 5,066,716 A * | 11/1991 | Robey ........................ 525/54.1 |
| 5,084,560 A | 1/1992 | Hellstrom et al. .......... 530/390 |
| 5,116,944 A | 5/1992 | Sivam et al. ................ 530/362 |
| 5,137,877 A | 8/1992 | Kaneko et al. ................ 514/25 |
| 5,252,713 A | 10/1993 | Morgan et al. .......... 530/391.7 |
| 5,286,846 A * | 2/1994 | Inman ........................ 525/54.1 |
| 5,349,066 A | 9/1994 | Kaneko et al. .............. 546/294 |
| 5,489,516 A | 2/1996 | Broudy et al. .............. 435/7.23 |
| 5,563,250 A | 10/1996 | Hylarides et al. ............ 536/4.1 |
| 5,606,017 A | 2/1997 | Willner et al. ............... 530/322 |
| 5,606,047 A * | 2/1997 | Coutts ........................ 536/26.1 |
| 5,622,929 A | 4/1997 | Willner et al. .................. 514/8 |
| 5,635,603 A | 6/1997 | Hansen et al. ........... 530/391.5 |
| 5,661,025 A * | 8/1997 | Szoka ...................... 435/172.3 |

FOREIGN PATENT DOCUMENTS

| | | |
|---|---|---|
| EP | 0 328 147 A2 | 8/1989 |
| EP | 0 457 250 A2 | 11/1991 |
| WO | WO 91/18016 | 11/1991 |

OTHER PUBLICATIONS

Dawson, J. Am. Chem. Soc. 115, 7263, 1993.*
Dzieduszycka, Farmaco Ed. Sci 41, 881, 1986.*
Levin, FEBS Lett 98, 119, 1979.*
Trouet, Drug Targeting, Proc. Symp Meeting Date 1984, 1–12, 1985.*
Szeto, Biochemical Pharmacology 28, 2633, 1979.*
Pietersz, Avances in Experimental Medicine and Biology 353, 169, 1994.*
Langer, J Med Chem 44 1341, 2001.*
Kuefner, Adv Enzyme Regul 27, 3, 1988.*
Trouet, Proc Natl Acad Sci 79, 626, 1982.*
Kirschke, Acta Biol. Med. Ger. 40, 1427, 1981.*
Marks, J Neurosci Res. 5, 217, 1980.*
Planta, Biochim Biophys Acta 53, 443, 1961.*
Ferguson, J. Biol. Chem. 248, 6701, 1973.*

* cited by examiner

*Primary Examiner*—Christopher S. F. Low
*Assistant Examiner*—David Lukton
(74) *Attorney, Agent, or Firm*—Keith R. Lange; Audrey F. Sher

(57) ABSTRACT

Conjugates containing a targeting ligand, such as an antibody, a therapeutically active drug and a branched peptide linker. The branched peptide linker contains two or more amino acid moieties that provide an enzyme cleavage site. The number of drugs capable of being bonded to the branched linkers varies by a factor of two for each generation of branching.

35 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: Unknown
<220> FEATURE:
<223> OTHER INFORMATION: Description of Unknown Organism: Synthesized

```
<400> SEQUENCE: 1

Ala Leu Ala Leu
 1

<210> SEQ ID NO 2
<211> LENGTH: 4
<212> TYPE: PRT
<213> ORGANISM: Unknown
<220> FEATURE:
<223> OTHER INFORMATION: Description of Unknown Organism: Synthesized

<400> SEQUENCE: 2

Gly Phe Leu Gly
 1
```

BRANCHED PEPTIDE LINKERS

CROSS-REFERENCE TO RELATED APPLICATION

This application claims the benefit of U.S. Provisional Application No. 60/030,367 filed Nov. 5, 1996.

BACKGROUND OF THE INVENTION

Bifunctional compounds which link cytotoxic reagents to antibodies (i.e., "linkers") are known in the art. These compounds have been particularly useful in the formation of immunoconjugates directed against tumor associated antigens. Such immunoconjugates allow the selective delivery of toxic drugs to tumor cells. (See e.g., Hermentin and Seiler, "Investigations With Monoclonal Antibody Drug Conjugates," Behring Insti. Mitl. 82:197–215 (1988); Gallego et al., "Preparation of Four Daunomycin-Monoclonal Antibody 791T/36 Conjugates With Anti-Tumor Activity". Int. J. Cancer 33:737–44 (1984); Arnon et al., "In Vitro and In Vivo Efficacy of Conjugates of Daunomycin With Anti-Tumor Antibodies," Immunological Rev. 62:5–27 (1982).

Greenfield et al. have described the formation of acid-sensitive immunoconjugates containing the acylhydrazide conjugated via an acylhydrazone bond to the 13-keto position of an anthracycline molecule, and conjugation of this anthracycline derivative to an antibody molecule (Greenfield et al., European Patent Publication EP 0 328 147, published Aug. 16, 1989, which corresponds to pending U.S. Ser. No. 07/270,509, filed Nov. 16, 1988 and U.S. Ser. No. 07/155,181, filed Feb. 11, 1988, now abandoned). This latter reference also discloses specific thioether-containing linkers and conjugates, including hydrazone thioether containing immunoconjugates.

Kaneko et al. (U.S. Pat. No. 5,137,877 which is equivalent to European Patent Publication, EP A 0 457 250, published Nov. 21, 1991) have also described the formation of conjugates containing anthracycline antibiotics attached to a bifunctional linker by an acylhydrazone bond at the C-13 position of an anthracycline molecule. In their invention the linkers contain a reactive pyridinyidithio- or an ortho-nitrophenyldithio- group, by which the linker reacts with a suitable group attached to a cell reactive ligand, to form the completed conjugate.

Conjugates which rely on simple acid hydrolysis may release the drug prematurely. Accordingly, it would be desirable to have conjugates that release active drug in a more site-specific fashion. European Patent Publication 94107501.2 discloses lysosomal enzymes-cleavable antitumor drug conjugates which are selectively activatible at the site of the tumor. However, one of the problems with prior art immunoconjugates is the relatively low ratio of drug to targeting ligand (e.g., immunoglobulin) achievable. It would be highly desirable to have immunoconjugates, activatible at the tumor site, which provide a higher ratio of drug to targeting ligand.

SUMMARY OF THE INVENTION

The present invention provides novel branched peptide linkers. The novel linkers are used to prepare novel drug/linker molecules and biologically active conjugates composed of a targeting ligand, a therapeutically active drug, and a branched peptide linker. The novel conjugates are selectively activatible at the site of of a selected target cell population recognized by the targeting ligand.

As used herein the term "drug/linker" or "linker/drug" refers to the branched peptide linker molecule coupled to two or more therapeutically active drug molecules, and the term "conjugate" refers to the drug/linker molecule coupled to the targeting ligand.

The branched peptide linker contains a protein peptide spacer and may also contain a self-immolating spacer which spaces the protein peptide sequence and the drug. The linkers of the invention are branched so that more than one drug molecule per linker are coupled to the targeting ligand. The number of drugs attached to each linker varies by a factor of 2 for each generation of branching. Thus, the number of drug molecules per molecule of linker can be 2, 4, 8, 16, 32, 64, etc. The factor of branching can be expressed mathematically as $2^n$, wherein n is a positive integer. Thus, a singly branched linker will have a first generation of branching or $2^1$, i.e., contains a potential of two drug molecules per linker. A doubly branched linker will have a second generation of branching or $2^2$, i.e., contains a potential of four drug molecules per linker.

As n rises from n=1, there is a tendency for the solubility of the immunoconjugate to diminish. Solubility can be enhanced by using more water-soluble peptides, or addition of a water-solubilizing moiety such as polyethylene glycol or charged species, e.g., β-alanine, to the drug in such a way that it is released from the drug by either the low pH or the enzymes of the liposomal milieu.

The present invention is directed to a branched peptide linker for linking a thiol group derived from a targeting ligand to two or more drug moieties which comprises a compound having a terminus containing a thiol acceptor for binding to a thiol group (also called a sulfhydryl group) derived from a targeting ligand, at least one point of branching which is a polyvalent atom, such as a carbon atom or a nitrogen atom, allowing for a level of branching of $2^n$, wherein n is a positive integer, at least two amino acid moieties per branch providing at least one enzymatic site per branch, and at least two other termini containing groups capable of forming covalent bonds with chemically reactive functional groups derived from a drug moiety. It is preferred that n is 1, 2, 3, or 4; more preferably 1, 2, or 3; and most preferably 1 or 2. It is also preferred that the targeting ligand is an antibody or fragment thereof.

As used in the preceeding paragraph, the phrase "thiol group derived from the targeting ligand" means that the thiol group is already present on the targeting ligand or that the targeting ligand is chemically modified to contain a thiol group, which modification optionally includes a thiol spacer group between the targeting ligand and the thiol group. Likewise, the phrase "chemically reactive functional group derived from a drug moiety" means that the chemically reactive functional group is already present on the drug or the drug is chemically modified to contain such chemically reactive functional group. Such chemically reactive functional groups are groups that are capable of forming covalent bonds with a linker terminus. Examples of such chemically reactive functional groups include primary or secondary amino, hydroxyl, sulfhydroxyl, carboxyli, aldehyde, ketone, and the like.

Also provided by the invention are intermediates for preparing the linkers, drug/linkers, and/or conjugates; and a method for treating or preventing a selected disease state which comprises administering to a patient a conjugate of the invention.

The selected target cell population recognized by the targeting ligand is preferably a tumor.

An aspect of the invention provides tumor-specific conjugates which are highly selective substrates for drug-activating enzymatic cleavage by one or more tumor-associated enzymes.

A further aspect of the invention provides tumor-specific drug conjugates wherein the activating enzyme is one which is present in the tumor in sufficient amounts to generate cytotoxic levels of free drug in the vicinity of the tumor.

Another aspect of the invention provides tumor-specific drug conjugates which are stable to adventitious proteases in blood.

A still further aspect of the present invention provides a tumor-specific conjugate in accordance with the preceding aspects, which is considerably less toxic than the activated drug.

In another aspect the present invention provides methods for delivering the conjugates to target cells in which a modification in biological process is desired, such as in the treatment of diseases such as cancer.

The present invention also provides a method for delivering to the site of tumor cells in a warm-blooded animal an active antitumor drug by administering to said warm-blooded animal the conjugate according to this invention.

The above and other aspects of the present invention are achieved by derivatizing a drug (e.g., an antitumor agent) linked to a ligand through a peptide linker, made up of a protein peptide sequence and a self-immolating spacer, at a reactive site appropriate for inhibiting the pharmacological activity of the antitumor agent to thereby convert the antitumor agent into a pharmacologically inactive peptidyl derivative conjugate. The peptide linker has at least two amino acid residue sequences specifically tailored so as to render the peptidyl derivatives selective substrates for drug-activating enzymatic cleavage by one or more lysosomal proteases, such as cathepsin B, C, D, or L. The enzymatic cleavage reaction will remove the peptide linker moiety from the drug conjugate and effect release of the antitumor agents in pharmacologically active form selectively at the tumor site. In comparison with ligand-drug linkers which rely on simple acid hydrolysis for drug release this new method provides significantly less systemic toxicity due to premature linker hydrolysis in the blood, consequently a greater amount of the drug is delivered to the tumor site, and the method results in a longer storage life and simplified handling conditions for the conjugate.

The conjugates of the present invention show significantly less systemic toxicity than biparte conjugates and free drug. The conjugates of the invention retain both specificity and therapeutic drug activity for the treatment of a selected target cell population. They may be used in a pharmaceutical composition, such as one comprising a pharmaceutically effective amount of a compound of Formula (III) below, associated with a pharmaceutically acceptable carrier, diluent or excipient.

The present invention is directed to a linker molecule of the formula

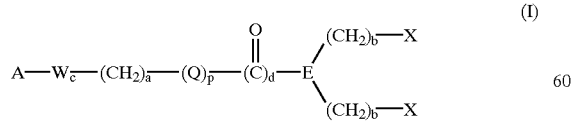

(I)

wherein
A is a thiol acceptor;
W is a bridging moiety;
c is an integer of 0 to 1;

a is an integer of 2 to 12;
Q is O, NH, or N-lower alkyl;
p is an integer of 0 or 1;
d is an integer of 0 or 1;
E is a polyvalent atom;
each b is an integer of 1 to 10;
each X is of the formula

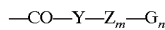

wherein
Y is two amino acid residues in the L form;
Z is one or two amino acid residues;
m is an integer of 0 or 1;
G is a self-immolative spacer; and
n is a integer of 0 or 1; provided that when n is 0 then
   —Y—$Z_m$
is ala-leu-ala-leu or gly-phe-leu-gly;
or each X is of the formula

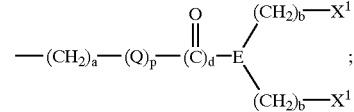

wherein each $X^1$ is of the formula

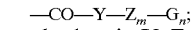

and wherein Y, Z, Q, E, G, m, d, p, a, b and n are as defined above;
or each $X^1$ is of the formula

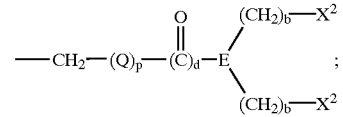

wherein each $X^2$ is of the formula

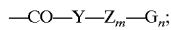

and wherein Y, Z, G, Q, E, m, d, p, a, b and n are as defined above;
or each $X^2$ is of the formula

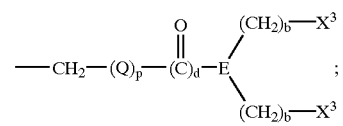

wherein each $X^3$ is of the formula

and wherein Y, Z, G. Q, E, m, d, p, a, b and n are as defined above;
or each $X^3$ is of the formula

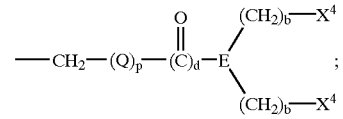

wherein each $X^4$ is of the formula

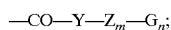

and wherein Y, Z; G, Q, E, m, d, p, a, b and n are as defined above.

The present invention is also directed to a drug/linker molecule of the formula

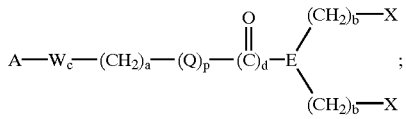
(II)

wherein
A is a thiol acceptor;
W is a bridging moiety;
c is an integer of 0 to 1;
a is an integer of 2 to 12;
Q is O, NH, or N-lower alkyl;
p is an integer of 0 or 1;
d is an integer of 0 or 1;
E is a polyvalent atom;
each b is an integer of 1 to 10;
each X is of the formula

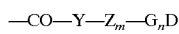

wherein
Y is two amino acid residues in the L form;
Z is one or two amino acid residues;
m is an integer of 0 or 1;
G is a self-immolative spacer;
n is a integer 0 or 1; provided that when m is 0 then —Y—$Z_m$— is ala-leu-ala-leu (SEQ ID NO:1) or gly-phe-leu-gly (SEQ ID NO:2); and
D is a Drug moiety having a backbone and at least one chemically reactive functional group pendant thereto chemically reacted to the self-immolative spacer or terminal amino acid residue to form a covalent bond, said functional group selected from the group consisting of a primary or secondary amine, hydroxyl, sulfhydryl, carboxyl, aldehyde or ketone;
or each X is of the formula

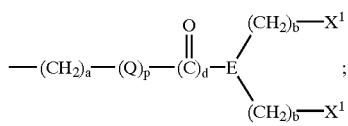

wherein each $X^1$ is of the formula

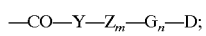

wherein Y, Z, G, D, Q, E, m, d, p and n are as defined above;
or each $X^1$ is of the formula

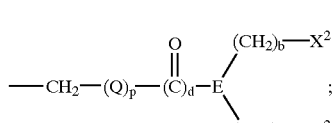

wherein each $X^2$ is of the formula

and wherein Y, Z, G, D, Q, E, m, d, p, a, b and n are as defined above;
or each $X^2$ is of the formula

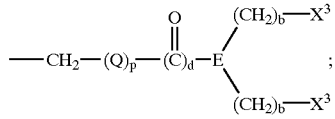

wherein each $X^3$ is of the formula

—CO—Y—$Z_m$—$G_n$—D;

and wherein Y, Z, GI D, Q, E, m, d, p, a, b and n are as defined above;
or each $X^3$ is of the formula

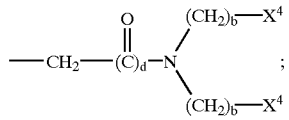

and wherein each $X^4$ is the formula

—CO—Y—$Z_m$—$G_n$—D;

and wherein Y, Z, G, D, Q, E, m, d, p, a, b and n are as defined above.

Furthermore, the present invention is directed to conjugate of the formula

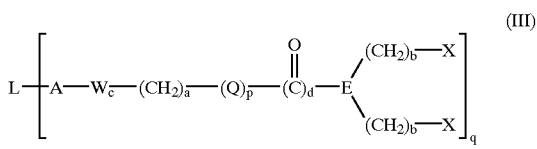
(III)

wherein
L is a ligand;
q is an integer of 1 to 10;
A is a thiol acceptor;
W is a bridging moiety;
c is an integer from 0 to 1;
a is an integer of 2 to 12;
Q is O, NH, or N-lower alkyl;
p is an integer of 0 or 1;
d is an integer of 1 or 2;
E is a polyvalent atom;
each b is an integer of 1 to 10;
each X is of the formula

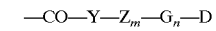

wherein
Y is two amino acid residues in the L form;
Z is one or two amino acid residues;
m is an integer of 0 or 1;
G is a self-immolative spacer; and
n is a integer of 0 or 1; provided that when n is 0 then —Y—$Z_m$— is ala-leu-ala-leu (SEQ ID NO:1) or gly-phe-leu-gly (SEQ ID NO:2);
D is a drug moiety having a backbone and at least one chemically reactive functional group pendant thereto reacted to the self-immolative spacer to form a covalent bond, said funtional group selected from the group consisting of a primary or secondary amine, hydroxyl, carboxyl, sulfhydryl, aldehyde, or ketone;

or X is of the formula

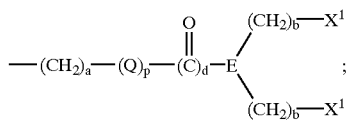

wherein each $X^1$ is of the formula

—CO—Y—$Z_m$—$G_n$—D;

and wherein Y, Z, G, D, O, E, m, d, p, a, b and n are as defined above;
or each $X^1$ is of the formula

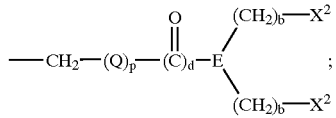

wherein each $X^2$ is of the formula

—CO—Y—$Z_m$—$G_n$—D;

and wherein Y, Z, G, D, Q, E, m, d, p, a, b and n are as defined above;
or each $X^2$ is of the formula

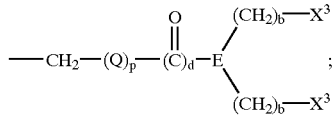

wherein each $X^3$ is of the formula

—CO—Y—$Z_m$—$G_n$—D;

wherein Y, Z, G, D, Q, E, m, d, p, a, b and n are as defined above;
or each $X^3$ is of the formula

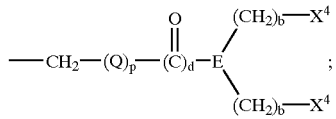

wherein end $X^4$ is of the formula

—CO—$Y_m$—$Z_m$—$G_n$—D;

wherein Y, Z, G, D, Q, E, m, d, p, a, b and n are as defined above.

As used herein the term "lower alkyl" is an alkyl group having 1 to 3 carbon atoms. It is preferred that the polyvalent atom is carbon or nitrogen.

In one embodiment the drug moiety is an anthracycline antibiotic and the targeting ligand is an antibody.

In a preferred embodiment the anthracycline is bound to the linker at an amino sugar group of the anthriacycline. It is preferred that the sugar moiety is daunosamine. The antibody then is bound, through the linker, to the anthracycline compound. In an especially preferred embodiment, this linkage occurs through a reduced disulfide group (i.e. a free sulfhydryl group (—SH)) on an antibody).

In a most preferred embodiment the anthracycline drug moiety is doxorubicin; the thiol acceptor is a Michael Addition acceptor (from which a Michael Addition Adduct is derived), more preferably is a maleimido- group; and the antibody moiety is a chimeric or humanized antibody, and the point of attachment of the linker to the drug is at the amino group of the sugar moiety of the drug.

The conjugates of the invention retain both specificity and therapeutic drug activity for the treatment of a selected target cell population. They may be used in a pharmaceutical composition, such as one comprising a pharmaceutically effective amount of a compound of Formula (III) associated with a pharmaceutically acceptable carrier, diluent or excipient.

DETAILED DESCRIPTION OF THE INVENTION

The present invention provides novel drug-linker-ligand conjugates composed of a ligand capable of targeting a selected cell population, and a drug connected to the ligand by a branched peptide linker. The linker contains a thiol acceptor such as a Michael Addition accceptor, a bridging moiety, a point of branching, and a peptide sequence per each branch containing at least two amino acid moieties which provides an enzymatic cleavage site for an enzyme such as cathepsin B, C, D, or L. The branched peptide linker may also contain a self-immolating spacer, which spaces the drug and the protein peptide sequence. It has been discovered that when the peptide seqeunce (i.e., Y—$Z_m$) is ala-leu-ala-leu- (SEQ ID NO:1) or gly-phe-leu-gly (SEQ ID NO:2), then the presence of the self-immolative spacer is optional. The reason that a self-immolative spacer is not required for these peptide sequences is not entirely understood; however, it may be due to response to different enzymes.

The targeting ligand molecule can be an immunoreactive protein such as an antibody, or fragment thereof, a non-immunoreactive protein, or peptide ligand such as bombesin or, a binding ligand recognizing a cell associated receptor such as a lectin, or any protein or peptide that possesses a reactive sulfhydryl-group (—SH) or can be modified to contain such a sulfhydryl group. The thiol acceptor carboxylic is linked to the ligand via a thioether bond, and the drug is linked to the linker via a functional group selected from primary or secondary amine, hydroxyl, sulfhydryl, carboxyl, aldehyde or ketone.

For a better understanding of the invention, the drugs, ligands, peptides and spacers will be discussed individually. The synthesis of the conjugates then will be explained.

It will be understood that in the following detailed description and appended claims, the abbreviations and nomenclature employed are those which are standard in amino acid and peptide chemistry, and that all the amino acids referred to are in the L-form unless otherwise specified.

Some abbreviations used in the present application, unless otherwise indicated, are as follows: AcOH: acetic acid; Alloc: allyloxy-carbonyl; Boc: t-butyloxycarbonyl; DBU: diazobicycloundecene; DCC: dicyclohexylcarbodiimide; DCI: direct chemical ionization; DCU: dicyclohexylurea; DIEA: diisopropylethylamine; DMAP: 4-dimethylaminopyridine; DME: 1,2-dimethoxyethane; DOX: doxorubicin; DTT: dithiothreitol; EEDQ: N-ethoxycarbonyl-2-ethoxy-1;2-dihydroquinoline; EtOAc: ethyl acetate; FAB: fast atom bombardment; Fmoc: fluorenylmethoxycarbonyl; GABA: γ-aminobutyric acid; HOBt: N-hydroxybenzotriazole; HRMS: high resolution mass spectroscopy; LDL: low density lipoprotein; MC:

6-maleimidocaproyl; MP: 3-maleimidopropionyl; MPr-BHP: maleimidopropyl-bis-hydroxypropyl; MPr-Mal: maleimidopropyl-malonyl; MEt-IBHE: maleimidoethyl-imino-bis-hydroxyethyl; MMA: mitomycin A, MMC: mitomycin C; Mtr: 4-methoxytrityl; NHS: N-hydroxysuccinimide; NMP: N-methylpyrrolidinone; PABC: p-aminobenzyl-carbamoyl; PAB-OH: p-aminobenzyl alcohol; PNP: p-nitrophenol; TFA: trifluoroacetic acid; THF: tetrahydrofuran.

The Peptide Residue (—Y—$Z_m$—)

The peptide linker of the present invention contains two, three or four amino acid residues per branch, together with the self-immolative spacer if present, that provides one or more enzyme cleavage sites. The amino acid moieties collectively form a peptide sequence.

The amino acid residues making up the peptide residues are each selected, independently, from the group of amino acids, preferably naturally occurring amino acids. The naturally occurring amino acids are alanine (Ala), arginine (Arg), asparagine (Asn), aspartic acid (Asp), cysteine (Cys), glutamic acid (Glu), glutamine (Gln), glycine (Gly), histidine (His), isoleucine (Ile), leucine (Leu), lysine (Lys) methionine (Met), ornithine (Orn), phenylalanine (Phe), proline (Pro), serine (Ser), threonine (Thr), tryptophan (Trp), tyrosine (Tyr), and valine (Val). Preferred naturally occuring amino acids are Ala, Val. Leu, Lys, Ile, Met, Phe, Trp, and Pro. Certain non-naturally occuring amino acids also can be part of the peptide residue. Such non-naturally occuring amino acids include citrulline (Cit) and protected amino acids such as naturally occuring amino acids protected with groups such as acetyl, formyl, tosyl, nitro and the like. When specific amino acids are indicated herein as part of a peptide sequence, they are in the L form unless specified otherwise. The amino acid residues making up the "Y" moiety must be in the L form. The amino acid residue(s) making up the "Z" moiety can be either in the L or D form. More preferred amino acids include Lys, Lys protected with acetyl or formyl, Arg, Arg arginine protected with tosyl or nitro groups, His, Orn, Orn protected with acetyl or formyl, Phe, Val, Ala, and Cit. Most preferred are Lys and Cit.

The amino acid residue sequence is specifically tailored so that it will be selectively enzymatically cleaved from the resulting peptidyl derivative drug-conjugate by one or more of the tumor-associated proteases.

The amino acid residue chain length of each branch of the peptide linker preferably ranges from that of a dipeptide to that of a tetrapeptide.

It is preferred that the first amino acid residue (i.e., the first amino acid making up "Y", read left to right) is a basic amino acid (e.g., Lys or Arg) or has strong hydrogen bonding capability (e.g., Cit). It is preferred that the second amino acid residue (i.e., the second amino acid making up "Y", read left to right) has a hydropholic side chain (e.g., Phe, Val, Ala, Leu or Ile).

The following group of exemplary peptide linker groups, are named in order to illustrate further the conjugates of the present invention:

Phe-Lys, Val-Lys, Phe-Phe-Lys, Lys-Phe-Lys, Gly-Phe-Lys, Ala-Lys,

Val-Cit, Phe-Cit, Leu-Cit, Ile-Cit, Trp-Cit, Phe-Ala, Gly-Phe-Leu-Gly,

Ala-Leu-Ala-Leu, Phe-Ng-tosyl-Arg, Phe-Ng-Nitro-Arg, Lys-Lys,

Lys-Cit, and Cit-Cit.

Specific examples of the preferred embodiment of peptide sequences include Phe-Lys, Val-Lys, Val-Cit, and D-Phe-Phe-Lys.

Numerous specific peptide linker molecules suitable for use in the present invention can be designed and optimized in their selectivity for enzymatic cleavage by a particular tumor-associated protease. The preferred peptide linkers for use in the present invention are those which are optimized toward the protease, cathepsin B, C, D, and L.

The Spacer ("G")

The molecules in accordance with the present invention may employ an intermediate self-immolative spacer moiety which spaces and covalently links together the drug moiety and the protein peptide moiety. A self-immolative spacer may be defined as a bifunctional chemical moiety which is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at one of its ends to the protein peptide moiety and covalently linked at its other end to the chemical reactive site of the drug moiety whose derivatization inhibits pharmacological activity, so as to space and covalently link together the protein peptide moiety and the drug moiety into a tripartate molecule which is stable and pharmacologically inactive in the absence of the target enzyme, but which is enzymatically cleavable by such target enzyme at the bond covalently linking the spacer moiety and the protein peptide moiety to thereby effect release of the protein peptide moiety from the tripartate molecule. Such enzymatic cleavage, in turn, will activate the self-immolating character of the spacer moiety and initiate spontaneous cleavage of the bond covalently linking the spacer moiety to the drug moiety, to thereby effect release of the drug in pharmacologically active form.

In the molecules of Formulas I, II, and III:

G is a self-immolative spacer moiety which spaces and covalently links together the drug moiety and the amino acid, in which the spacer is linked to the drug moiety via the T moiety (as used in the following formulas "T" represents a nucleophilic atom which is already contained in the Drug), and which may be represented by the structures of Formulae, (IV), (V), (VI), (VII),or (VIII):

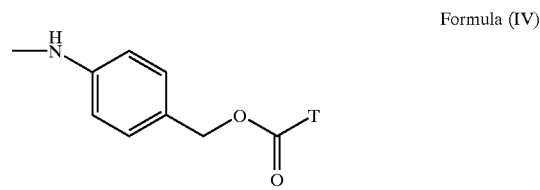

Formula (IV)

in which T is O, N or S,

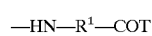    Formula (V)

in which T is O, N or S, and $R^1$ is $C_1$–$C_5$ alkyl;

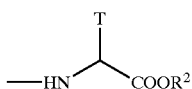

Formula (VI)

(J. Med. Chem., 27: 1447 (1984))
in which T is O, N or S, and
$R^2$ is H or $C_1$–$C_5$ alkyl;

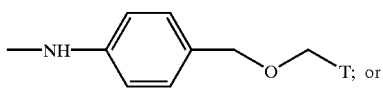

Formula (VII)

in which T is O, N or S,

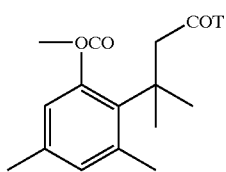

Formula (VIII)

in which T is O, S or N.

As used herein "$C_1$–$C_5$ alkyl" is meant to include a branched or unbranched hydrocarbon chain having, unless otherwise noted, one to five carbon atoms, including but not limited to methyl, ethyl, isopropyl, n-propyl, sec-butyl, isobutyl, n-butyl and the like.

A preferred G self-immolative spacer moiety suitable for use in the present invention is PABC represented by the Formula (IVa):

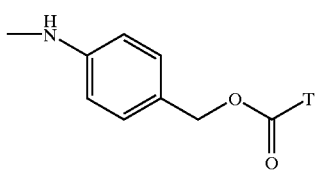

Formula (IVa)

Another preferred G self-immolative spacer moiety suitable for use in the present invention is GABA represented by the Formula (Va):

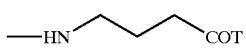

Formula (Va)

Yet another preferred G self-immolative spacer moiety suitable for use in the present invention is α,α-dimethyl GABA represented by the Formula (Vb):

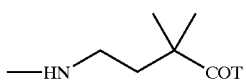

Formula (Vb)

Another preferred G self-immolative spacer moiety suitable for use in the present invention is β,β-dimethyl GABA represented by the Formula (Vc):

Formula (Vc)

The Thiol Acceptor

In the molecules of Formulas I, II, and III, the thiol acceptor "A" is linked to the ligand via a sulfur atom derived from the ligand. The thiol acceptor becomes a thiol adduct after bonding to the ligand through a thiol group via a thioester bond. The thiol acceptor can be, for example, an alpha-substitited acetyl group. Such a group has the formula

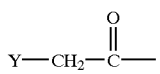

wherein Y is a leaving group. Examples of leaving groups include Cl, Br, I, mesylate, tosylate, and the like. If the thiol acceptor is an alpha-substituted acetyl group, the thiol adduct after linkage to the ligand forms the bond
—S—$CH_2$—

Preferably, the thiol acceptor is a Michael Addition acceptor. A representative Michael Addition acceptor of this invention has the formula

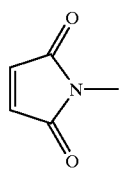

After linkage the thiol group of the ligand, the Michael Addition acceptor becomes a Michael Addition adduct, such as of the formula A

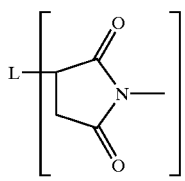

A wherein L is ligand.

The Bridging Group ("W")

The bridging group ia a bifunctional chemical moiety which is capable of covalently linking together two spaced chemical moieties into a stable tripartate molecule. Examples of bridging groups are described in S. S. Wong, *Chemistry of Protein Conjugation and Crosslinking.* CRC Press, Florida, (1991); and G. E. Means and R. E. Feeney, *Bioconiugate Chemistry,* vol. 1, pp.2–12, (1990), the disclosures of which are incorporated herein by reference. Specifically, the bridging group "W" covalently links the thiol acceptor to a keto moiety. An example of a bridging group has the formula

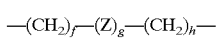

wherein f is an integer of 0 to 10, h is an integer of 0 to 10, g is an integer of 0 or 1, provided that when g is 0, then f+h is 1 to 10, Z is S, O, NH, $SO_2$, phenyl, naphthyl, a polyethylene glycol, a cycloaliphatic hydrocarbon ring containing 3 to 10 carbon atoms, or a heteroaromatic hydrocarbon ring containing 3 to 6 carbon atoms and 1 or 2 heteroatoms selected from O, N, or S.

Preferred cycloaliphatic moieties include cyclopropyl, cyclobutyl, cyclopentyl, cyclohexyl, and the like. Preferred heteroaromatic moieties include pyridyl, polyethlene glycol (1–20 repeating units), furanyl, pyranyl, pyrimidinyl, pyrazinyl, pyridazinyl, oxazinyl, pyrrolyl, thiazolyl, morpholinyl, and the like.

In the bridging group it is preferred that when g is 0, f+h is an integer of 2 to 6 preferably 2 to 4 and more preferably 2. When g is 1, it is preferred that f is 0, 1 or 2, and that h is 0, 1 or 2.

Preferred bridging groups coupled to thiol acceptors are shown in the Pierce Catalog, pp. E-12, E-13, E-14, E-15, E-16, and E-17 (1992).

The Drug

The drug conjugates of the present invention are effective for the usual purposes for which the corresponding drugs are effective, and have superior efficacy because of the ability, inherent in the ligand, to transport the drug to the desired cell where it is of particular benefit. Further, because the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a protein such as tumor necrosis factor.

The preferred drugs for use in the present invention are cytotoxic drugs, particularly those which are used for cancer therapy. Such drugs include, in general, DNA damaging agents, anti-metabolites, natural products and their analogs. Preferred classes of cytotoxic agents include, for example, the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, differentiation inducers, and taxanes. Particularly useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, carminomycin, aminopterin, tallysomycin, podophyllotoxin and podophyllotoxin derivatives such as etoposide or etoposide phosphate, vinblastine, vincristine, vindesine, taxol, taxotere, retinoic acid, butyric acid, $N^8$-acetyl spermidine, camptothecin, and their analogues.

As noted previously, one skilled in the art may make chemical modifications to the desired compound in order to make reactions of that compound more convenient for purposes of preparing conjugates of the invention.

In the conjugate of Formula I,

D is a drug moiety having pendant to the backbone thereof a chemically reactive functional group, by means of which the drug backbone is bonded to the protein peptide linker, said functional group selected from the group consisting of a primary or secondary amine, hydroxyl, sulfhydryl, carboxyl, aldehyde or a ketone. Representative of said amino containing drugs are mitomycin-C, mitomycin-A, daunorubicin, doxorubicin, aminopterin, actinomycin, bleomycin, 9-amino camptothecin, $N^8$-acetyl spermidine, 1-(2-chloroethyl)-1,2-dimethanesulfonyl hydraxide, tallysomycin, cytarabine and derivatives thereof.

Representative of said alcohol group containing drugs are etoposide, camptothecin, taxol, esperamicin, 1,8-dihydroxy-bicyclo[7.3.1]trideca-4-9-diene-2,6-diyne-13-one, (U.S. Pat. No. 5,198,560), podophyllotoxin, anguidine, vincristine, vinblastine, morpholine-doxorubicin, n-(5,5-diacetoxy-pentyl)doxorubicin, and derivatives thereof.

Representative of said sulfhydryl containing drugs are esperamicin and 6-mercaptopurine, and derivatives thereof. Representative of said carboxyl containing drugs are methotrexate, camptothecin (ring-opened form of the lactone), butyric acid, retinoic acid, and derivatives thereof. Representative of said aldehyde and ketone containing drugs are anguidine and anthracyclines such as doxorubicin, and derivatives thereof.

A highly preferred group of cytotoxic agents for use as drugs in the present invention include drugs of the following formulae:

THE MITOMYCIN GROUP OF FORMULA (1)

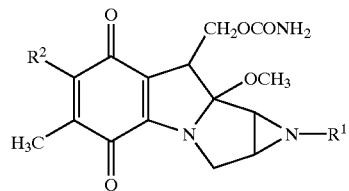

in which $R^1$ is hydrogen or methyl;

$R^2$ is $-NH_2$, $-OCH_3$, $-O(CH_2)_2OH$, $-NH(CH_2)_2SS(CH_2)_2NHAc$, $-NHCH-C\equiv CH$, $-NH(CH_2)_2SS(C_6H_4)NO_2$, $-O(CH_2)_2SS(CH_2)_2OH$, $-N=CH-NHOCH_3$, $-NH(C_6H_4)OH$, $-NH(CH_2)_2SS(CH_2)_2NHCO(CH_2)_2CH(NH_2)COOH$

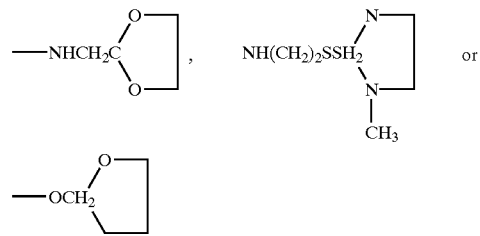

THE BLEOMYCIN GROUP OF FORMULA (2)

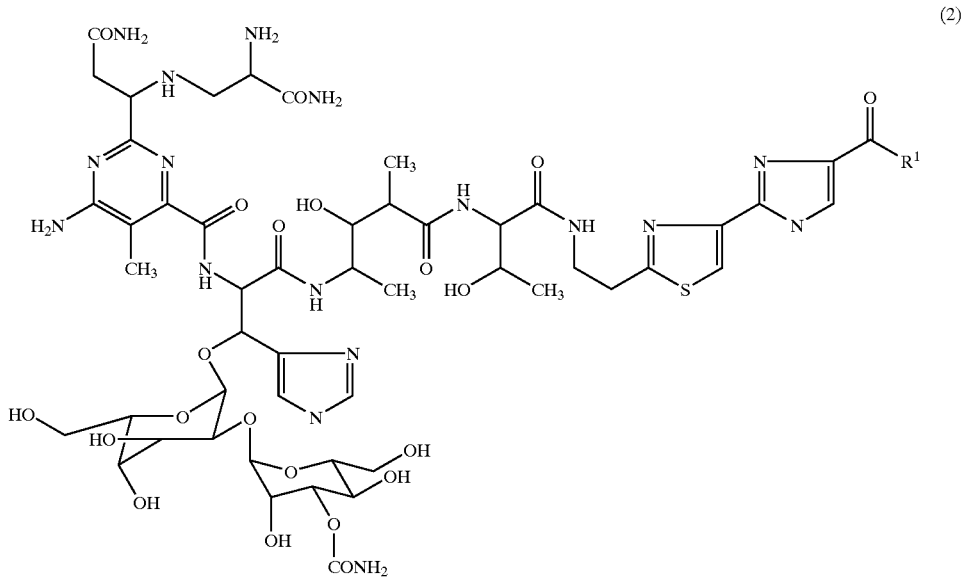

in which

R[1] is hydroxy, amino, $C_1$–$C_3$ alkylamino. di($C_1$–$C_3$ alkyl)armino, $C_4$–$C_6$ potymethylene amino,

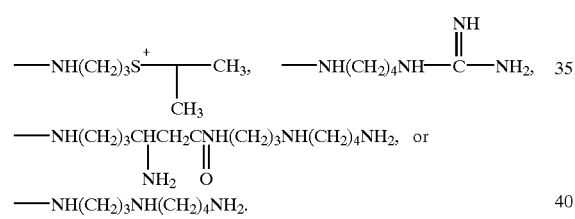

THE METHOTREXATE GROUP OF FORMULA (3)

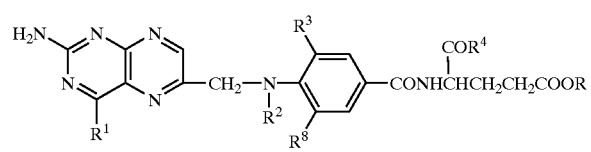

in which

R[1] is amino or hydroxy;

R[2] is hydrogen or methyl;

R[3] is hydrogen, fluoro, chloro, bromo or iodo;

R[4] is hydroxy or a moiety which complete a salt of the carboxylic acid.

MELPHALAN OF FORMULA (4)

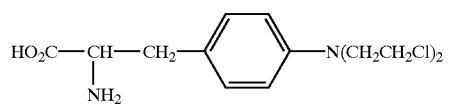

6-MERCAPTOPURINE OF FORMULA (5)

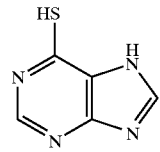

A CYTOSINE ARABINOSIDE OF FORMULA (6)

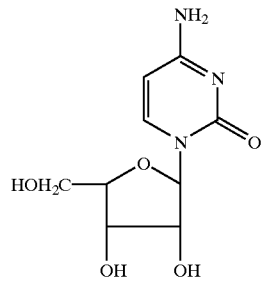

THE PODOPHYLLOTOXINS OF FORMULA (7)

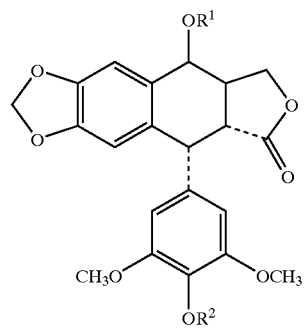

(7)

wherein
R² is hydrogen
R¹ is hydrogen or

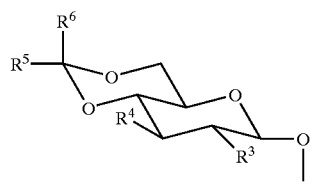

wherein
R³ is $NH_2$, OH, $OCH_3$, $NH(C_1-C_3$ akyl) or $N(C_1-C_3$ alkyl$)_2$
R⁴ is OH, or $NH_2$,
R⁵ is methyl or thienyl,
R⁶ is hydrogen or methyl, or a phosphate salt thereof.
As used herein "($C_1-C_3$ akyl)" means a straight or branched carbon chain having from one to three carbon atoms; examples include methyl, ethyl, n-propyl and isopropyl.

THE VINCA ALKALOID GROUP OF DRUGS OF FORMULA (8)

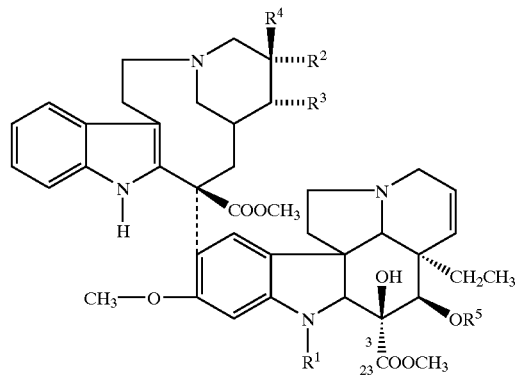

in which
R¹ is H, $CH_3$ or CHO;
when R² and R³ are taken singly, R³ is H, and one of R⁴ and $2 is ethyl and the other is H or OH:
when R² and R³ are taken together with the carbons to which they are attached, they form an oxirane ring in which case R⁴ is ethyl;
R⁵ is hydrogen, ($C_1-C_3$ alkyl)—CO, or chlorosubstituted ($C_1-C_2$ alkyl)—CO.

As used herein "$C_1-C_3$ alkyl" means a straight or branched carbon chain having from one to three carbon atoms; examples include methyl, ethyl, n-propyl and isopropyl.

DIFLUORONUCLEOSIDES OF FORMULA (9)

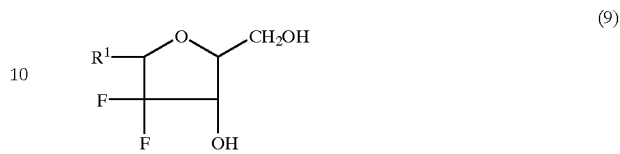

(9)

in which R¹ is a base of one of the formulae:

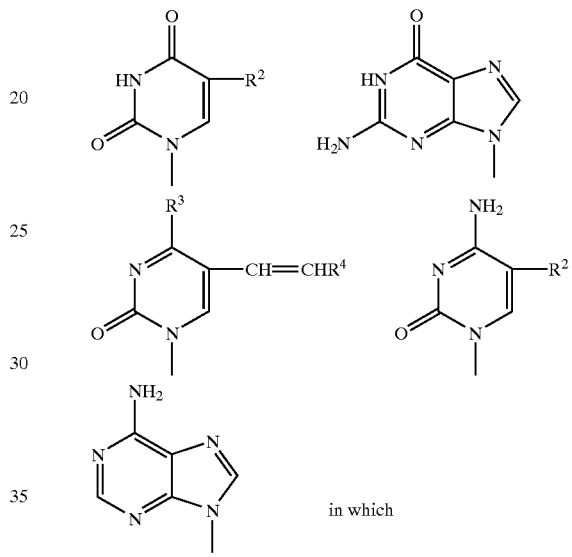

in which in which
R² is hydrogen, methyl, bromo, fluoro, chloro, or iodo;
R³ is —OH or —$NH_2$;
R⁴ is hydrogen, bromo, chloro, or iodo.

TAXOLS OF FORMULA (10)

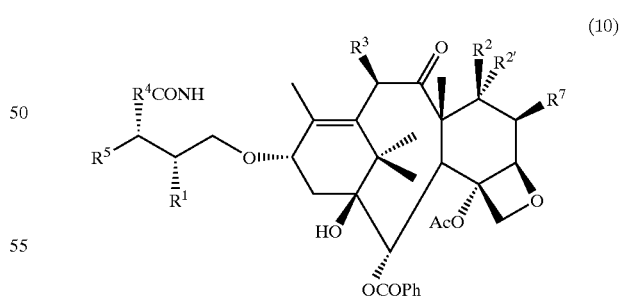

(10)

wherein
R¹ is hydroxy;
R² is hydrogen or hydroxy;
R² is hydrogen, hydroxy, or acetoxy;
R⁷ is hydrogen or hydroxy;
R³ is hydrogen, hydroxy, or acetoxy;
R⁴ is aryl, substituted aryl, $C_{1-6}$ alkyl, $C_{2-6}$ alkenyl, $C_{2-6}$ alkynyl or t-butoxy;

$R^5$ is $C_{1-6}$ alkyl, $C_{2-6}$ alkenyl, $C_{2-6}$ alkynyl, or —Z—$R^6$;

Z is a direct bond, $C_{1-6}$ alkyl or $C_{2-6}$ alkenyl;

$R^6$ is aryl, substituted aryl, $C_{3-6}$ cycloalkyl, thienyl or furyl.

As used herein, "alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-butyl, isopentyl, and n-hexyl. "Alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. "Alkynyl" means a straight or branched carbon chain having at least one carbon-carbon triple bond, and from two to six carbon atoms; examples include ethynyl, propynyl, butynyl, and hexynyl. "Aryl" means aromatic hydrocarbon having from six to ten carbon atoms; examples include phenyl and naphthyl. "Substituted aryl" means aryl substituted with at least one group selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, and amido.

ANGUIDINES OF FORMULA (11)

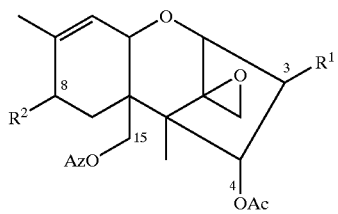

(11)

wherein $R^1$ is OH or O;

$R^2$ is HorO;

Anguidine can be targeted at the C-3, C-4, C-8 or C-15 positions, as an ester or hydrazone

PHENYLENE DIAMINE MUSTARD (12)

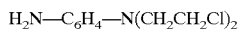

THE ANTHRACYCLINES ANTIBIOTICS OF FORMULA (13)

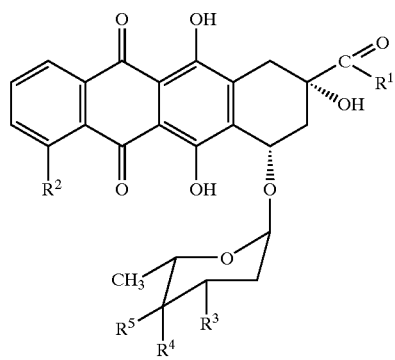

(13)

wherein $R^1$ is —$CH_3$, —$CH_2OH$, —$CH_2OCO(CH_2)_3CH_3$ or —$CH_2OCOCH(OC_2H_5)_2$ $R^2$ is —$OCH_3$, —OH or —H $R^3$ is —$NH_2$, —$NHCOCF_3$, 4-morpholinyl, 3-cyano-4-morpholinyl, 1-piperidinyl, 4-methoxy-1-piperidinyl, benzylamine, dibenzylamine, cyanomethylamine, 1-cyano-2-methoxyethyl amine, or NH—$(CH_2)$4-CH$(OAc)_2$;

$R^4$ is —OH, —OTHP, or —H; and

R5 is —OH or —H provided that R5 is not —OH when R4 is —OH or —OTHP.

One skilled in the art understands that structural Formula (13) includes compounds which are drugs, or are derivatives of drugs, which have acquired in the art different generic or trivial names. Table I, which follows, represents a number of anthracycline drugs and their generic or trivial names and which are especially preferred for use in the present invention.

Of the compounds shown in Table I, the most highly preferred drug is Doxorubicin. Doxorubicin (also referred to herein as "DOX") is that anthracyclin shown in the formula of Table I in which $R_1$ is —$CH_2OH$, $R^2$ is —$OCH_3$, $R^3$ is —$NH_2$, $R^4$ is —OH, and $R^5$ is —H.

TABLE I

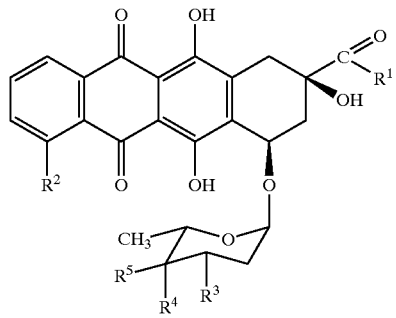

| Compound | $R^1$ | $R^2$ | $R^3$ | $R^4$ | $R^5$ |
|---|---|---|---|---|---|
| Daunorubicin[a] | $CH_3$ | $OCH_3$ | $NH_2$ | OH | H |
| Doxorubicin | $CH_2OH$ | $OCH_3$ | $NH_2$ | OH | H |
| Detorubicin | $CH_2OCOCH(OC_2H_5)_2$ | $OCH_3$ | $NH_2$ | OH | H |
| Carminomycin | $CH_3$ | OH | $NH_2$ | OH | H |

TABLE I-continued

[Structure: anthracycline core with substituents $R^1$ (on carbonyl), $R^2$, and a sugar moiety bearing $R^3$, $R^4$, $R^5$ and a $CH_3$ group]

| Compound | $R^1$ | $R^2$ | $R^3$ | $R^4$ | $R^5$ |
|---|---|---|---|---|---|
| Idarubicin | $CH_3$ | H | $NH_2$ | OH | H |
| Epirubicin | $CH_2OH$ | $OCH_3$ | $NH_2$ | H | OH |
| Esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |
| Morpholino-Dox | $CH_2OH$ | $OCH_3$ | —N(morpholino) | OH | H |
| Cyano-morpholino-Dox | $CH_2OH$ | $OCH_3$ | —N(cyano-morpholino) | OH | H |
| DAPDox | $CH_2OH$ | $OCH_3$ | —$NH(CH_2)_4CH(OAc)_2$ | OH | H |

<sup>a</sup>"Daunomycin" is an alternate name for daunorubicin

The most highly preferred drugs are taxol, mitomycin C, and the anthracycline antibiotic agents of Formula (13), described previously.

The Ligand

The "ligand" includes within its scope any molecule that specifically binds or reactively associates or complexes with a receptor or other receptive moiety associated with a given target cell population. This cell reactive molecule, to which the drug reagent is linked via the linker in the conjugate, can be any molecule that binds to, complexes with or reacts with the cell population sought to be therapeutically or otherwise biologically modified and, which possesses a free reactive sulfhydryl (—SH) group or can be modified to contain such a sulfhydryl group. The cell reactive molecule acts to deliver the therapeutically active drug moiety to the particular target cell population with which the ligand reacts. Such molecules include, but are not limited to, large molecular weight proteins such as, for example, antibodies, smaller molecular weight proteins, polypeptides or peptide ligands, and non-peptidyl ligands.

The non-immunoreactive protein, polypeptide, or peptide ligands which can be used to form the conjugates of this invention may include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and insulin-like growth factors I and II. Non-peptidyl ligands may include, for example, carbohydrates, lectins, and apoprotein from low density lipoprotein.

The immunoreactive ligands comprise in antigen-recognizing immunoglobulin (also referred to as "antibody"), or an antigen-recognizing fragment thereof. Particularly preferred immunoglobulins are those immunoglobulins which can recognize a tumor-associated antigen. As used, "immunoglobulin" may refer to any recognized class or subclass of immunoglobulins such as IgG, IgA, IgM, IgD, or IgE. Preferred are those immunoglobulins which fall within the IgG class of immunoglobulins. The immunoglobulin can be derived from any species. Preferably, however, the immunoglobulin is of human, murine, or rabbit origin. Furthermore, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments may include, for example, the Fab', F(ab')$_2$, F$_v$ or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See generally, Parham, *J. Immunology*, 131, 2895 (1983); Lamoyi et al., *J. Immunological Methods*, 56, 235 (1983); Parham, id., 53, 133 (1982); and Matthew et al., id., 50, 239 (1982).

The immunoglobulin can be a "chimeric antibody" as that term is recognized in the art. Also the immunoglobulin may be a "bifunctional" or "hybrid" antibody, that is, an antibody which may have one arm having a specificity for one antigenic site. such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or more or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT Application WO83/03679, published Oct. 27, 1983, and published European Application EPA 0 217 577, published Apr. 8, 1987, both of which are incorporated herein by reference. Particularly preferred bifunctional antibodies are those biologically prepared from a "polydoma" or "quadroma" or which are synthetically prepared with cross-linking agents such as bis-(maleimido)-methyl ether ("BMME"), or with other cross-linking agents familiar to those skilled in the art.

In addition the immunoglobulin may be a single chain antibody ("SCA"). These may consist of single chain Fv fragments ("scFv") in which the variable light ("$V_L$") and variable heavy ("$V_H$") domains are linked by a peptide bridge or by disulfide bonds. Also, the immunoglobulin may consist of single VH domains (dAbs) which possess antigen-binding activity. See, eg., G. Winter and C. Milstein, *Nature*, 349, 295 (1991); R. Glockshuber et al., *Biochemistry* 29, 1362 (1990); and E. S. Ward et al., *Nature* 341, 544 (1989).

Especially preferred for use in the present invention are chimeric monoclonal antibodies, preferably those chimeric antibodies having specificity toward a tumor associated antigen. As used herein, the term "chimeric antibody" refers to a monoclonal antibody comprising a variable region, i.e., binding region, from one source or species and at least a portion of a constant region derived from a difference source of species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immungobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L., et al., *Proc. Natl Acad. Sci*, 81 6851 (1984).

Encompassed by the term "chimeric antibody" is the concept of "humanized antibody", that is those antibodies in which the framework or "complementarity determining regions ("CDR") have been modified to comprise the CDR of an immunoglobulin of different specificitry as compared to that of the parent immunoglobulin. In a preferred embodiment, a murine CDR is grafted into the framework region of a human antibody to prepare the "humanized antibody". See, eg., L. Riechmann et al., *Nature* 332, 323 (1988); M. S. Neuberger et al.; *Nature* 314, 268 (1985). Particularly preferred CDR's correspond to those representing sequences recognizing the antigens noted above for the chimeric and bifunctional antibodies. The reader is referred to the teaching of EPA 0 239 400 (published Sep. 30, 1987), incorporated herein by reference, for its teaching of CDR modified antibodies.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, WO86/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired-"fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, *Nature* 256, 495 (1975). In addition, hybridomas and/or monoclonal antibodies which are produced by such hybridomas and which are useful in the practice of the present invention are publicly available from sources such as the American Type Culture Collection ("ATCC") 12301 Parklawn Drive, Rockville, MD. 20852 or, commercially, for example, from Boehringer-Mannheim Biochemicals, P.O. Box 50816, Indianapolis, Ind. 46250.

Particularly preferred monoclonal antibodies for use in the present invention are those which recognize tumor associated antigens. Such monoclonal antibodies, are not to be so limited, however, and may include, for example, the following:

| Antigen Site Recognized | Monoclonal Antibodies | Reference |
| --- | --- | --- |
| Lung Tumors | KS1/4 | N. M. Varki et al., Cancer Res. 44: 681, 1984. |
|  | 534, F8; 604A9 | F. Cuttitta et al., in: G. L. Wright (ed) Monoclonal Antibodies and Cancer, Marcel Dekker, Inc., NY., p. 161, 1984. |
| Squamous Lung | G1, LuCa2, LuCa3, LuCa4 | Kyoizumi et al., Cancer Res., 45: 3274, 1985. |
| Small Cell Lung Cancer | TFS-2 | Okabe et al., Cancer Res., 45: 1930, 1985. |

-continued

| Antigen Site Recognized | Monoclonal Antibodies | Reference |
|---|---|---|
| Colon Cancer | 11.285.14 14.95.55 | G. Rowland et al., Cancer Immunol. Immunother., 19: 1, 1985. |
| | NS-3a-22, NS-10 NS-19-9, NS-33a NS-52a, 17-1A | Z. Steplewski et al., Cancer Res., 41: 2723, 1981. |
| Carcino-embryonic | MoAb 35 or ZCE025 | Acolla, R. S. et al., Proc. Nat. Acad. Sci., (USA), 77: 563, 1980. |
| Melanoma | 9.2.27 | T. F. Bumol and R. A. Reiseld, Proc. Natl. Acad. Sci., (USA), 79: 1245, 1982. |
| p97 | 96.5 | K. E. Hellstrom et al., Monoclonal Antibodies and Cancer, loc. cit. p. 31. |
| Antigen T65 | T101 | Boehringer-Mannheim P.O. Box 50816 Indianapolis, IN 46250 |
| Ferritin | Antiferrin | Boehringer-Mannheim P.O. Box 50816 Indianapolis, IN 46250 |
| | R24 | W. G. Dippold et al., Proc. Natl. Acad. Sci. (USA), 77: 6114, 1980. |
| Neuroblastoma | P1 153/3 | R. H. Kennet and F. Gilbert, Science, 203: 1120, 1979. |
| | MIN 1 | J. T. Kemshead in Monoclonal Antibodies and Cancer, loc. cit. p. 49. |
| | UJ13A | Goldman et al., Pediatrics, 105: 252, 1984. |
| Glioma | BF7, GE2, CG12 | N. de Tribolet et al., in Monoclonal Antibodies and Cancer, loc. cit. p. 81. |
| Ganglioside | L6 | I. Hellstrom et al., Proc. Natl. Acad. Sci. (USA), 83: 7059 (1986); U.S. Pat. Nos. 4,906,562, issued March 6, 1990 and 4,935,495, issued June 19, 1990. |
| | Chimeric L6 | U.S. Ser. No. 07/759,707, filed September 12, 1991, equivalent to PCT Patent Publication, WO 88/03145, published May 5, 1988. |
| Lewis Y | BR64 | U.S. Ser. No. 07/289,635, filed December 22, 1988, now abandoned and U.S. Ser. No. 07/443,696, filed November 29, 1989 now U.S. Pat. No. 5,242,824 equivalent to European Patent Publication, EP A 0 375 562, published June 27, 1990. |
| fucosylated Lewis Y | BR96, Chimeric BR96 | U.S. Ser. No. 07/374,947, filed June 30, 1989 now abandoned and U.S. Ser. No. 07/544,246, filed June 26, 1990, now abandoned equivalent to PCT Patent Publication, WO 91/00295, published January 10, 1991. |
| Breast Cancer | B6.2, B72.3 | D. Colcher et al., in Monoclonal Antibodies and Cancer, loc. cit. p. 121. |
| Osteogenic Sarcoma | 791T/48, 791T/36 | M. J. Embleton, ibid, p. 181. |
| Leukemia | CALL 2 | C. T. Teng et al., Lancet, 1: 01, 1982. |
| | anti-idiotype | R.A. Miller et al., N. Engl. J. Med., 306: 517, 1982. |
| Ovarian Cancer | OC 125 | R. C. Bast et al., J. Clin. Invest., 68: 1331, 1981. |

-continued

| Antigen Site Recognized | Monoclonal Antibodies | Reference |
|---|---|---|
| Prostate Cancer | D83.21, P6.2, Turp-27 | J. J. Starling et al., in Monoclonal Antibodies and Cancer, loc. cit, p. 253. |
| Renal Cancer | A6H, D5D | P. H. Lange et al., Surgery, 98: 143, 1985. |

In the most preferred embodiment, the ligand containing conjugate is derived from chimeric antibody BR96, "ChiBR96", disclosed in U.S. Ser. No. 07/544,246, filed Jun. 26, 1990 now abandoned and which is equivalent to PCT Published Application, WO 91/00295, published Jan. 10, 1991. ChiBR96 is an internalizing murine/human chimeric antibody and is reactive, ad noted, with the fucosylated Lewis Y antigen expressed by human carcinoma cells such as those derived from breast, lung, colon, and ovarian carcinomas. The hybridoma expressing chimeric BR96 and identified as ChiBR96 was deposited on May 23, 1990, under the terms of the Budapest Treaty, with the American Type Culture Collection ("ATCC"), 12301 Parklawn Drive, Rockville, Md. 20852. Samples of this hybridoma are available under the accession number ATCC 10460. ChiBR96 is derived, in part, from its source parent, BR96. The hybridoma expressing BR96 was deposited, on Feb. 21, 1989, at the ATCC, under the terms of the Budapest Treaty and is available under the accession number HB 10036. The desired hybridoma is cultured and the resulting antibodies are isolated from the cell culture supernatant using standard techniques now well known in the art. See, e.g., "Monoclonal Hybridoma Antibodies: Techniques and Applications", Hurell (ed.) (CRC Press, 1982).

Thus, as used "immunoglobulin" or "antibody" encompasses within its meaning all of the immunoglobulin/antibody forms or constructions noted above.

Synthesis of the Compounds of the Invention

The linkers, drug/linkers, and conjugates of the invention can be made techniques taught herein, known in the art, or can be made via routine experimentation using as guidance the techniques taught herein and/or known in the art. The attachment of the drug to the linker is accomplished by reacting a nucleophilic atom of the drug (O, N or S) to an electrophilic atom (C, S, P) on either the self-immolating spacer or the carboxy terminus of the peptide. This is illustrated as follows:

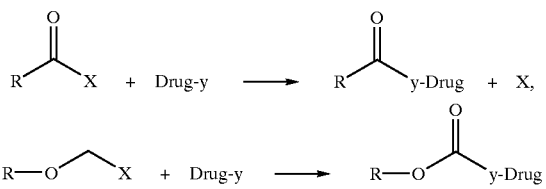

where:
X=leaving group such as Cl⁻, Br⁻, tosylate, N-hydroxysuccinimide
y=nucleophilic group such as OH, $NH_2$, SH, NH-lower alkyl
R=rest of linker.

Linkage to an aldehyde or ketone can be effected by having the aldehyde or ketone in the form of an enol or N-loweralkyl enamine. It is expected that on release of the free enamine, it will spontaneously hydrolyze to an aldehyde or ketone.

The following reaction schemes are illustrative preparative techiqes (compound numbers corrspond to Example numbers):

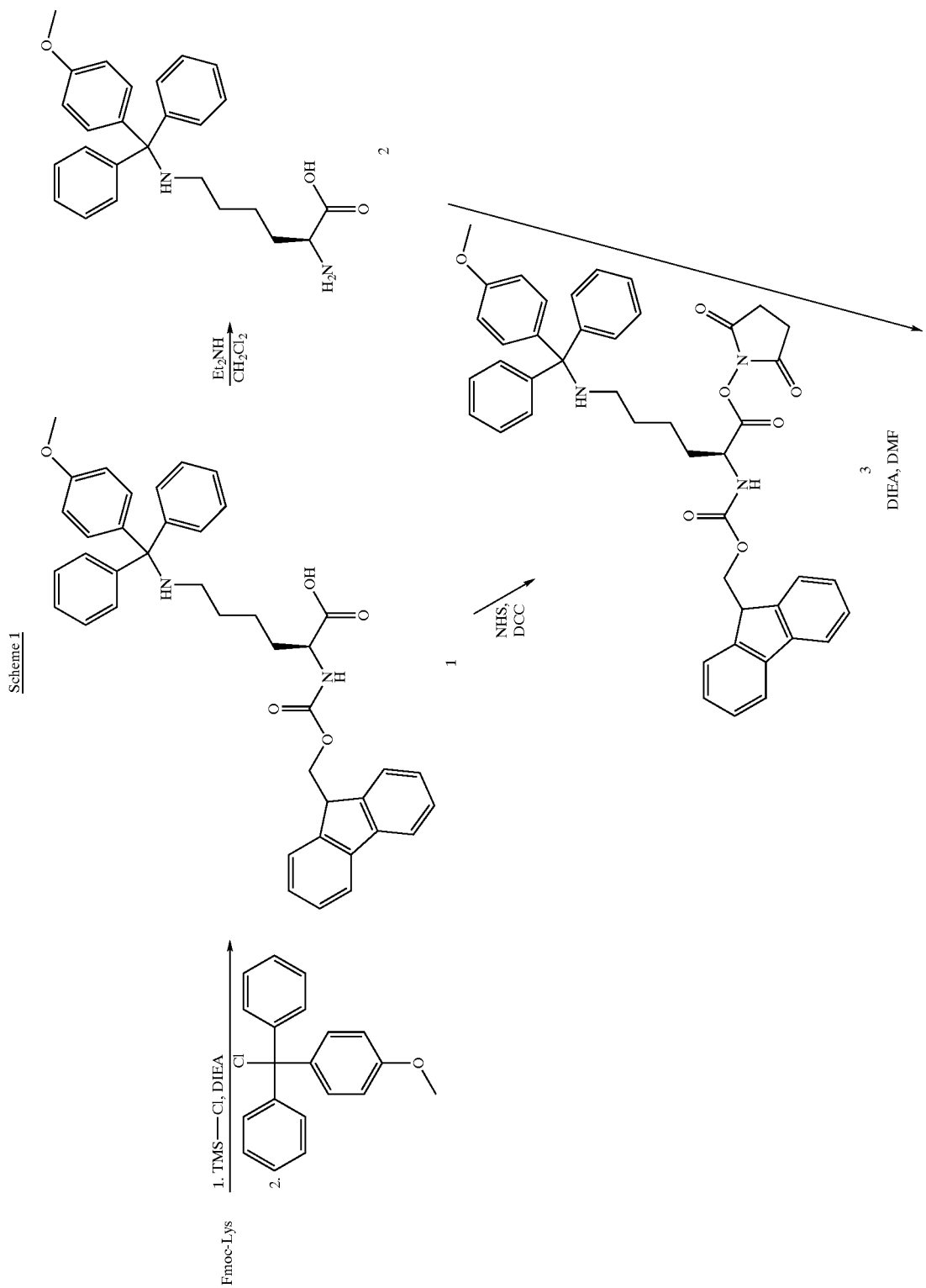

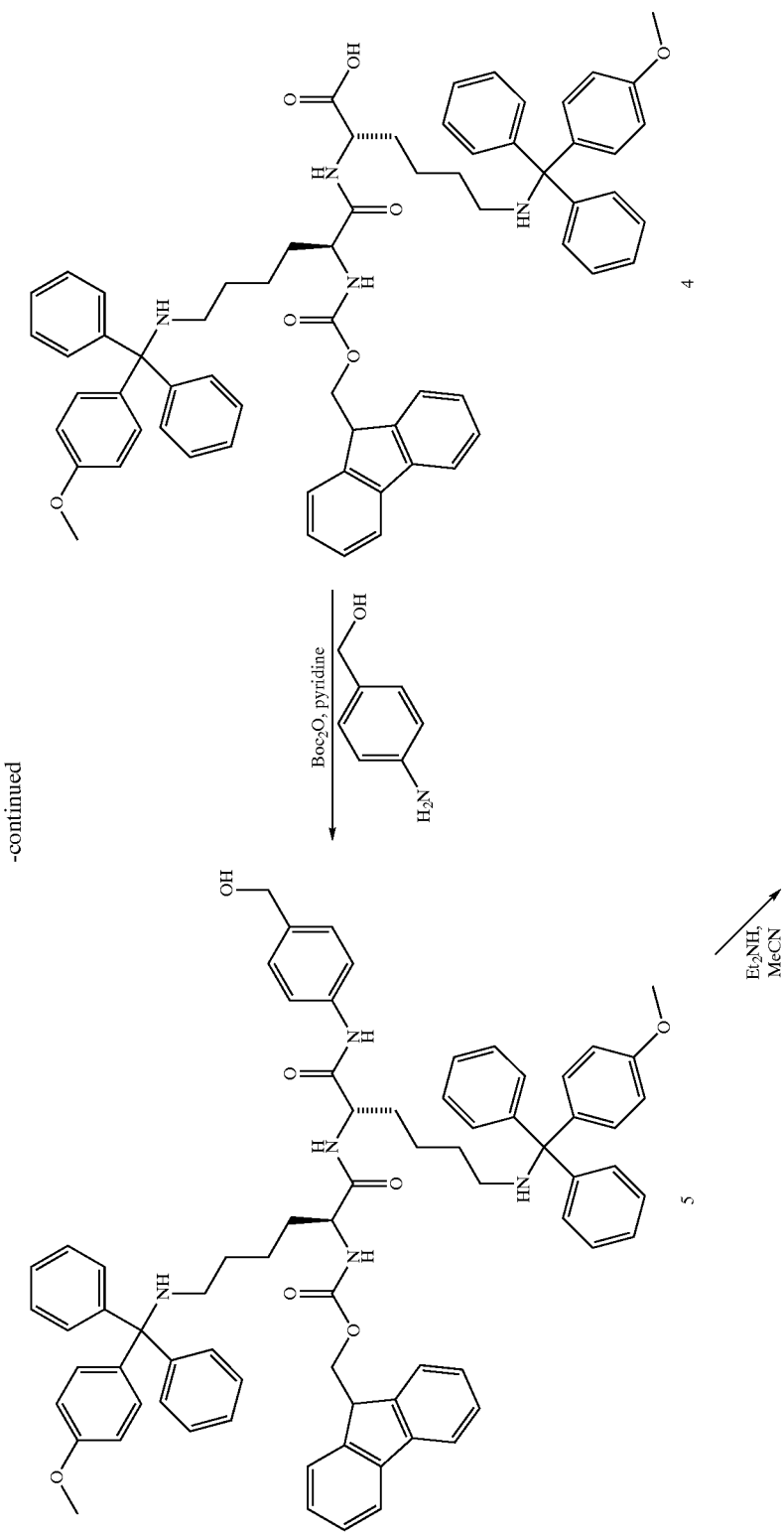

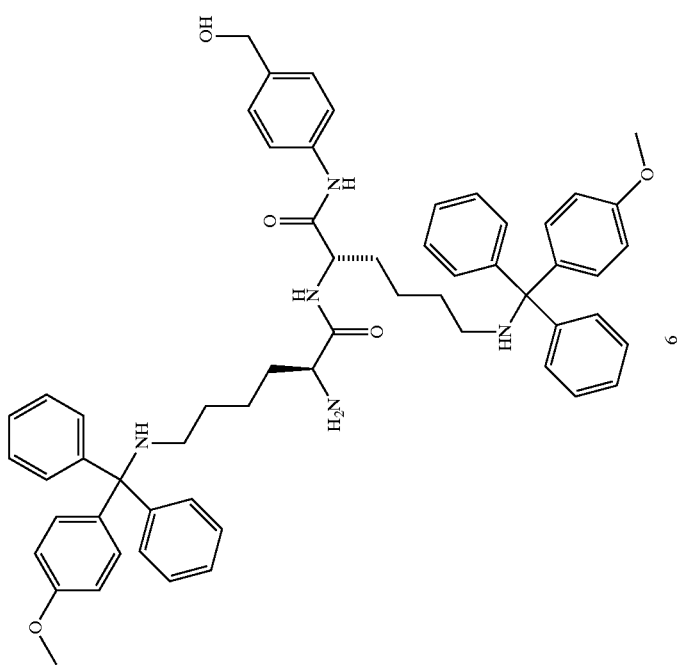
6

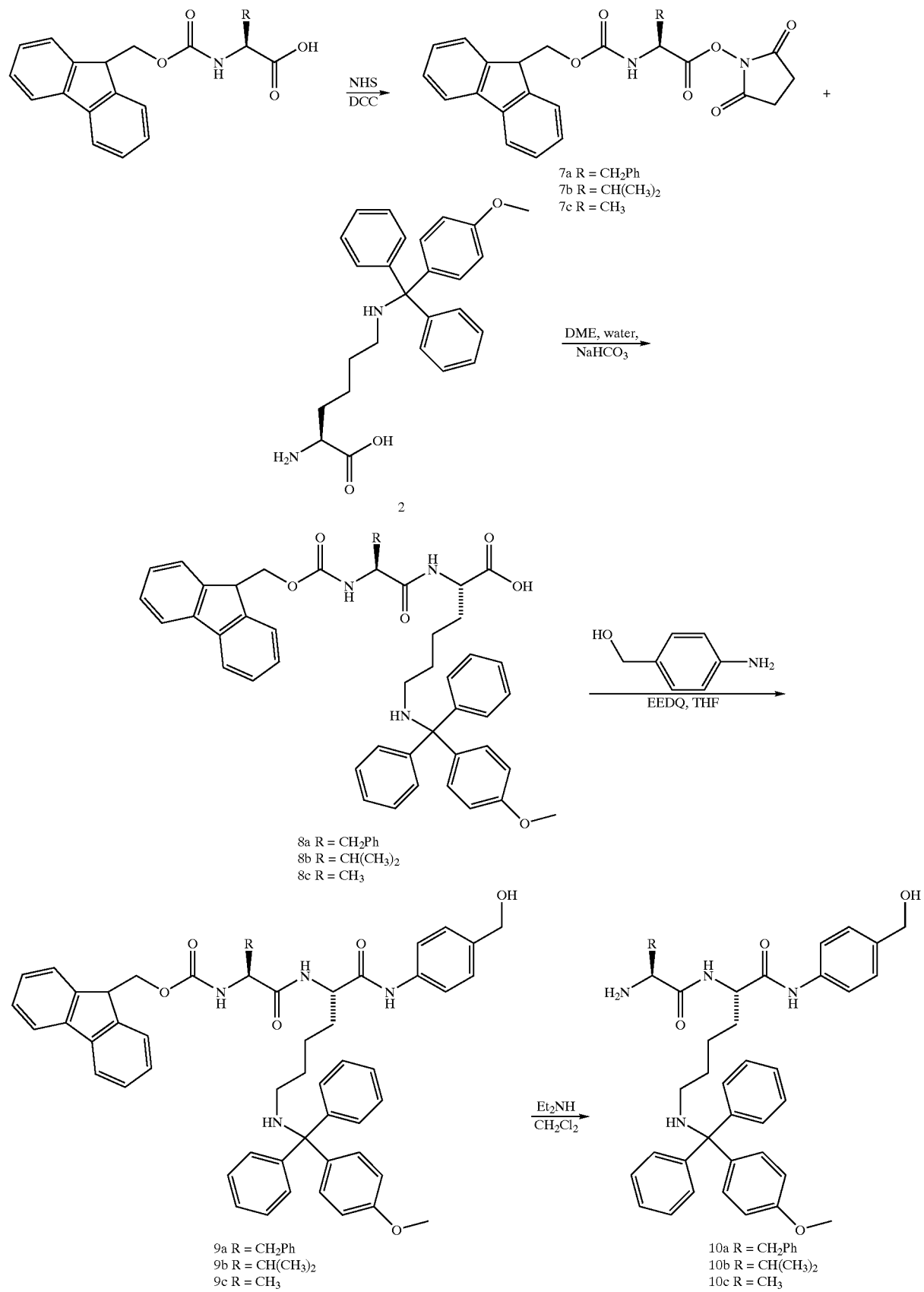

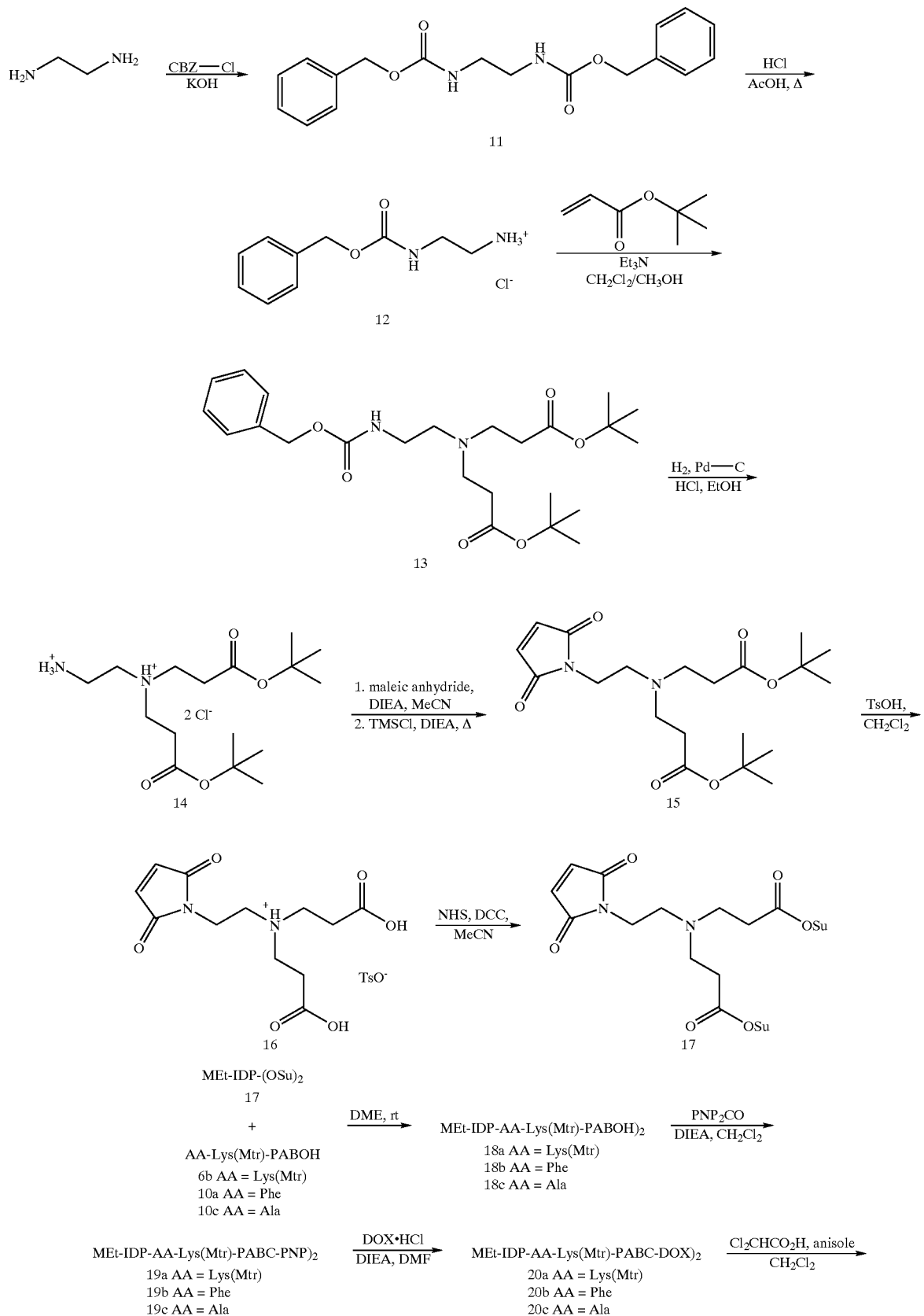

-continued
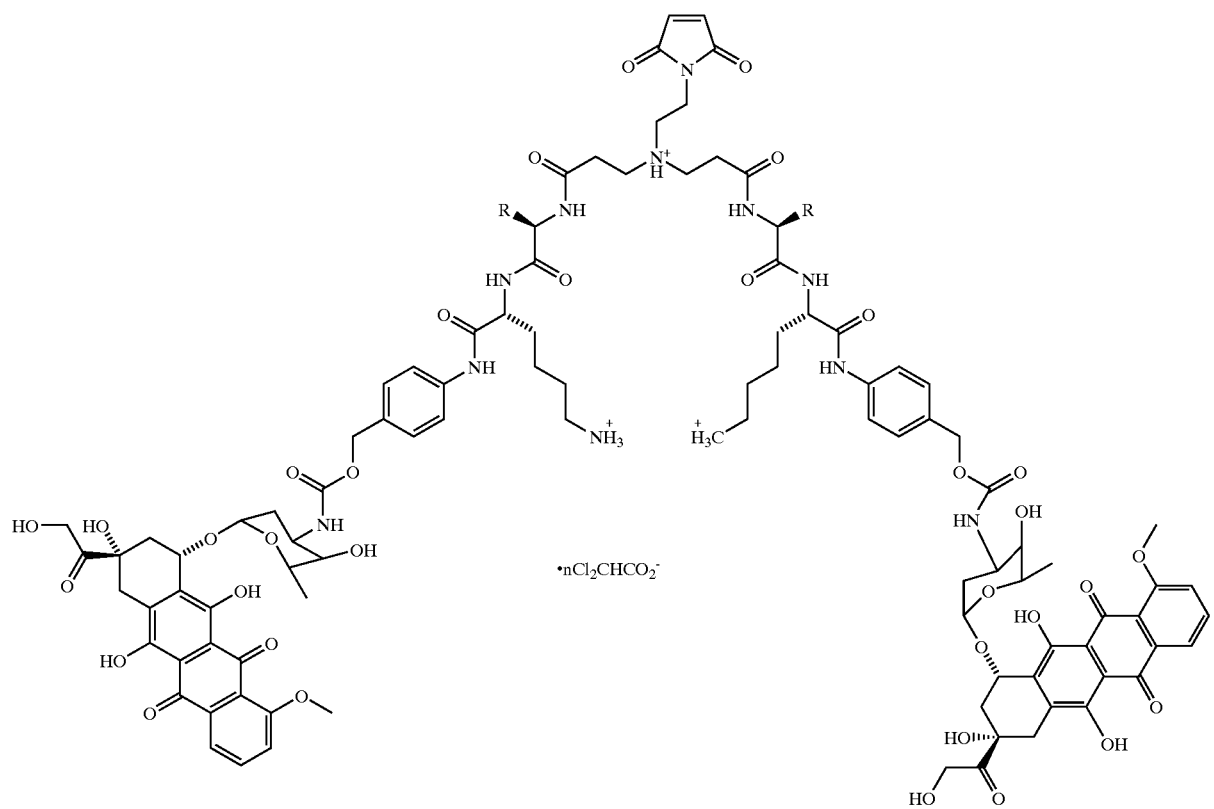
21a R = (CH$_2$)$_4$NH$_3^+$, n = 5
21b R = CH$_2$Ph, n = 3
21c R = CH(CH$_3$)$_2$, n = 3
Scheme 4
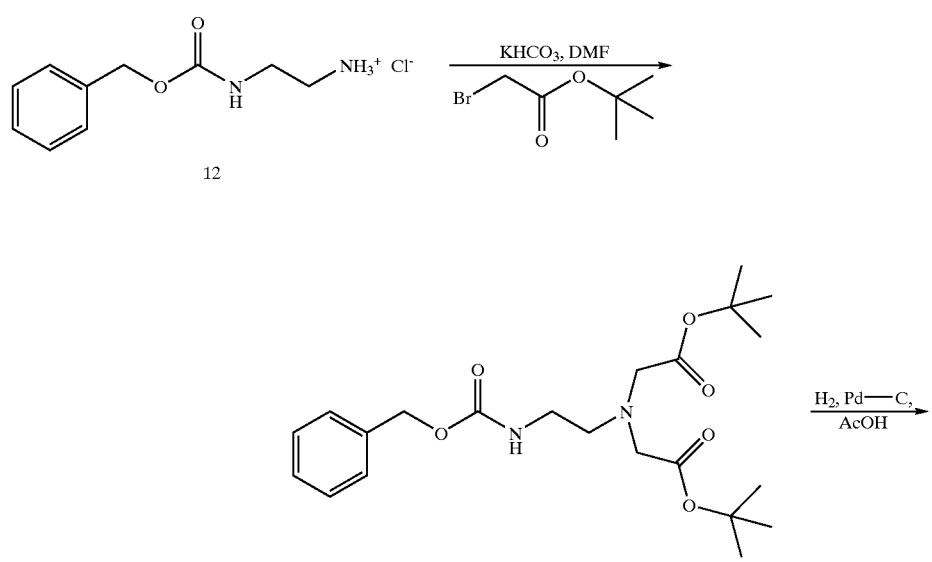

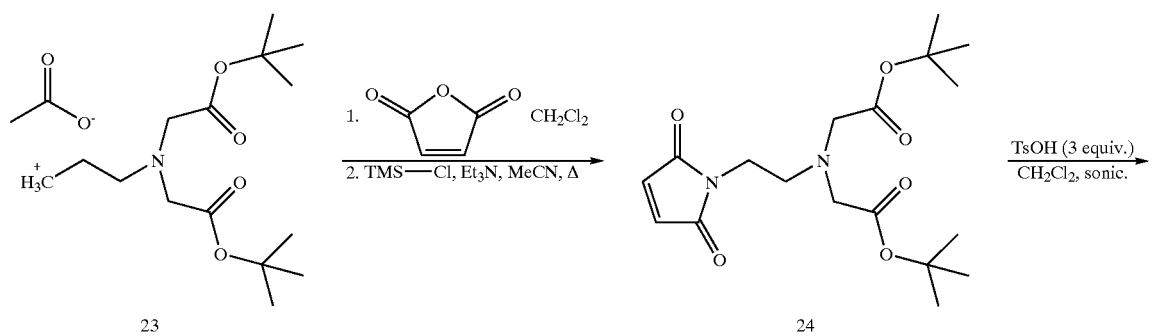
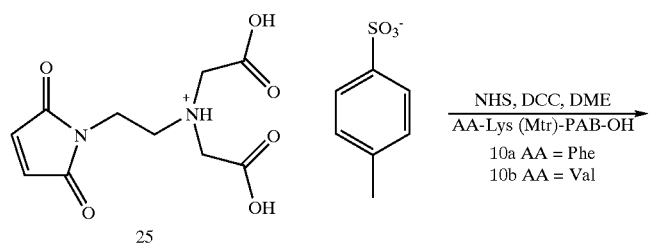
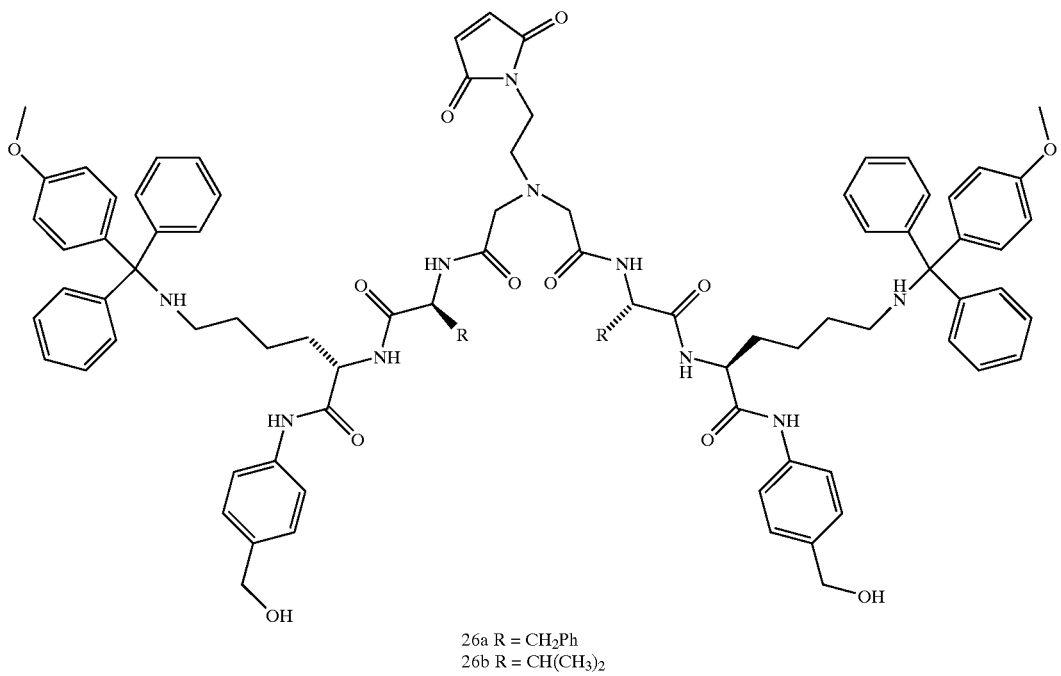
26a R = CH$_2$Ph
26b R = CH(CH$_3$)$_2$
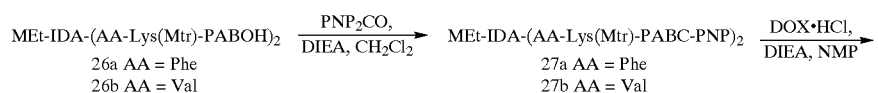
26a AA = Phe
26b AA = Val
27a AA = Phe
27b AA = Val
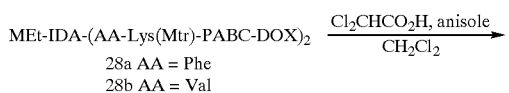
28a AA = Phe
28b AA = Val

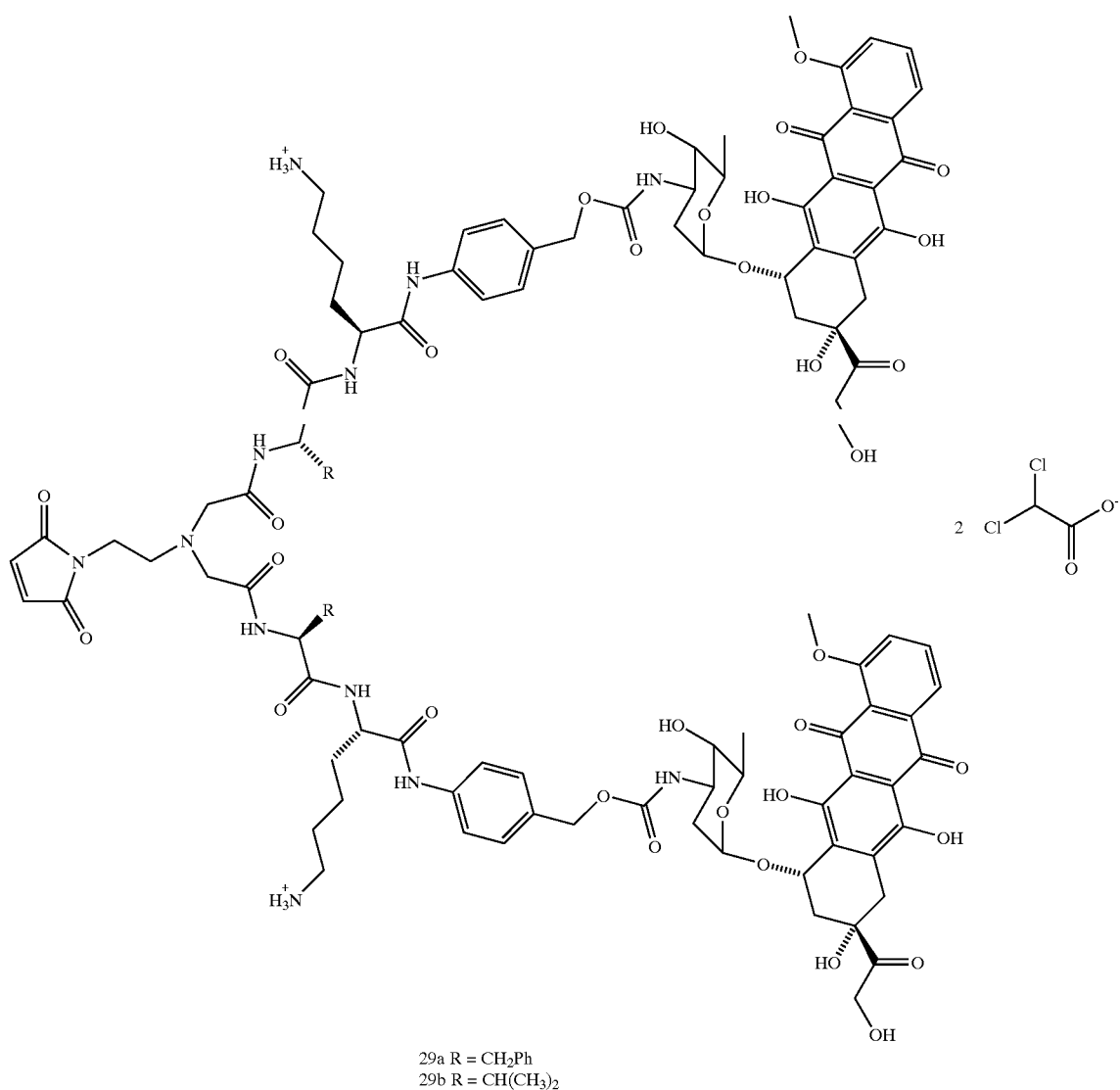
29a R = CH₂Ph
29b R = CH(CH₃)₂
Scheme 5
MEt-IDA-(Phe-Lys(Mtr)-PABC-PNP)₂ + MMC
27a
↓ HOBt, DIEA
  NMP, sieves
MEt-IDA-(Phe-Lys(Mtr)-PABC-MMC)₂
30
↓ ClCH₂CO₂H,
  anisole, CH₂Cl₂

-continued
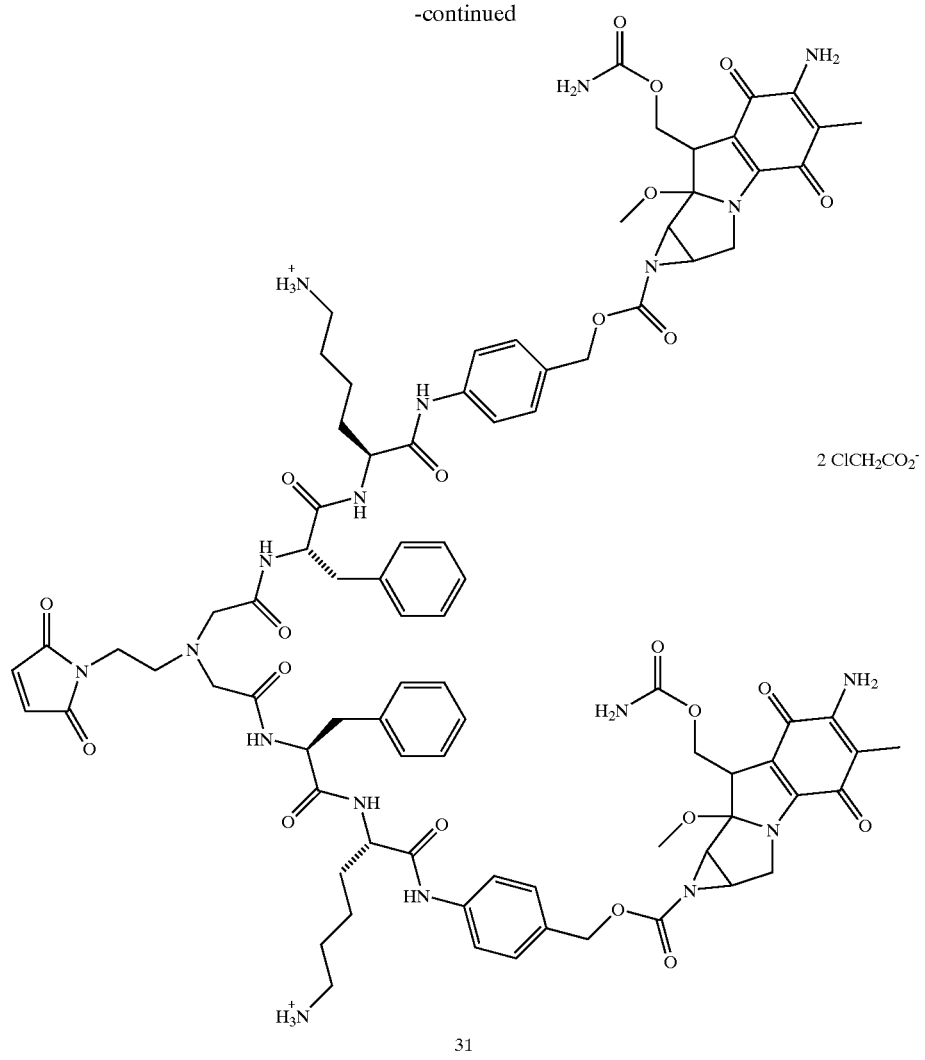
31
Scheme 6
Paclitaxel →(pyridine, CH$_2$Cl$_2$, trityl chloride reagent)
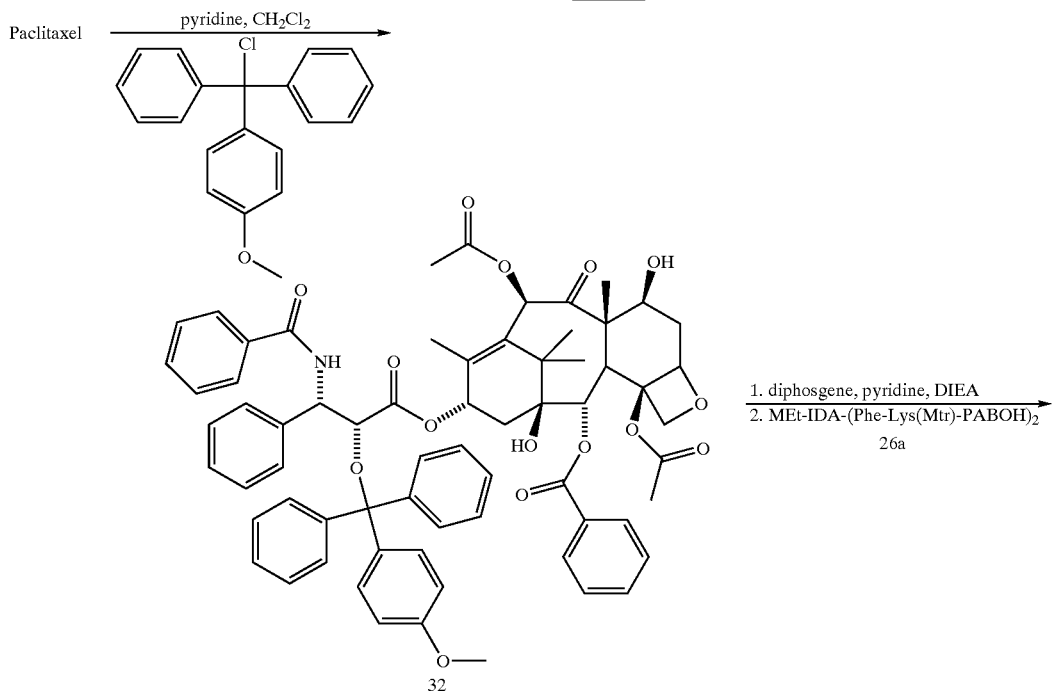
32
1. diphosgene, pyridine, DIEA
2. MEt-IDA-(Phe-Lys(Mtr)-PABOH)$_2$
   26a -continued
MEt-IDA-(Phe-Lys(Mtr)-PABC-7-Paclitaxel-2'-Mtr)₂
33
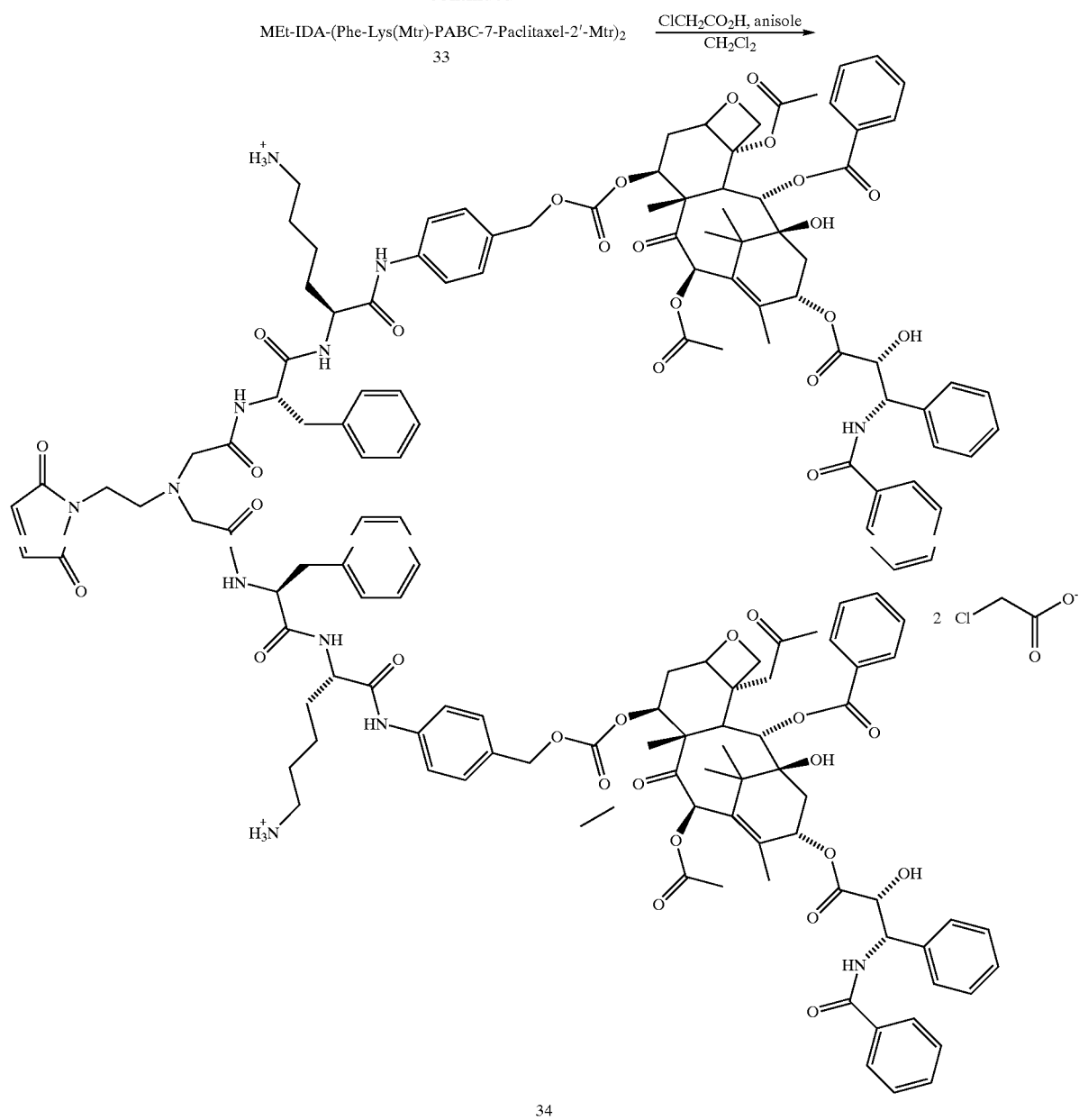
34
Scheme 7
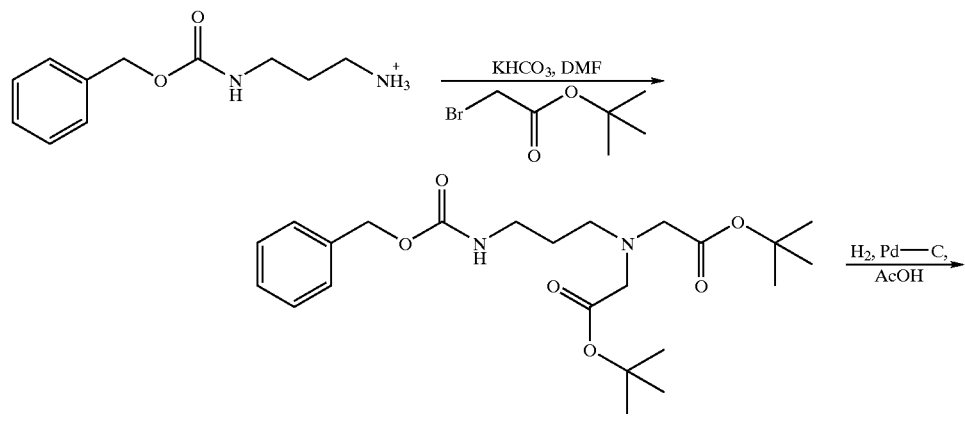
35

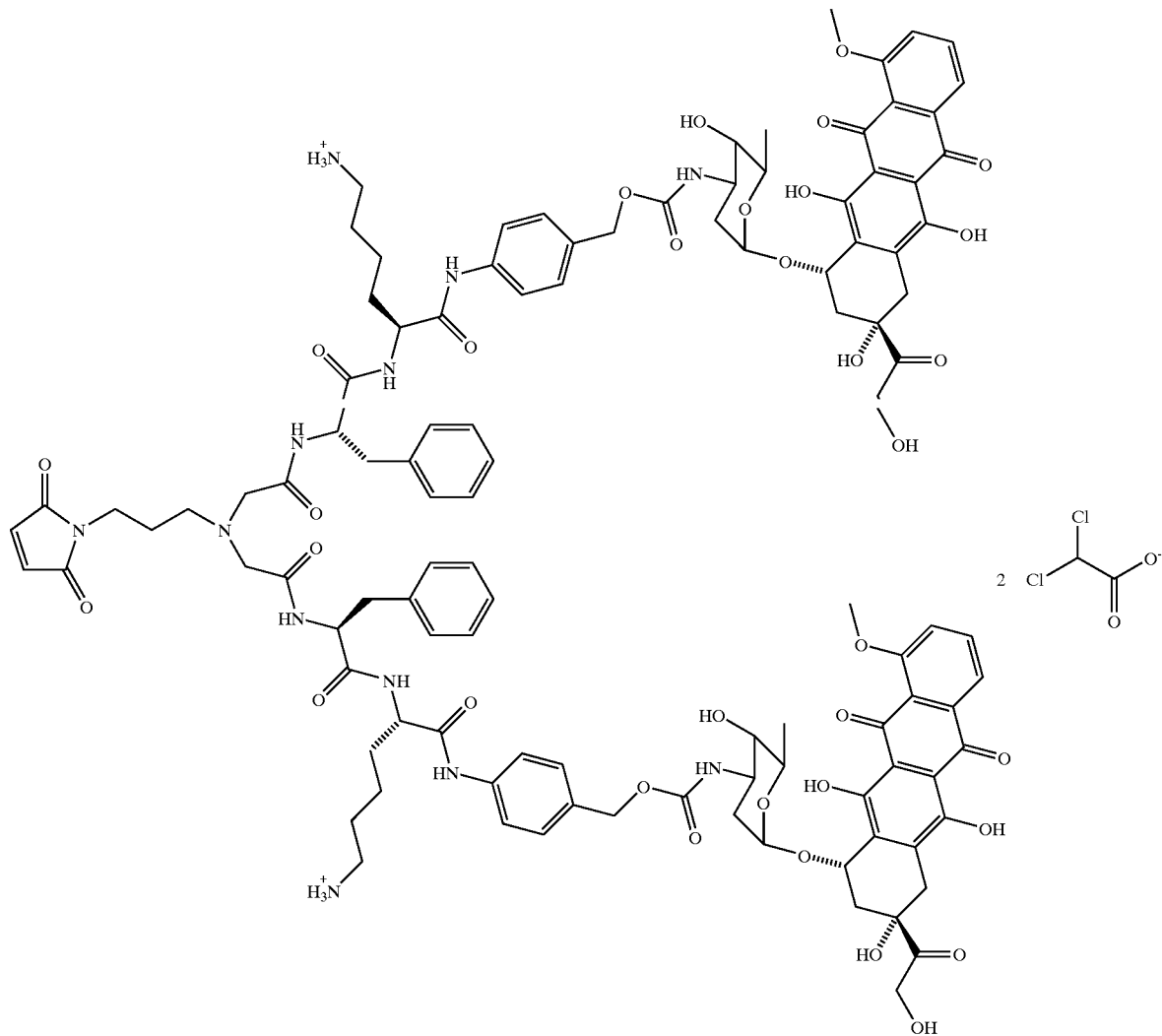

Scheme 8
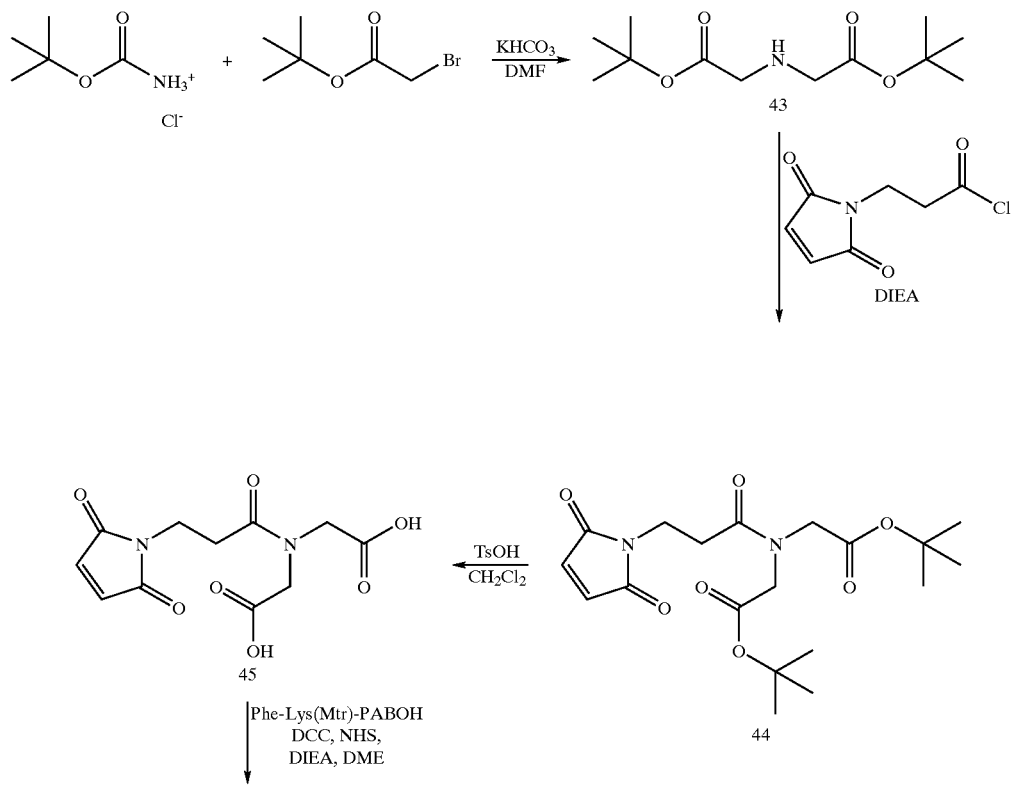
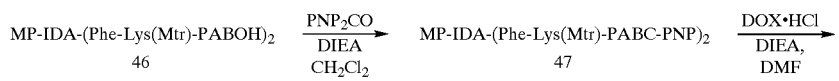
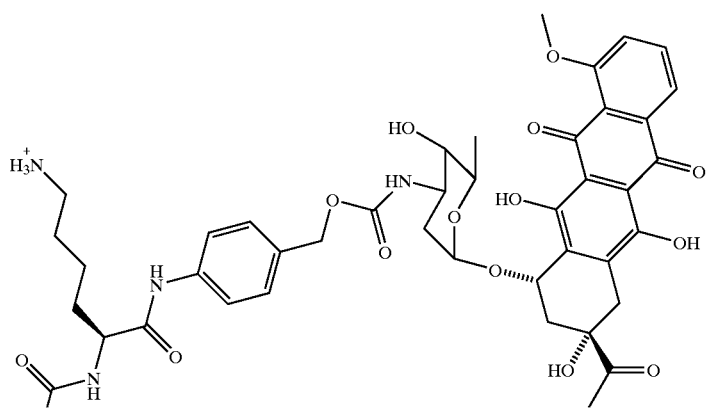

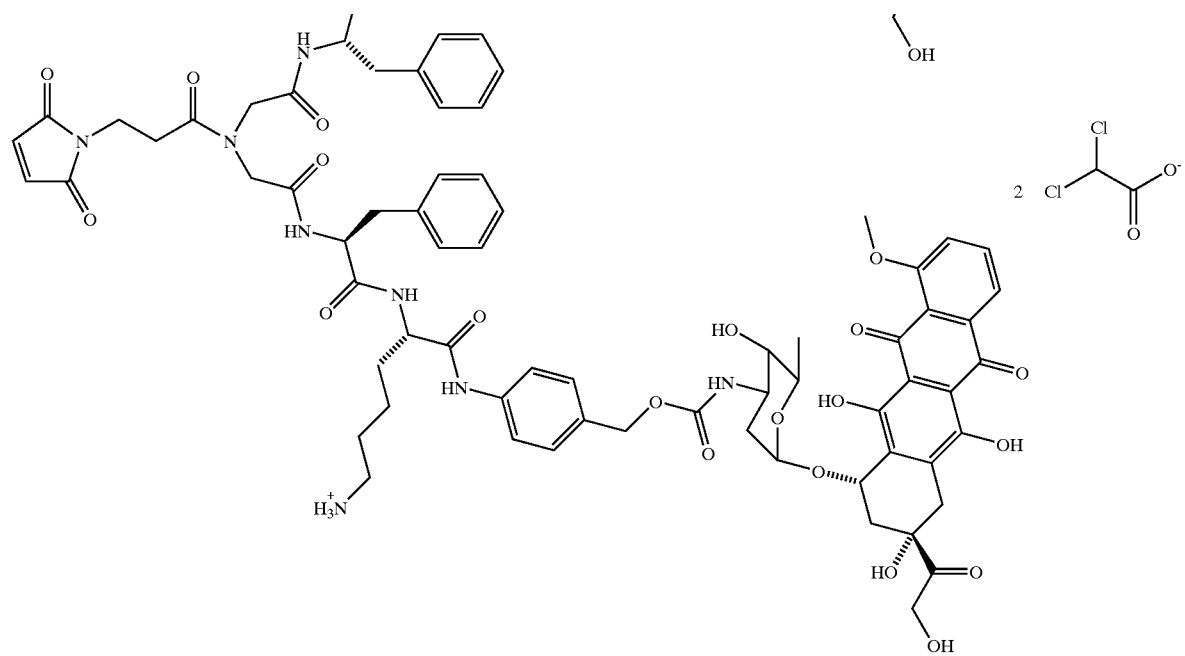
49
Scheme 9
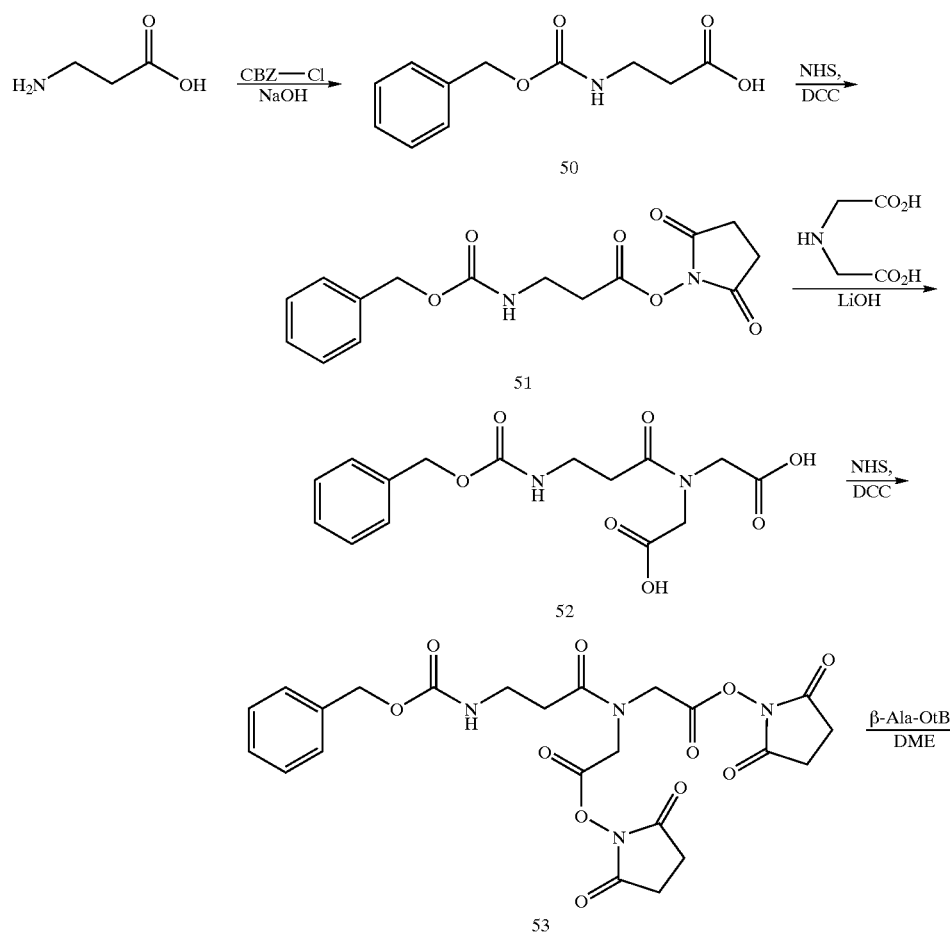

-continued
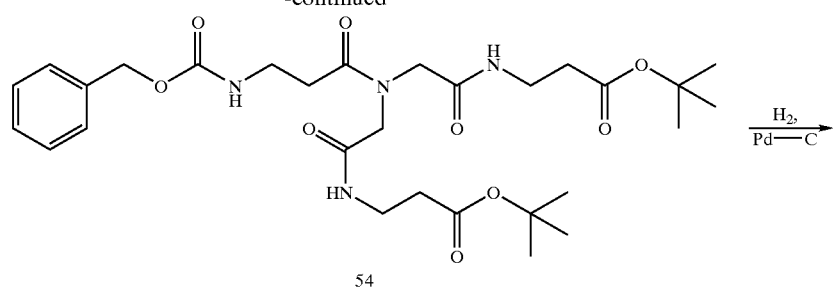
54
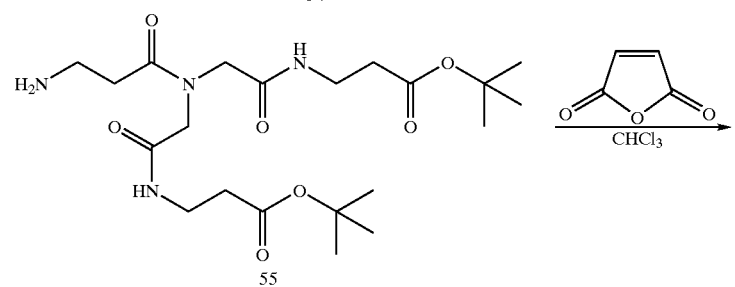
55
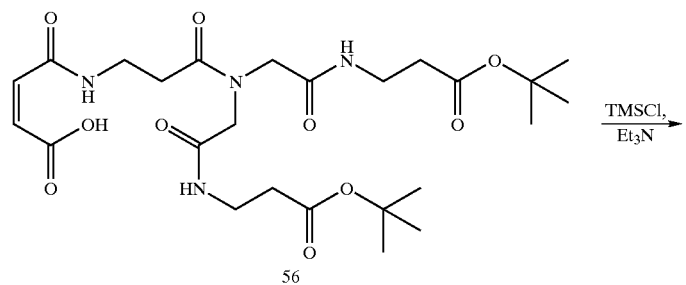
56
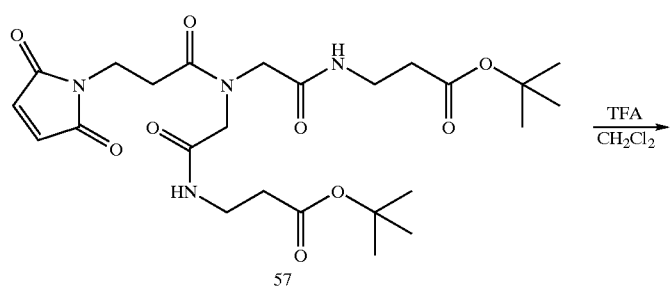
57
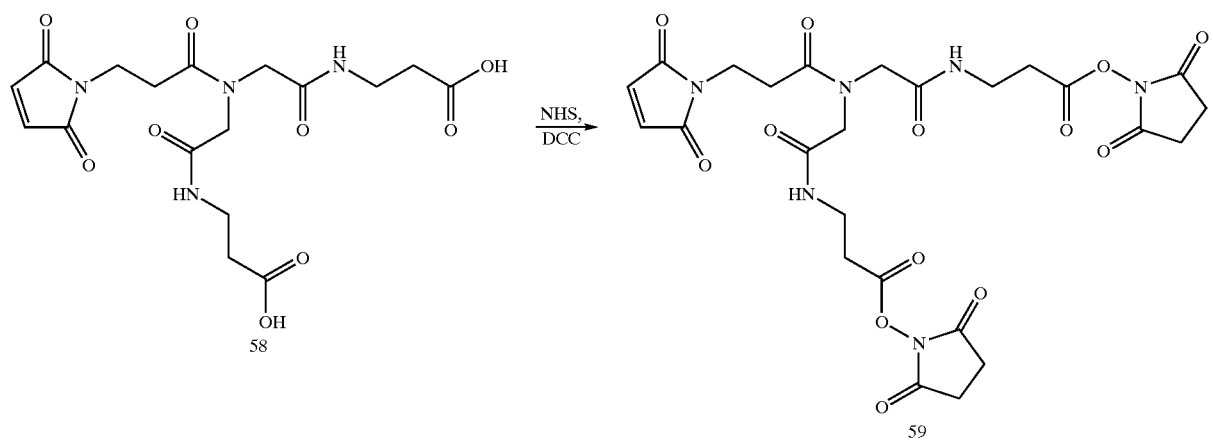
MP-IDA-(βAla-OSu)₂ + Phe-Lys(Mtr)-PABOH  →(DMF, rt)  MP-IDA-(βAla-Phe-Lys(Mtr)-PABOH)₂  →(PNP₂CO, DIEA, CH₂Cl₂)
59                    10a                                    60
MP-IDA-(βAla-Phe-Lys(Mtr)-PABC-PNP)₂  →(DOX·HCl, DIEA, DMF)  MP-IDA-(βAla-Phe-Lys(Mtr)-PABC-DOX)₂  →(Cl₂CHCO₂H, anisole, CH₂Cl₂)
61                                                              62

-continued
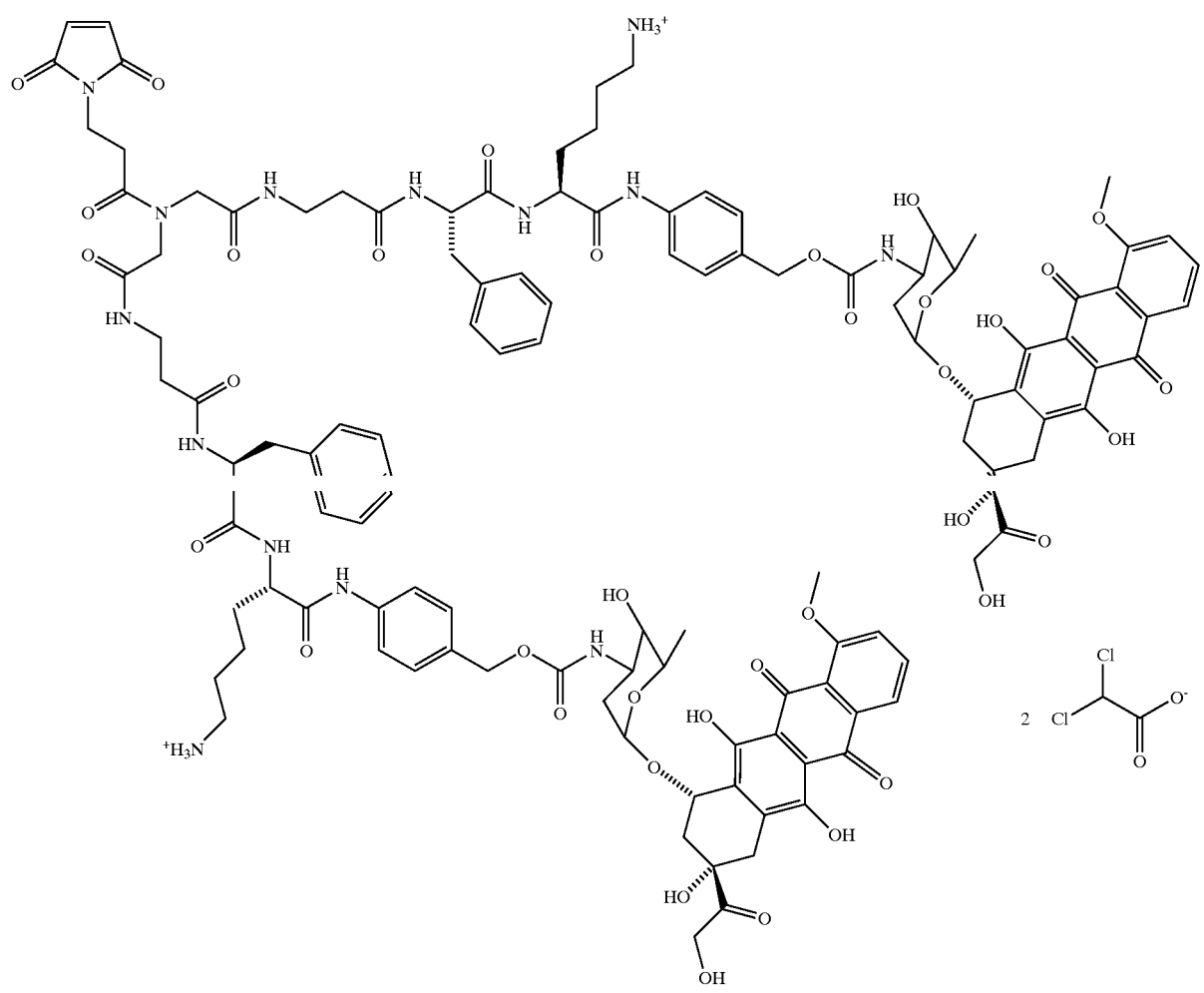
63
Scheme 10
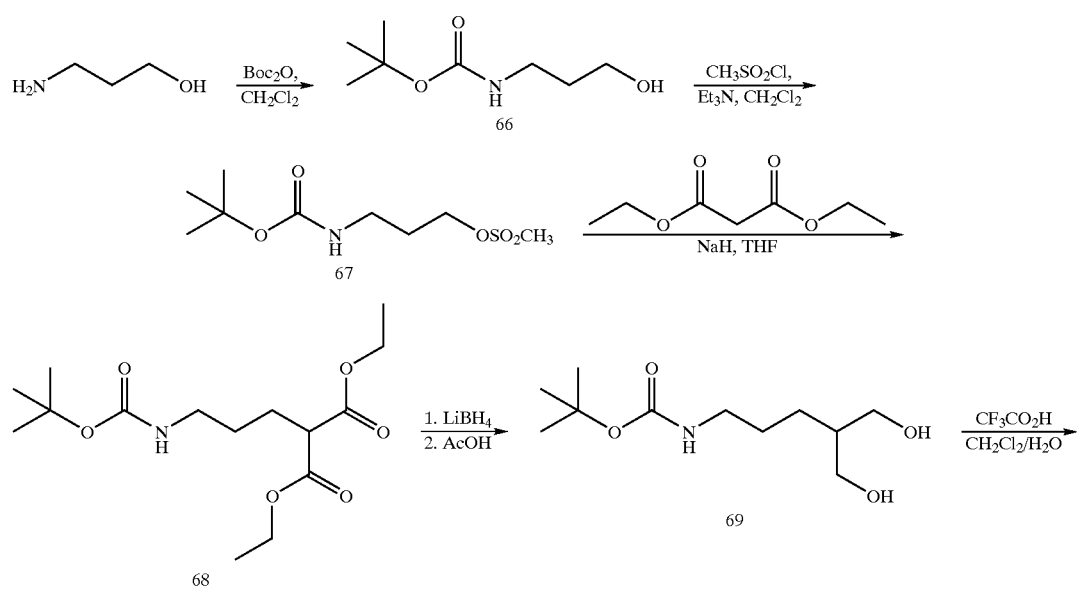

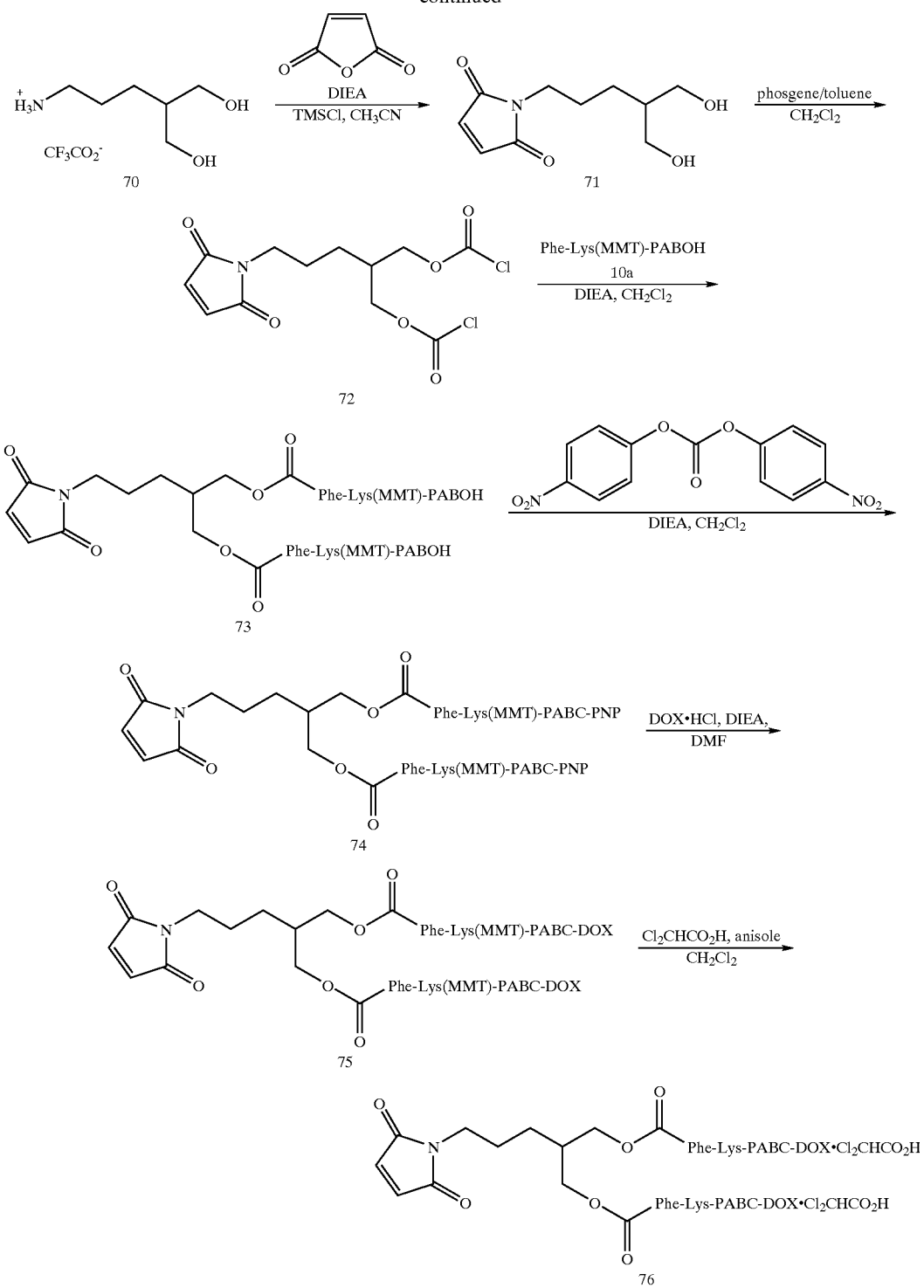
Scheme 11
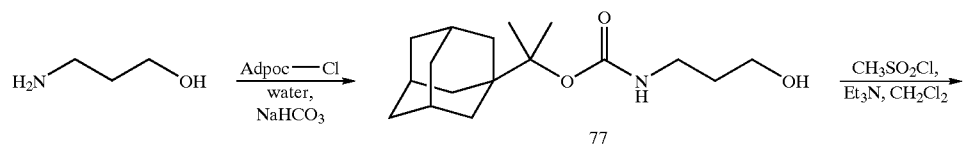

-continued
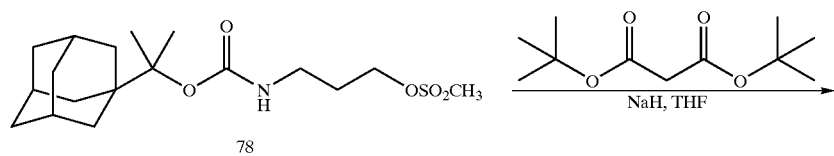
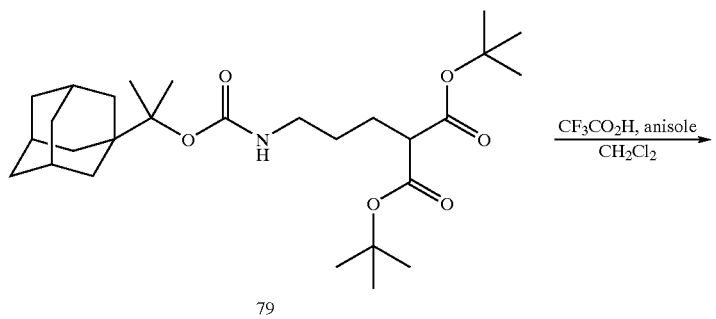
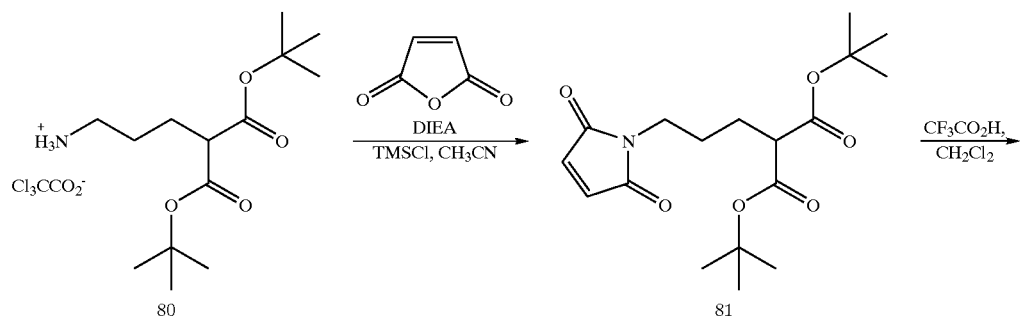
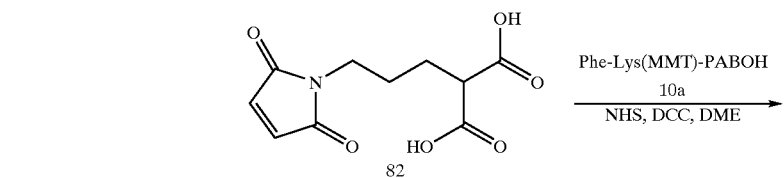
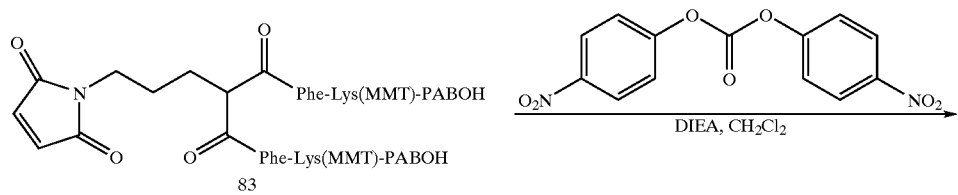
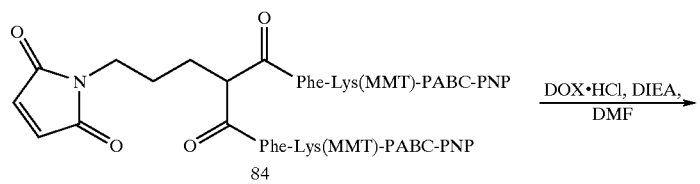
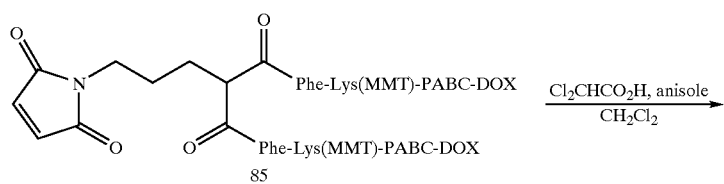

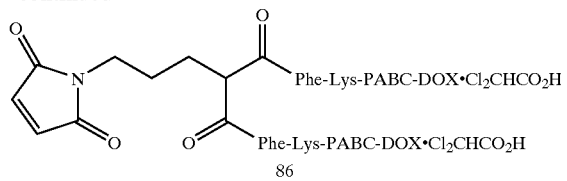
Scheme 12
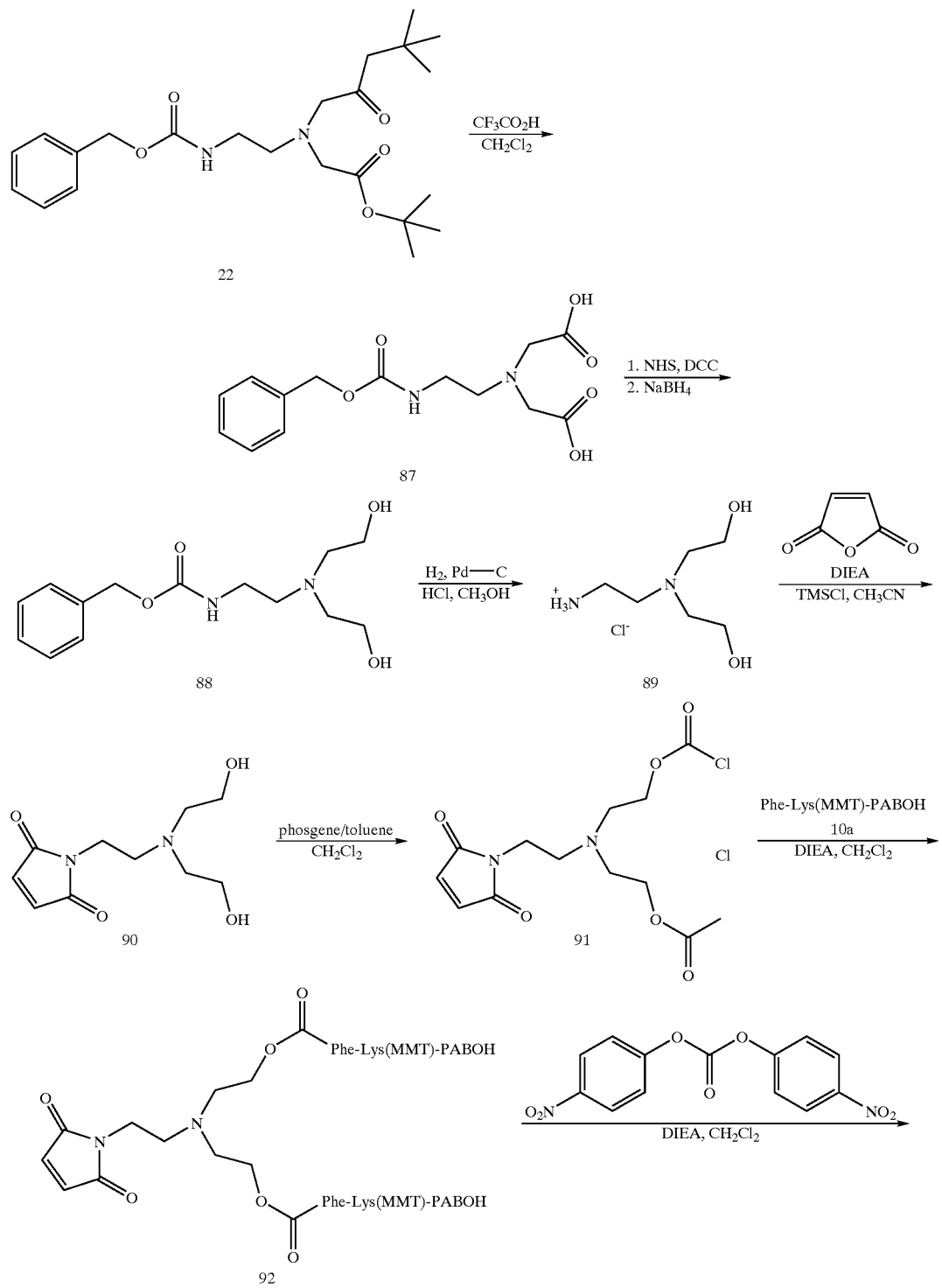

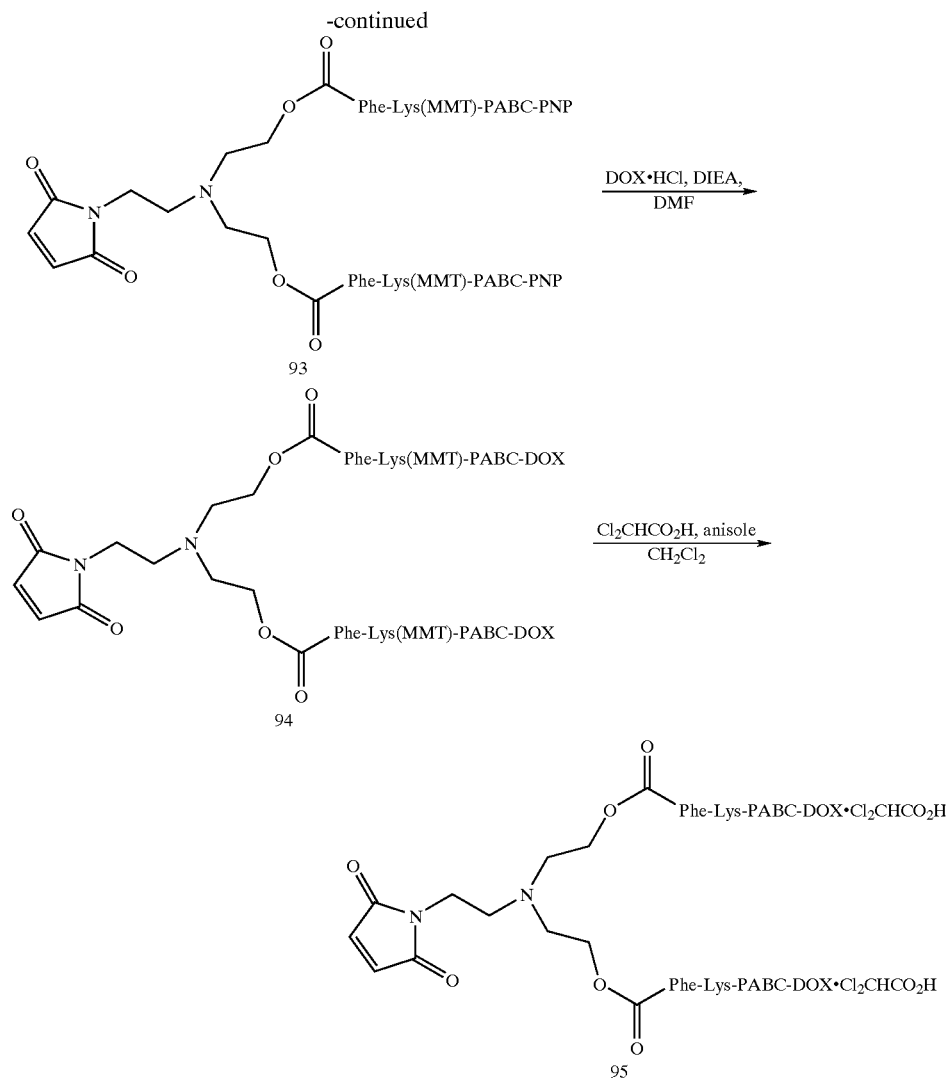

The following examples are to illustrate the invention but should not be construed as a limitation thereon.

EXAMPLE 1

Fmoc-Lys(Mtr)

A stirred suspension of Fmoc-Lys hydrochloride (23.78 g, 56.42 mmol) in dry methylene chloride (250 mL) under argon at rt was treated with trimethylsilyl chloride (15 mL, 2.1 equiv) and DIEA (10.3 mL, 1.05 equiv). The mixture was heated at reflux for 1 h, during which time it became homogeneous, and then cooled to 0° C. DIEA (31 mL, 3.1 equiv) was added, followed by p-anisyldiphenylmethyl chloride (18.29 g, 1.05 equiv). The reaction was stirred at rt for 14 h. The solvent was evaporated and the residue partitioned between ethyl acetate and pH 5 buffer (0.05 M biphthalate). The organic phase was washed with more pH 5 buffer, water and brine, dried over sodium sulfate and evaporated to give a pale-yellow foam (34.71 g, 96%). $^1$H-NMR (CDCl$_3$) δ 1.26 and 1.68 (m, 2H and 4H), 2.45 (m, 2H), 3.71 (s, 3H), 4.05–4.40 (m, 4H), 6.81 (d, 2H), 7.15–7.77 (m, 20H). MS (FAB) 641 (MH)$^+$, 663 (M+Na)$^+$, 679 (M+K)$^+$. HRMS Calcd: 641.3015. Found: 641.3001.

EXAMPLE 2

Lys(Mtr)

Fmoc-Lys(Mtr) 1 (5.25 g, 8.19 mmol) in 1:1 methylene chloride/acetonitrile (80 mL) at rt was treated with diethylamine (80 mL). After 1.5 h the solvents were evaporated. The residue was flushed with acetonitrile (2×50 mL) at 60° C., and then triturated with ether (80 mL). The resulting solid was collected by filtration, washed with ether, and then dissolved as far as possible in 1:1 methylene chloride/methanol. Some solid byproduct was removed by filtration and the filtrate was concentrated invacuo. The resulting light tan solid was dried in vacuo for 4 h (3.2221 g, 94%). $^1$H-NMR (DMSO-d$_6$) δ 1.34, 1.57 and 1.72 (m, 6H), 2.05 (m, 2H), 3.38 (m, 1H), 3.68 (s, 3H), 3.71 (d, 2H), 7.03–7.40 (m, 12H). MS (FAB) 419.2 (MH)$^+$, 441.4 (M+Na)$^+$, 457.4 (M+K)$^+$. MS (FAB) 419.2 (MH)$^+$, 441.4 (M+Na)$^+$, 457.4 (M+K)$^+$.

EXAMPLE 3

Fmoc-Lys(Mtr)-OSu

A stirred solution of Fmoc- Lys(Mtr) 2 (5.5567 9, 8.672 mmol) and N-hydroxysuccinimide (1.0978 g, 1.1 equiv) in DME (100 mL) at 0° C. was treated with 0.5M DCC in methylene chloride (19.1 mL, 1.01 equiv). The mixture was gradually warmed to rt. after 14 h the solid DCU was filtered off and the filtrate evaporated to dryness. The crude active ester was used without further purification. $^1$H-NMR (CDCl$_3$) δ 1.52, 1.73 and 1.92 (m, 6H), 2.14 (t, 2H), 2.79 (brs, 4H), 3.75 (s, 3H), 4.21 (t, 1H), 4.42 (d, 2H), 4.71 (m, 1H), 5.40 (d, 1H), 6.79 (d, 2H), 7.10–7.76 (m, 20H).

EXAMPLE 4

Fmoc-Lys(Mtr)-Lys(Mtr)

A stirred solution of Fmoc-Lys(Mtr)-OSu 3 (ca 8.672 mmol) and Lys(Mtr) 2 (3.6294 g, 1 equiv) in DMF (70 mL) at rt was treated with DIEA (4.5 mL, 3 equiv). After 4 h the mixture was diluted with ethyl acetate (250 mL). The solution was washed with pH 4 buffer (0.05M biphthalate) (2x), water and brine, dried over sodium sulfate and evaporated the residue was flushed with methylene chloride (400 mL) to give a pale-yellow foam which was carried on without further purification. $^1$H-NMR (CDCl$_3$/CD$_3$OD) δ 1.10–1.85 (m, 12H), 2.22 (m, 4H), 3.70 (m, 6H), 4.21 (m, 5H), 6.76 (m, 4H), 7.00–7.75 (m, 32H). MS (ESI) 1041. 6 (MH)$^+$.

EXAMPLE 5

Fmoc-Lys(Mtr)-Lys(Mtr)-PABOH

A stirred solution of Fmoc-Lys(Mtr)-Lys(Mtr) 4 (ca 8.672 mmol) and di-t-butydicarbonate (2.8390 g, 1.5 equiv) in methylene chloride (100 mL) at rt was treat ed with pyridine (0.736 mL, 1.05 equiv). After 20 mn p-aminobenzyl alcohol (1.6020 g, 1.5 equiv) was added. Stirring was continued for 16 h and then the solvent wa s evaporated and the residue dried in vacuo for 2 h. The crude product was carried on without further purification. $^1$H-NMR (CDCl$_3$/CD$_3$OD) δ 1.00–1.75 (m, 12H), 2.09 (m, 4H), 3.73 (m, 6H), 4.14 (m, 3H), 4.39 (m, 2H), 4.58 (m, 2H), 6.76 (m, 4H), 7.05–7.75 (36H). MS (ESI) 1146.6 (MH)$^+$. Anal. Calcd for C$_{74}$H$_{75}$N$_5$O$_7$-2H$_2$O: C-75.17, H-6.73, N-5.92. Found: C-74.89, H-6.37, N-5.75.

EXAMPLE 6

Lys(Mtr)-Lys(Mtr)-PABOH

Fmoc-Lys(Mtr)-Lys(Mtr)-PABOH 5 (ca 8.672 mmol) in acetonitrile (100 mL) at rt was treated with diethylamine (75 mL). After 2 h the solvents were removed on the rotovap at 40° C. and the residue dried in vacuo for 1 h and then dissolved as far as possible in methylene chloride (150 mL). The solid was removed by filtration and the filtrate concentrated in vacuo. The residue was chromatographed on silica, eluting with 1) 2.5%, 2) 3%, and 3.5% methanol/methylene chloride, to give the product as a colorless foam (2.8403 g, 35% (4 steps)). $^1$H-NMR (CDCl$_3$) δ 1.42 and 1.78 (m, 12H), 2.12 (brt, 4H), 3.32 (m, 1H), 3.75 (s, 3H), 3.79 (s, 3H), 4.44 (m, 1H), 4.57 (s, 2H), 6.77 (ABq, 4H), 7.10–7.70 (m, 28H), 7.91 (d, 1H), 9.09 (s, 1H). MS (ESI) 924.5 (MH)$^+$. Anal. Calcd for C$_{59}$H$_{65}$N$_5$O$_5$—H$_2$O: C-75.21, H-7.17, N-7.43. Found: C-75.37, H-6.96, N-7.24.

EXAMPLE 7a

Fmoc-Phe-OSu

Fmoc-Phe (5.1043 g, 13.17 mmol) and NHS (1.592 g, 1.05 equiv) in methylene chloride (100 mL) at OOC were treated with DCC (2.854 g, 1.05 equiv). The ice bath was allowed to warm to rt and the mixture was stirred for 14 h. DCU was removed by filtration and the filtrate was evaporated. The resulting crude product, a colorless glass, was used without further purification.

EXAMPLE 7b

Fmoc-Val-OSu 7b

This was prepared from Fmoc-Val (7.02 g, 20.7 mmol) as described above for 7a.

EXAMPLE 7c

Fmoc-Ala-OSu

This was prepared from Fmoc-Ala (5.0414 g, 15.31 mmol) as described above for 7a.

EXAMPLE 8a

Fmoc-Phe-Lys(Mtr)

A suspension of Lys(Mtr) 2 (4.686 g, 11.20 mmol) and NaHCO$_3$ (941.0 mg, 1 equiv) in water (100 mL) and DME (50 mL) was treated with a solution of Fmoc-Phe-OSu 7a (11.20 mmol) in DME (50 mL). THF (25 mL) was then added to aid solubility. The mixture was stirred at rt for 2 days and then as much DME as possible was removed on the rotovap (bath at 30° C.). The resulting gummy suspension was partitioned between ethyl acetate and pH 5 buffer. The organic phase was washed with water and brine, dried and evaporated to give a pale yellow foam. This was flushed with methylene chloride (100 mL). TLC showed the product to be satisfactorily pure and it was carried on without further purification (8.559 g, 97%). $^1$H-NMR (CDCl$_3$/CD$_3$OD) δ 1.10–1.93 (m, 6H), 2.31 (t, 2H), 3.00 (m, 2H), 3.71 (s, 3H), 4.02–4.48 (m, 5H), 6.79 (d, 2H), 7.00–7.75 (m, 25H). MS (FAB) 788.2 (MH)$^+$, 810.4 (M+Na)$^+$, 826 (M+K)$^+$. Anal. Calcd for C$_{50}$H$_{49}$N$_3$O$_6$—H$_2$O: C-74.51, H-6.38, N-5.21. Found: C-74.17, H-6.57, N-5.41.

EXAMPLE 8b

Fmoc-Val-Lys(Mtr)

This was prepared from Fmoc-Val-OSu 7b (20.7 mmol) and Lys(Mtr) 2 (9.09 g, 1.05 equiv) as described above for 8a (15.28 g, 100%). $^1$H-NMR (CDCl$_3$/CD$_3$OD) δ 0.85 (m, 6H), 1.20 (m, 2H), 1.59 (m, 4H), 1.99 (m, 1H), 2.41 (m, 2H), 3.71 (s, 3H), 4.21 (m, 5H), 6.78 (d, 2H), 7.29 (m, 16H), 7.51 (brt, 2H), 7.71 (d, 2H). MS (FAB) 740 (MH)$^+$, 762 (M+Na)$^+$. HRMS Calcd: 740.3700. Found: 740.3712.

EXAMPLE 8c

Fmoc-Ala-Lys(Mtr)

A solution of Fmoc-Ala-OSu 7c (15.31 mmol) in DME (100 mL) was added to a stirred solution of Lys(Mtr) 2 (6.4080 g, 1 equiv) and potassium bicarbonate (1.5331 mg, 1 equiv) in 2:1 water/DME (150 mL). After 16 h the DME was removed in vacuo and the resulting suspension was treated with citric acid (3.22 g, 1.1 equiv) in water (25 mL). The mixture was extracted with ethyl acetate. The organic phase was washed with water (2x) and brine, dried over sodium sulfate, and concentrated in vacuo, giving a yellow foam which was carried on without further purification. $^1$H-NMR (CDCl$_3$/CD$_3$OD) δ 1.25 (m, 2H), 1.32 (d, 3H), 1.57 (m, 3H), 1.73 (m, 1H), 2.41 (brt, 2H), 3.72 (s, 3H), 4.14 (m, 1H), 4.29 (m, 4H), 6.79 (d, 2H), 7.22 (m, 16H), 7.38 (d, 4H), 7.52 (m, 2H), 7.72 (d, 2H). MS (FAB) 712.2 (MH)$^+$, 750.2 (M+K)$^+$.

EXAMPLE 9a

Fmoc-Phe-Lys(Mtr)-PAB-OH

A stirred solution of Fmoc-Phe-Lys(Mtr) 8a (7.728 g, 9.808 mmol) and p-aminobenzyl alcohol (1.450 g, 1.2 equiv) in methylene chloride (100 mL) at rt was treated with EEDQ (3.640 g, 1.5 equiv). After 20 h the solvent was evaporated (water bath at 30° C.). The solid residue was triturated with ether (200 mL) and the resulting suspension sonicated for 15 min and left to stand at rt for 2 h. The resulting solid was collected by filtration, washed well with ether, and dried in vacuo (7.6140 g, 87%). $^1$H-NMR (CDCl$_3$/ CD$_3$OD) δ 0.98–1.91 (m, 6H), 2.06 (t, 2H), 2.97 (m, 2H), 3.71 (s, 3H), 4.12 (t, 1H), 4.20–4.41 (m, 4H), 4.59 (s, 2H), 6.72 (d, 2H), 7.00–7.73 (m, 29H). MS (FAB) 891.4 (MH)$^+$, 916.7 (M+Na)$^+$, 931 (M+K)$^+$. Anal. Calcd for C$_{57}$H$_{56}$N$_4$O$_6$—H20: C-75.14, H-6.42, N-6.15. Found: C-75.25, H-6.02, N-6.49.

EXAMPLE 9b

Fmoc-Val-Lys(Mtr)-PABOH

This was prepared from Fmoc-Val-Lys(Mtr) 8b (15.28 g, 20.65 mmol) as described above for 9a (14.24 g, 82%). $^1$H-NMR (DMSO-d$_6$) δ 0.84 (ABq, 6H), 1.15–1.80 (m, 6H), 1.94 (m, 3H), 2.37 (brt, 1H), 3.69 (s, 3H), 3.91 (t, 1H), 4.21 (m, 4H), 4.41 (d and m, 3H), 5.10 (t, 1H), 6.79 (d, 2H), 7.29 (m, 18H), 7.53 (d, 2H), 7.68 (t, 2H), 7.86 (m, 2H), 8.02 (d, 1H), 9.94 (brs, 1H). IR (KBr) 700, 740, 1650, 1695. MS (ESI) 845.6 (MH)$^+$. Anal Calcd for C$_{53}$H$_{56}$N$_4$O$_6$-0.5H$_2$O: C-73.76, H-6.77, N-6.49. Found: C-74.01, H-6.68, N-6.63.

EXAMPLE 9c

Fmoc-Ala-Lys(Mtr)-PABOH

This was prepared from Fmoc-Ala-Lys(Mtr) 8c (10.8985 g, 15.31 mmol) as described above for 9a (11.0073 g, 88%). $^1$H-NMR (CDCl$_3$/CD$_3$OD) δ 1.29 (d and m, 5H), 1.42 (m, 2H), 1.57 (m, 1H), 1.79 (m, 1H), 2.05 (m, 2H), 3.68 (s, 3H), 4.11 (m, 2H), 4.30 (m, 3H), 4.51 (s, 2H), 6.69 (d, 2H), 7.00–7.55 (m, 22H), 7.66 (d, 2H). MS (ESI) 818.0 (MH)$^+$. Anal Calcd for C$_{51}$H$_{52}$N$_4$O$_6$-H$_2$O: C-73.36, H-6.52, N-6.71. Found: C-73.02, H-6.72, N-6.54.

EXAMPLE 10a

Phe-Lys(Mtr)-PAB-OH

Fmoc-Phe-Lys(Mtr)-PAB-OH 9a (4.2857 g, 4.80 mmol) in methylene chloride (35 mL) at rt was treated with diethylamine (50 mL). The mixture was sonicated briefly and stirred at rt for 4 h. after which time no starting material was observed by TLC. The solvents were evaporated and the residue was flushed with methylene chloride and chromatographed on silica, eluting with 1) 2%, 2) 3%, and 3) 4% methanol/methylene chloride, to give the product as a colorless foam (2.230 g, 69%). $^1$H-NMR (CDCl$_3$) δ 1.26–2.00 (m, 6H), 2.12 (t, 2H), 2.75 and 3.21 (ABq, each 1H), 3.68 (ABq, 1H), 3.76 (s, 3H), 4.42 (q, 1H), 4.66 (brs, 2H), 6.79 (d, 2H), 7.10–7.42 (m, 21H), 7.81 (d, 1H), 8.71 (s, 1H). MS (FAB) 693.4 (M+Na)$^+$, 709 (M+K)$^+$. Anal. Calcd for C$_{42}$H$_{46}$N$_4$O$_4$-1/2H$_2$O: C-74.20, H-6.97, N-8.24. Found: C-74.28, H-7.00, N-8.34.

EXAMPLE 10b

Val-Lys(Mtr)-PABOH

A solution of Fmoc-Val-Lys(Mtr)-PABOH 9b (13.94 g, 16.50 mmol) in 5:1 methylene chloride/methanol (75 mL) was treated with diethylamine (150 mL). The reaction was sonicated for 30 min and then allowed to stand at rt for 3 h. The solvents were evaporated and the residue flushed with methylene chloride. The remaining material was chromatographed on silica, eluting with 1) 2%, 2) 3%, 3) 3.5%, and 4) 4% methanol/methylene chloride, to give the product as a colorless foam (6.2510 g, 61%). $^1$H-NMR (CDCl$_3$/ CD$_3$OD) δ 0.80 (d, 3H), 0.97 (d, 3H), 1.48 (m, 4H), 1.70 (m, 1H), 1.90 (m, 1H), 2.11 (t, 2H), 2.27 (m, 1H), 3.27 (d, 1H), 3.76 (s, 3H), 4.53 (q, 1H), 4.58 (s, 2H), 6.78 (d, 2H), 7.10–7.50 (m, 16H), 7.95 (d, 1H), 9.11 (s, 1H). IR (KBr) 706, 830, 1034, 1248, 1510, 1648, 3310. MS (ESI) 623.2 (MH)$^+$. HRMS Calcd for C$_{38}$H$_{47}$N$_4$O$_4$: 623.3598. Found: 623.3606. Anal. Calcd for C$_{38}$H$_{46}$N$_4$O$_4$—H$_2$O: C, 71.22, H, 7.55, N, 8.74. Found: C, 71.41, H, 7.51, N, 8.66.

EXAMPLE 10c

Ala-Lys(Mtr)-PABOH

A solution of Fmoc-Ala-Lys(Mtr)-PABOH 9c (11.0073 g, 13.47 mmol) in DMF (50 mL) at rt was treated with diethylamine (25 mL). After 2.5 h the mixture was concentrated under high vacuum and the residue was flushed with methylene chloride (2×100 mL) and then toluene (150 mL). The remaining material was chromatographed on silica, eluting with 1) 4:1, 2) 1:1, 3) 1:1.6 and 4) 1:3 methylene chloride/(5:1 ethyl acetate/methanol), to give the product as a pale-yellow foam (5.7817 g, 72%). $^1$H-NMR (CDCl$_3$/ CD$_3$OD) δ 1.32 (d, 3H), 1.25–2.01 (m, 6H), 2.13 (t, 2H), 3.51 (q, 1H), 3.75 (s, 3H), 4.48 (q, 1H), 4.60 (brs, 2H), 6.79 (d, 2H), 7.12–7.50 (m, 16H), 7.89 (d, 1H), 8.89 (brs, 1H). MS (ESI) 595.2 (MH)$^+$.

EXAMPLE 11

N,N-Bis-Carbobenzyloxyethylenediamine

Benzyl chloroformate (40 mL, 280 mmol) was added dropwise over 45 min to a vigorously stirred solution of ethylenediamine (9.4 mL, 0.5 equiv) in 1M NaOH (310 mL, 1 equiv) at 0° C. A heavy white precipitate formed and the mixture was stirred for 4 h following addition. The resulting solid product was collected by filtration, washed with water and then hexane, and then air-dried overnight (46.17 g, 100%). $^1$H-NMR (CDCl$_3$) δ 3.32 (s, 4H), 5.10 (s, 4H), 5.23 (br, 2H), 7.35 (s, 10HS MS (ESI) 329.3 (MH)$^+$.

EXAMPLE 12

N-Carbobenzyloxyethylenediamine Hydrochloride

N,N-Bis-Carbobenzyloxyethylenediamine 11 (23.91 g, 72.8 mmol) in glacial acetic acid (100 mL) was treated with 12M HCl (12.1 mL, 2 equiv). The stirred mixture was heated at reflux for 1 h and then left to stand at rt overnight. A small amount of solid was removed by filtration and the filtrate was diluted with ether (700 mL) and left to stand at rt for 2 h. The resulting white solid product was collected by filtration, washed repeatedly with ether, and dried in a vacuum dessicator overnight (9.2440 g, 55%). $^1$H-NMR (DMSO-d$_6$) δ 2.87 (t, 2H), 3.30 (q, 2H), 5.04 (s, 2H), 7.33 (m, 5H), 7.49 (brt, 1H), 8.22 (br, 3H).

EXAMPLE 13

N-Carbobenzyloxy-N',N'-bis-(t-butoxycarbonylethyl)-ethylenediamine

A stirred solution of N-carbobenzyloxyethylenediamine hydrochloride 12 (5.0009 9, 21.68 mmol) in 3:1 methanol/ methylene chloride (100 mL) at rt was treated with t-butyl acrylate (64 mL, 20 equiv) and triethylamine (3.3 mL, 1.1 equiv). After 2 days the solvents were removed on the rotovap. The residue was dried in vacuo for 30 min and then partitioned between 30% ethyl acetate/ether and 50% sat. NaHCO$_3$. The organic phase was washed with water and brine, dried over sodium sulfate and evaporated. The residue was chromatographed on silica, eluting with 20% ethyl acetate/hexane, to give the product as a thick, colorless oil (9.3801 g, 96%). $^1$H-NMR (CDCl$_3$) δ 1.42 (s, 18H), 2.33 (t, 4H), 2.54 (t, 2H), 2.72 (t, 4H), 3.28 (q, 2H), 5.11 (s, 2H), 5.49 (brt, 1H), 7.33 (m, 5H). MS(DCl) 451 (MH)$^+$. Anal. Calcd for C$_{24}$H$_{38}$N$_2$O$_6$-0.5 H$_2$O: C, 62.72, H, 8.55, N, 6.09. Found: C, 62.54, H, 8.27, N, 5.95.

EXAMPLE 14

N,N-Bis-(t-butoxycarbonylethyl)ethylenediamine dihydrochloride

A solution of N-carbobenzyloxy-N',N'-bis-t-butoxypropionylethylenediamine 13 (18.3640 g, 40.76 mmol) was passed through a bed of Raney nickel in a fritted glass funnel. The filtrate was degassed with nitrogen and 10% Pd-C (1 g) and 12M HCl (6.8 mL, 2 equiv) were added. The mixture was hydrogenated on a Parr shaker at 50 psi for 16 h and then degassed once again with nitrogen. The catalyst was filtered off on a bed of celite. The filtrate was concentrated in vacuo and the residue flushed with methylene chloride (2×), giving an off-white foam (15.8696 g, 100%). $^1$H-NMR (CDCl$_3$) δ 1.48 (s, 18H), 2.97 (brt, 4H), 3.53 (m, 4H), 3.79 (m, 2H), 3.88 (m, 2H), 8.61 (br, 3H), 11.24 (br, 1H).

EXAMPLE 15

N-Maleoyl-N',N'-bis-(t-butoxycarbonylethyl)-ethylenediamine

A stirred suspension of N,N-bis-t-butoxypropionylethylenediamine dihydrochloride 14 (5.3363 g, 13.70 mmol) in acetonitrile (30 mL) at 0° C. under argon was treated with DIEA (4.77 mL, 2 equiv) and maleic anhydride (1.4111 g, 1.05 equiv). The reaction was allowed to warm gradually to rt. After 16 h trimethylsilyl chloride (5.2 mL, 3 equiv) and DIEA (7.2 mL, 3 equiv) were added. The mixture was heated at reflux for 4 h. Upon cooling, the solvents were removed in vacuo and the residue taken up in ethyl acetate. The solution was washed with sat. NaHCO$_3$, water and brine, dried over sodium sulfate and evaporated. The residue was chromatographed on silica, eluting with 2.5:1 hexane/ethyl acetate, to give the product as a pale-yellow oil (2.9986 g, 55%). $^1$H-NMR (CDCl$_3$) δ 1.42 (s, 18H), 2.30 (t, 4H), 2.61 (t, 2H), 2.73 (t, 4H), 3.59 (t, 2H), 6.68 (s, 2H). MS (ESI) 397.4 (MH)$^+$. Anal. Calcd for C$_{20}$H$_{32}$N$_2$O$_6$: C-60.59, H-8.13, N-7.07. Found: C-60.65, H-7.98, N-6.88.

EXAMPLE 16

N-Maleoyl-N',N'-bis-(carboxyethyl)ethylenediamine p-toluenesulfonic Acid

N-Maleoyl-N',N'-bis-t-butoxypropionylethylenediamine 15 (3.9934 g, 10.07 mmol) in methylene chloride (100 mL) at rt was treated with p-toluenesulfonic acid monohydrate (5.75 g, 3 equiv). The reaction was stirred at rt overnight. The solvent was evaporated at rt and the gummy residue dried in vacuo for 3 h. NMR showed complete loss of t-butyl ester signal. The crude product was carried on without further purification. $^1$H-NMR (DMSO-d$_6$) δ (contains 3 equiv of p-toluenesulfonic acid) 2.29 (s, 9H), 2.76 (m, 4H), 3.39 (m, 6H), 3.81 (brt, 2H), 7.11 (s, 2H), 7.17 (d, 6H), 7.49 (d, 6H), 9.27 (br, 1H).

EXAMPLE 17

N-Maleoyl-N',N'-bis-(Succinimidyloxycarbonyl-ethyl)ethylenediamine

A stirred solution of N-maleoyl-N',N'-bis-propionylethylenediamine p-toluenesultonate 16 (ca 10.07 mmol, containing two extra equiv of p-toluenesulfonic acid), triethylamine (4.4 mL, 3.1 equiv) and N-hydroxysuccinimide (2.5502 g, 2.2 equiv) in acetonitrile (90 mL) at 0° C. was treated with 0.5M DCC in methylene chloride (45.3 mL, 2.25 equiv). After 14 h the reaction was concentrated in vacuo and the residue partitioned between ethyl acetate and water. The aqueous phase was re-extracted with ethyl acetate. The combined organic phases were washed with water (2×) and brine, dried over sodium sulfate and evaporated. The residue was chromatographed on silica, eluting with 1:1 ethyl acetate/methylene chloride, to give the product as a pale-yellow foam (1.2043 g, 25%, 2 steps). $^1$H-NMR (CDCl$_3$) δ 2.72 (t, 4H), 2.84 (brs, 6H), 2.92 (t, 4H), 3.61 (t, 2H), 6.68 (s, 2H).

EXAMPLE 18a

MEt-IDP-(Lys(Mtr)-Lys(Mtr)-PABOH)$_2$

A solution of Lys(Mtr)-Lys(Mtr)-PABOH 6 (2.0903 g, 2.262 mmol) and N-maleoyl-N',N'-bis-succinimidyloxypropionylethylenediamine 17 (541.0 mg, 0.5 equiv) in DME (30 mL) was stirred for 2 days at rt. The reaction was concentrated in vacuo at 30° C. and the residue dissolved in ethyl acetate. The solution was washed with water (2×) and brine, dried over sodium sulfate and evaporated to give the product as a colorless glass (2.3623 g, 99%). $^1$H-NMR (CDCl$_3$/CH$_3$OD) δ 1.10–1.97 (m, 24H), 2.09 (m, 8H), 2.48 (m, 2H), 2.63 (m, 4H), 3.45 (m, 2H), 3.72 (s, 6H), 3.74 (s, 6H), 4.31 (m, 2H) 4.46 (m, 2H), 4.50 (s, 4H), 6.52 (s, 2H), 6.77 (m, 8H), 7.05–7.52 (m, 56H). MS (ESI) 2096.4 (MH)$^+$.

EXAMPLE 18b

MEt-IDP-(Phe-Lys(Mtr)-PABOH)$_2$

A stirred mixture of N-maleoyl-N',N'-bis-(carboxyethyl) ethylenediamine p-toluenesulfonic acid 16 (1.0643 g, 1.696 mmol) in DME (50 mL) at 0° C. was treated with triethylamine (0.6 mL, 2.5 equiv), Phe-Lys(Mtr)-PABOH 10a (2.2750 g, 2 equiv), NHS (439.0 mg, 2.25 equiv) and DCC (0.5M in methylene chloride, 8.5 mL, 2.5 equiv). The reaction was allowed to warm gradually to rt. After 16 h the DCU byproduct was filtered off and the filtrate was concentrated in vacuo. The residue was triturated with ether and the resulting solid was collected by filtration, washed with ether and dried in vacuo (2.0494 g, 76%). $^1$H-NMR (CDCl$_3$/CD$_3$OD) δ 1.20–1.95 (m, 12H), 2.07 (brt, 4H), 2.18 (m, 4H), 2.39 (t, 2H), 2.54 (m, 4H), 3.02 (m, 4H), 3.29 (m, 2H), 3.71 (s, 6H), 4.41 (m, 2H), 4.56 (brs, 4H), 4.69 (m, 2H), 6.57 (s, 2H), 6.72 (d, 4H), 6.97–7.55 (m, 42H), 9.00 (br, 2H). MS(FAB) 1611 (M+Na)$^+$, 1627 (M+K)$^+$.

EXAMPLE 18c

MEt-IDP-(Ala-Lys(Mtr)-PABOH)$_2$

This was prepared from N-maleoyl-N',N'-bis-succinimidyloxy-propionylethylenediamine 17 (. $^1$H-NMR (CDCl$_3$/CD$_3$OD) δ 1.20–1.80 (m, 15H), 1.95 (m, 4H), 2.13 (m, 4H), 2.39 (m, 2H), 2.55 (m, 4H), 3.31 (m, 2H), 3.60 (s, 6H), 4.28 (m, 4H), 4.40 (brs, 4H), 6.50 (s, 2H), 6.61 (d, 4H), 6.90–7.50 (m, 32H). MS (ESI) 1437.8 (MH)$^+$. HRMS Calcd for C$_{84}$H$_{96}$N$_{10}$O$_{12}$Na: 1459.7107. Found: 1459.707.

EXAMPLE 19a

MEt-IDP-(Lys(Mtr)-Lys(Mtr)-PABC-PNP)$_2$

MEt-IDP-(Lys(Mtr)-Lys(Mtr)-PABOH)$_2$ 18a (2.3623 g, 1.127 mmol) and bis-p-nitrophenylcarbonate (1.5424 g, 4.5 equiv) in dry methylene chloride (60 mL) were treated with freshly activated 4 Å powdered sieves (8.5 g) and DIEA (0.883 mL, 4.5 equiv). The mixture was stirred at rt for 16 h and then filtered. The filtrate was concentrated in vacuo to give a yellow solid which was dissolved as far as possible in ether (200 mL). The suspension was sonicated and stirred overnight at rt. The resulting white solid was collected by filtration, washed repeatedly with ether, and dried in vacuo (2.4084 g, 88%). $^1$H-NMR (CDCl$_3$/CH$_3$OD) δ 1.10–1.97 (m, 24H), 2.04 (m, 8H), 2.28 (m, 4H), 2.48 (m, 2H), 2.62 (m, 4H), 3.41 (m, 2H), 3.71 (s, 6H), 3.73 (s, 6H) 4.36 (m, 2H), 4.42 (m, 2H), 5.14 (s, 4H), 6.51 (s, 2H), 6.73 (m, 8H), 7.00–7.60 (m, 60H), 8.20 (d, 4H). Anal. Calcd for C$_{144}$H$_{148}$N$_{14}$O$_{22}$·2H$_2$O: C-70.23, H-6.22, N-7.96. Found: C-70.11, H-6.22, N-7.96.

EXAMPLE 19b

MEt-IDP-(Phe-Lys(Mtr)-PABC-PNP)$_2$

This was prepared from MEt-IDP-(Phe-Lys(Mtr)-PABOH)$_2$ 18b (517.8 mg, 0.326 mmol) as described above for 19a (509.1 mg, 74%). $^1$H-NMR (CDCl$_3$/CD$_3$OD) δ 1.20–1.97 (m, 12H), 2.08 (m, 4H), 2.24 (m, 4H), 2.40 (t, 2H), 2.61 (m, 4H), 3.10 (m, 4H), 3.29 (m, 2H), 3.73 (s, 6H), 4.41 (q, 2H), 4.69 (q, 2H), 5.22 (s, 4H), 6.58 (s, 2H), 6.77 (d, 4H), 7.00–7.50 (m, 42H), 7.56 (d, 4H), 8.22 (d, 4H), 8.74 (brs, 2H).

EXAMPLE 19c

MEt-IDP-(Ala-Lys(Mtr)-PABC-PNP)$_2$

This was prepared from MEt-IDP-(Ala-Lys(Mtr)-PABOH)$_2$ 18c (6.24 g, 4.34 mmol) as described above for 19a (6.00 g, 74%). $^1$H-NMR (CDCl$_3$/CD$_3$OD) δ 1.26 (d, 6H), 1.33 (m, 4H), 1.42 (m, 4H), 1.62 (m, 2H), 1.83 (m, 2H), 2.18 (m, 4H), 2.41 (m, 6H), 2.64 (m, 4H), 3.72 (s, 6H), 4.40 (m, 4H), 5.18 (brs, 4H), 6.60 (s, 2H), 6.72 (d, 4H), 7.05–7.50 (m, 38H), 7.56 (d, 4H), 8.21 (d, 4H).

EXAMPLE 20a

MEt-I DP-(Lys(Mtr)-Lys(Mtr)-PABC-DOX)$_2$

A stirred solution of MEt-IDP-(Lys(Mtr)-Lys(Mtr)-PABC-PNP)2 19a (753.0 mg, 0.3103 mmol) and DOX hydrochloride (377.9 mg, 2.1 equiv) in DMF (25 mL) at rt was treated with DIEA (0.114 mL, 2.1 equiv). After 3 days the mixture was poured into ethyl acetate (200 mL) and the solution was washed with water (4×) and brine, dried over sodium sulfate, and evaporated to give an orange glass. This was triturated with ether (200 mL), and the resulting solid was collected by filtration and then chromatographed on silica, eluting with 16:1 methylene chloride/methanol, to give the product as an orange solid (803.8 mg, 80%). $^1$H-NMR (DMF-d$_7$) δ 1.23 (d, 6H), 1.30–1.90 (m, 28H), 2.04 (m, 10H), 2.30 (m, 6H), 2.41 (d, 2H), 2.51 (m, 2H), 2.72 (m, 4H), 3.12 (q, 4H), 3.64 (m, 2H), 3.75 (s, 12H), 3.91 (m, 2H), 4.08 (s and m, 8H), 4.33 (m, 4H), 4.45 (m, 2H), 4.79 (s, 4H), 4.89 (d, 2H), 4.96 (brs, 4H), 5.12 (m, 2H), 5.40 (brs, 2H), 5.60 (s, 2H), 6.72 (d, 2H), 6.87 (q, 8H), 6.92 (s, 2H), 7.10–7.50 (m, 54H), 7.67 (m, 6H), 7.93 (m, 2H), 9.91 (brs, 2H).

EXAMPLE 20b

MEt-IDP-(Phe-Lys(Mtr)-PABC-DOX)$_2$

This was prepared from MEt-IDP-(Phe-Lys(Mtr)-PABC-PNP)$_2$ 19b (340.8 mg, 0.161 mmol) as described above for 20a (411.2 mg, 93%). $^1$H-NMR (CDCl$_3$/CD$_3$OD) δ 1.10–1.65 (m and d, 16H), 2.07 (m, 6H), 2.10–2.45 (m, 10H), 2.55 (m, 4H), 3.00 (m, 6H), 3.26 (m and d, 4H), 3.71 (s, 6H), 3.82 (m, 2H), 4.00 (brs, 6H), 4.11 (m, 2H), 4.40 (m, 2H), 4.63 (m, 2H), 4.74 (s, 4H), 4.90 (ABq, 4H), 5.13 (brs, 2H), 5.44 (brs, 2H), 5.58 (brd, 2H), 6.60 (s, 2H), 6.71 (d, 4H), 6.90–7.55 (m, 44H), 7.72 (t, 2H), 7.94 (d, 2H).

EXAMPLE 20c

MEt-IDP-(Ala-Lys(Mtr)-PABC-DOX)$_2$

This was prepared from MEt-IDP-(Ala-Lys(Mtr)-PABC-PNP)$_2$ 19c (6.00 g, 3.39 mmol) as described abovefor 20a (620 mg, 7%). $^1$H-NMR (CDCl$_3$/CD$_3$OD) δ 1.17 (m, 16H), 1.29 (m, 4H), 1.40 (m, 4H), 1.72 (m, 7H), 1.99 (m, 4H), 2.15 (m, 10H), 2.53 (m, 6H), 3.03 (ABq, 4H), 3.39 (m, 2H), 3.52 (brs, 2H), 3.64 (s, 6H), 3.95 (s, 6H), 4.04 (m, 2H), 4.26 (m, 2H), 4.33 (m, 2h), 4.68 (s, 4H), 4.80 (ABq, 4H), 5.10 (brs, 2H), 5.47 (brs, 2H), 6.55 (s, 2H), 6.64 (d, 4H), 6.98–7.40 (m, 34H), 7.68 (t, 2H), 7.89 (d, 2H).

EXAMPLE 21a

MEt-IDP-(Lys-Lys-PABC-DOX)$_2$·5CL$_2$CHCO$_2$H

A stirred solution of MEt-IDP-(Lys(Mtr)-Lys(Mtr)-PABC-DOX)$_2$ 20a (318.7 mg, 0.0985 mmol) in methylene chloride (21 mL) at rt was treated with anisole (3.2 mL, 300 equiv) and dichloroacetic acid (0.244 mL, 30 equiv). After 2.5 h ethyl acetate (50 mL) was added. The mixture was stored at 4° C. for 2 h. The resulting solid was collected by filtration and washed repeatedly with ethyl acetate followed by ether, and then air-dried (274.5 mg, 99.8 %). $^1$H-NMR (DMF-d$_7$) δ 1.23 (d, 6H), 1.54 (m, 8H), 1.75 (m, 18H), 2.01 (m, 2H), 2.22 (q, 2H), 2.40 (m, 6H), 3.07 (m, 8H), 3.89 (m, 2H), 4.06 (s, 6H), 4.34 (m, 4H), 4.52 (m, 2H), 4.79 (s, 4H), 4.96 (s, 4H), 5.13 (brs, 2H), 5.39 (s, 2H), 5.72 (m, 2H), 6.30 (s, 5H), 6.77 (d, 2H), 6.99 (s, 2H), 7.30 (d, 4H), 7.71 (m, 6H), 7.93 (m, 2H), 8.45 (m, 8H). MS (ESI) 2147.6 (MH)$^+$.

EXAMPLE 21b

MEt-IDP-(Phe-Lys-PABC-DOX)$_2$·3Cl$_2$CHCO$_2$H

This was prepared from MEt-IDP-(Phe-Lys(Mtr)-PABC-DOX)$_2$ 20b (280.0 mg, 0.103 mmol) as described above for 21a (237.1 mg, 90%). $^1$H-NMR (CDCl$_3$/CD$_3$OD) δ 1.20 (d, 6H), 1.37 (m, 4H), 1.70 (m, 10H), 2.06 (m, 2H), 2.29 (m, 6H), 2.61 (m, 2H), 2.82 (m, 8H), 3.00 (m, 4H), 3.16 (d, 2H), 3.75 (m, 2H), 3.99 (s, 6H), 4.07 (m, 2H), 4.44 (m, 4H), 4.70 (s, 4H), 4.89 (ABq, 4H), 5.16 (brs, 2H), 5.40 (brs, 2H), 5.85 (s, 3H), 6.63 (s, 2H), 7.08 (m, 14H), 7.39 (d, 2H), 7.69 (t, 2H), 7.90 (d, 2H). MS (ESI) 1092.8 (MH$_2$)$^{2+}$, 2184.8 (MH)$^+$.

EXAMPLE 21c

MEt-IDP-(Ala-Lys-PABC-DOX)$_2$·3Cl$_2$CHCO$_2$H

This was prepared from MEt-IDP-(Ala-Lys(Mtr)-PABC-DOX)$_2$ 20c (569 mg, 0.248 mmol) as described above for 21a (455 mg, 80%). $^1$H-NMR (CDCl$_3$/CD$_3$OD) δ 1.17 (d and m, 8H), 1.22 (brd, 6H), 1.38 (m, 4H), 1.65 (m, 10H), 2.02 (d, 2H), 2.23 (d, 2H), 2.41 (m, 4H), 2.82 (m, 6H), 2.99 (m, 4H), 3.10 (d, 2H), 3.54 (m and brs, 4H), 3.93 (s, 6H), 4.05 (m, 2H), 4.19 (m, 2H), 4.40 (m, 2H), 4.68 (brs, 4H), 4.82 (ABq, 4H), 5.10 (brs, 2H), 5.38 (brs, 2H), 5.79 (s, 3H), 6.61 (s, 2H), 7.09 (d, 4H), 7.29 (m, 2H), 7.40 (d, 4H), 7.67 (t, 2H), 7.82 (d, 2H). MS (ESI) 2032.8 (MH)$^+$. MS (ESI) 1016.6 (MH$_2$)$^{2+}$, 2032.4 (MH)$^+$.

EXAMPLE 22

N-Carbobenzyloxy-N',N'-bis-(t-Butoxycarbonylmethyl)-ethylenediamine

A stirred mixture of N-carbobenzyloxyethylenediamine hydrochloride 12 (13.95 g, 60.48 mmol) and potassium bicarbonate (24.22 g, 4 equiv) in DMF (100 mL) at 0° C. was treated with t-butyl bromoacetate (22 mL, 2.25 equiv), dropwise over 10 min. The mixture was allowed to warm to rt. Stirring was continued for 12 h and then the mixture was partitioned between 3:1 ether/ethyl acetate and 50% saturated sodium bicarbonate. The organic phase was washed with water (3×), brine, dried over sodium sulfate and evaporated to give a thick oil. This was flushed with heptane several times at 60° C. to remove excess t-butyl bromoacetate and then chromatographed on silica, eluting with 1) hexane, 2) 5% ethyl acetate/hexane, and 3) 25% ethyl acetate/hexane, to give the product as a thick, colorless oil (18.53 g, 73%). $^1$H-NMR (CDCl$_3$) δ 1.43 (s, 9H), 2.83 (t, 2H), 3.22 (q, 2H), 3.41 (s, 4H), 5.12 (s, 2H), 6.04 (brt, 1H), 7.33 (m, 5H). MS (ESI) 423.4 (MH)$^+$.

EXAMPLE 23

N,N-Bis-(t-Butoxycarbonylmethyl)ethylenediamine-dihydrochloride

A solution of N-carbobenzyloxy-N',N'-bis-(t-butoxyacetyl)ethylenediamine 22 (15.02 g, 35.54 mmol) in ethanol (75 mL) was filtered through a bed a Raney nickel. Acetic acid (6.1 mL, 3 equiv) was added and the mixture was hydrogenated as described above for 4. The crude product was carried on without further purification.

EXAMPLE 24

N-Maleoyl-N',N'-bis-(t-Butoxycarbonylmethyl)-ethylenediamine

N,N-Bis-(t-butoxyacetyl)ethylenediamine dihydrochloride 23 (ca. 35.54 mmol) in CHCl$_3$ (150 mL) at rt was treated with maleic anhydride (3.83 g, 1.1 equiv). The mixture was stirred for 14 h and then the solvent was evaporated. The residue was flushed with CHCl$_3$ (200 mL) and then dissolved in acetonitrile (200 mL) under argon. The stirred mixture was cooled to 0° C. and treated with trimethylsilyl chloride (18 mL, 4 equiv) and triethylamine (20 mL, 4 equiv). The ice bath was removed and the mixture was heatedat reflux for 2.5 h. The solvents were removed under reduced pressure and the residue partitioned between ether and 30% sat sodium bicarbonate. The organic phase was washed with water, brine, dried and evaporated. The residue was chromatographed on silica, eluting with 2.5:1 hexane/ethyl acetate, to give the product as a waxy solid (8.25 g, 63%, 3 steps). $^1$H-NMR (CDCl$_3$) δ 1.42 (s, 9H), 2.91 (t, 2H), 3.41 (s, 4H), 3.62 (t, 2H), 6.68 (s, 2H). MS (DCl) 369 (MH)$^+$.

EXAMPLE 25

N-Maleoyl-N',N'-bis-(Carboxymethyl)ethylenediamine.p-toluenesulfonic Acid

A stirred solution of N-maleoyl-N',N'-bis-(t-butoxycarbonylmethyl)-ethylenediamine 24 (2.6718 g, 7.25 mmol) in methylene chloride (70 mL) at rt was treated with p-toluenesulfonic acid monohydrate (4.1400 g, 3 equiv). After 36 h the resulting white sQlid was collected by filtration, washed repeatedly with methylene chloride and ether, and then dried in vacuo. NMR showed 1.4–1.5 equiv of p-toluenesulfonic acid per equiv of product (3.7531 g, 100%). $^1$H-NMR (DMSO-d$_6$) δ 2.29 (s, 3.9H), 3.39 (t, 2H), 3.77 (t, 2H), 4.07 (s, 4H), 7.08 (s, 2H), 7.12 (d, 2.6H), 7.49 (d, 2.6H). MS (DCl) 257 (MH)$^+$. Anal. Calcd for C$_{10}$H$_{13}$N$_2$O$_6$-1.3C$_7$H$_7$O$_3$S-2H$_2$O: C-44.48, H-5.10, N-5.43. Found: C-44.51, H-4.96, N-5.20.

EXAMPLE 26a

MEt-IDA-(Phe-Lys(Mtr)-PABOH)$_2$

A stirred solution of Phe-Lys(Mtr)-PABOH 10a (2.5179 g, 3.753 mmol), N-maleoyl-N',N'-bis-(carboxymethyl)ethylenediamine.p-toluenesulfonic acid 25 (804.0 mg, 0.5 equiv) and N-hydroxysuccinimide (475.2 mg, 1 equiv) in DME (150 mL) at 000 was treated with DIEA (0.33 mL, 0.5 equiv) and 0.5M DCC in methylene chloride (9.0 mL, 1.2 equiv). After 6 h DCU was removed by filtration and the filtrate was concentrated in vacuo. The residue was partitioned between ethyl acetate and water. The organic phase was washed with water (2×) and brine, dried over sodium sulfate, and concentrated in vacuo. The residue was dissolved as far as possible in methylene chloride (100 mL) and then the mixture was diluted with ether (100 mL). After being left to stand overnight the resulting solid was collected by filtration and air-dried (2.6295 g, 90%). $^1$H-NMR (CDCl$_3$) δ 1.05–1.98 (m, 12H), 2.09 (brt, 4H), 2.51 (bnt, 2H), 2.91 (brs, 4H), 3.03 (m, 4H), 3.39 (brt, 2H), 3.72 (s, 6H), 4.34 (q, 2H), 4.52 (s, 4H), 4.71 (q, 2H), 6.55 (s, 2H), 6.78 (d, 4H), 7.03–7.50 (m, 34H), 8.72 (brs, 2H). MS (FAB) 1583.9 (M+Na)$^+$, 1600.9 (M+K)$^+$.

EXAMPLE 26b

MEt-IDA-(Val-Lys(Mtr)-PABOH)$_2$

This was prepared from N-maleoyl-N',N'-bis-(carboxymethyl)ethylenediamine.p-toluenesulfonic acid 25 (500 mg, 1.16 mmol) and Val-Lys(Mtr)-PABOH 10b (1.44 g, 2 equiv) as described above for 26a (1.68 g, 95%). $^1$H-NMR (CDCl$_3$/CD$_3$OD) δ 0.90 (t, 12H), 1.10–1.88 (m, 14H), 2.10 (m, 4H), 2.71 (brt, 2H), 3.24 (brs, 4H), 3.46 (m, 2H), 3.77 (s, 6H), 4.25 (d, 2H), 4.42 (t, 2H), 4.58 (s, 4H), 6.63 (s, 2H), 6.79 (d, 4H), 7.05–7.55 (m, 32H). IR (KBr) 698, 1510, 1638, 1708. MS (ESI) 1466.0 (MH)$^+$. Anal. Calcd for C$_{86}$H$_{100}$N$_{10}$O$_{12}$-2H$_2$O: C-68.78, H-6.98 N-9.33. Found: C-68.87, H-7.54, N-9.48.

EXAMPLE 27a

MEt-IDA-(Phe-Lys(Mtr)-PABC-PNP)$_2$

A stirred suspension of MEt-IDA-(Phe-Lys(Mtr)-PABOH)$_2$ 26a (471.5 mg, 0.319 mmol) and bis-p-nitrophenylcarbonate (971.0 mg, 10 equiv) in methylene chloride (25 mL) at rt under argon was treated with DIEA (0.611 mL, 11 equiv). After 16 h the solvent was removed in vacuo and the residue dried in vacuo for 3 h. The residue was dissolved in methylene chloride (15 mL) and to this was added ether (30 mL) with slow stirring. The resulting suspension was left to stand overnight. The solid was collected by filtration, washed with 2:1 etherlmethylene chloride and dried in vacuo (411.5 mg, 68%). $^1$H-NMR (CDCl$_3$) δ 1.30 (m, 4H), 1.45 (m, 4H), 1.62 (m, 2H), 1.89

(m, 2H), 2.10 (t, 4H), 2.58 (brt, 2H), 3.00 (brs, 4H), 3.06 (m, 4H), 3.31 (t, 2H), 3.73 (s, 6H), 4.38 (q, 2H), 4.68 (q, 2H), 5.21 (s, 4H), 6.53 (s, 2H), 6.77 (d, 4H), 7.03–7.38 (m, 34H), 7.41 (d, 8H), 7.57 (d, 4H), 8.22 (d, 4H), 8.79 (brs, 2H). MS (ESI) 1893.9 (MH)$^+$.

EXAMPLE 27b

MEt-IDA-(Val-Lys(Mtr)-PABC-PNP)$_2$

This was prepared from MEt-IDA-(Val-Lys(Mtr)-PABOH)$_2$ 26b (300 mg, 0.205 mmol) as described above for 27a (347.7 mg, 94%). $^1$H-NMR (CDCl$_3$) δ 0.88 (t, 12H), 1.25–1.75 (m, 12H), 1.93 (m, 2H), 2.07 (m, 4H), 2.71 (m, 2H), 3.21 (brs, 4H), 3.55 (m, 2H), 4.26 (m, 2H), 4.34 (m, 2H), 5.19 (s, 4), 6.59 (s, 2H), 6.76 (d, 4H), 7.10–7.40 (m, 32H), 7.59 (m, 4H), 8.21 (d, 4H), 8.65 (br, 2H).

EXAMPLE 28a

MEt-IDA-(Phe-Lys(Mtr)-PABC-DOX)$_2$

A solution of MEt-IDA-(Phe-Lys(Mtr)-PABC-PNP)$_2$ 27a (410.3 mg, 0.217 mmol) and doxorubicin hydrochloride (283.0 mg, 2.25 equiv) in NMP (10 mL) at rt was treated with DIEA (0.094 mL, 2.5 equiv). After 48 h the mixture was poured into ethyl acetate. The solution was washed with water (3×) and evaporated in vacuo. In each case some orange solid, that was shown by TLC to contain product, was formed. This was collected by filtration and combined later with the organic-soluble components before chromatography. The combined materials were chromatographed on silica, eluting with 1) 6:4, and 2) 1:1 methylene chloride/ (5:1 ethyl acetate/methanol), to give the product as an orange solid (351.8 mg, 60%). $^1$H-NMR (CDCl$_3$/CH$_3$OD) δ 1.22 (brd, 10H), 1.40 (m, 4H), 1.51 (m, 4H), 1.75 (m, 6H), 2.07 (m, 4H), 2.20 (ABq, 4H), 2.50 (brt, 2H), 2.93 (brs, 4H), 2.99 (m, 4H), 3.23 (brs, 4H), 3.57 (m, 2H), 3.68 (s, 6H), 3.75 (m, 2H), 3.97 (s, 6H), 4.06 (m, 2H), 4.29 (m, 2H), 4.56 (m, 2H), 4.71 (s, 4H), 4.81 (ABq, 4H), 5.16 (brs, 2H), 5.42 (brs, 2H), 6.55 (s, 2H), 6.71 (d, 4H), 6.98–7.50 (m, 44H), 7.71 (t, 2H), 7.94 (d, 2H), 8.69 (br, 2H). MS (ESI) 2702.4 (MH)$^+$.

EXAMPLE 28b

MEt-IDA-(Val-Lys(Mtr)-PABC-DOX)$_2$

This was prepared from MEt-IDA-(Val-Lys(Mtr)-PABC-PNP)$_2$ 27b (6.351 g, 3.536 mmol) as described above for 28a (2.79 g, 30%). $^1$H-NMR (DMSO-d$_6$) δ 0.76 (ABq, 12H), 1.10 (d, 6H), 1.20–1.60 (m, 12H), 1.88 (m, 8H), 2.13 (q, 4H), 2.33 (m, 2H), 2.64 (m, 2H), 2.93 (m, 4H), 3.21 (brs, 4H), 3.64 (s, 6H), 3.70 (m, 2H), 3.91 (s, 6H), 4.15 (m, 4H), 4.26 (m, 2H), 4.55 (d, 4H), 4.70 (d, 2H), 4.88 (m, 4H), 5.19 (brs, 2H), 5.45 (s, 2H), 6.75 (d, 4H), 6.86 (s, 2H), 7.10 (m, 4H), 7.18 (m, 18H), 7.30 (d, 6H), 7.49 (m, 4H), 7.55 (m, 2H), 7.82 (m, 4H), 8.04 (m, 2H), 9.94 (br, 2H). MS (ESI) 2608.0 (MH)$^+$.

EXAMPLE 29a

MEt-IDA-(Phe-Lys-PABC-DOX)$_2$·2Cl$_2$CHCO$_2$H

A stirred solution of MEt-IDA-(Phe-Lys(Mtr)-PABC-DOX)$_2$ 28a (192.0 mg, 0.071 mmol) in methylene chloride (15 mL), at rt was treated with anisole (1.54 mL, 200 equiv) and dichloroacetic acid (0.117 mL, 20 equiv). After 1 h ethyl acetate (15 mL) was added. The resulting solid was collected by filtration, washed with ethyl acetate and ether and dried in vacuo (181.0 mg, 15 100%). $^1$H-NMR (CDCl$_3$/CH$_3$OD) δ 1.19 (d, 6H), 1.33 (m, 4H), 1.52 (m, 6H), 1.74 (m, 6H), 2.14 (ABq, 4H), 2.49 (brt, 2H), 2.93 (m, 12H), 3.25 (brs, 4H), 3.51 (m, 2H), 3.77 (m, 2H), 3.90 (s, 6H), 4.04 (m, 2H), 4.32 (m, 2H), 4.65 (s, 4H), 4.82 (m, 4H), 5.05 (brs, 2H), 5.33 (brs, 2H), 5.82 (brs, 2H), 6.63 (s, 2H), 7.01 (m, 14H), 7.32 (m, 6H), 7.63 (t, 2H), 7.79 (d, 2H). MS (ESI) 1078.8 (MH$_2$)$^{2+}$, 2156.8 (MH)$^+$.

EXAMPLE 29b

MEt-IDA-(Val-Lys-PABC-DOX)$_2$·2Cl$_2$CHCO$_2$H

This was prepared from MEt-IDA-(Val-Lys(Mtr)-PABC-DOX)$_2$ 28b (232 mg, 0.0891 mmol) as described above for 29a (171 mg, 78%). $^1$H-NMR (DMSO-d$_6$) δ 0.78 (ABq, 12H), 1.10 (d, 6H), 1.15–1.70 (m, 12H), 1.78 (m, 2H), 1.92 (m, 2H), 2.11 (m, 4H), 2.72 (m, 4H), 2.94 (m, 4H), 3.68 (m, 2H), 3.94 (s, 6H), 4.15 (m, 4H), 4.26 (m, 2H), 4.55 (brs, 4H), 4.66 (brs, 2H), 4.86 (m, 4H), 5.19 (brs, 2H), 5.45 (s, 2H), 5.91 (s, 2H), 6.82 (d, 2H), 6.93 (s, 2H), 7.21 (d, 4H), 7.51 (d, 4H), 7.58 (m, 2H), 7.76 (m, 4H), 7.84 (m, 4H), 8.19 (m, 2H), 10.00 (brs, 6H). IR (KBr) 1648, 1709. MS (ESI) 1030.9 (MH$_2$)$^{+2}$, 2060.8 (MH)$^+$.

EXAMPLE 30

MEt-IDA-(Phe-Lys(Mtr)-PABC-MMC)$_2$

A stirred mixture of MEt-IDA-(Phe-Lys(Mtr)-PABC-PNP)$_2$ 27a (183.8 mg, 0.0971 mmol), mitomycin C (73.1 mg, 2.25 equiv), N-hydroxybenzotriazole monohydrate (131.3 mg, 10 equiv) and freshly activated 4 Å powdered sieves (0.5 g) in NMP (6 mL) under argon at rt was treated with DIEA (0.17 mL, 10 equiv). After 40 h the mixture was filtered and the filtrate diluted with ethyl acetate (80 mL). The solution was washed with water (4×), brine, dried over sodium sulfate and evaporated. The residue was chromatographed on silica, eluting with 2:1 methylene chloride/(5:1 ethyl acetate/methanol), to give the product as a light purple solid (201.7 mg, 91%). $^1$H-NMR (CDCl$_3$) δ 1.27 (m, 4H), 1.42 (m, 4H), 1.60 (m, 2H), 1.69 (s, 6H), 1.83 (m, 2H), 2.06 (brt, 4H), 2.57 (m, 2H), 3.00 (m, 4H), 3.07 (brs, 4H), 3.13 (s, 6H), 3.28 (m, 4H), 3.41 (d, 2H), 3.59 (ABq, 2H), 3.72 (s, 6H), 4.20 (t, 2H), 4.41 (d and m, 3H), 4.66 (m, 2H), 4.88 (d, 4H), 5.10 (d, 2H), 5.39 (br, 6H), 6.49 (s, 2H), 6.72 (d, 4H), 6.90–7.55 (m, 42H), 7.62 (br, 2H), 9.07 (br, 2H). MS (ESI) 1142.0 (MH$_2$)$^{2+}$, 2282.0 (MH)$^+$.

EXAMPLE 31

MEt-IDA-(Phe-Lys-PABC-MMC)$_2$·2Cl$_2$CHCO$_2$H

A solution of MEt-IDA-(Phe-Lys(Mtr)-PABC-MMC)$_2$ 30 (134.6 mg, 0.0590 mmol) in methylene chloride (3 mL) at rt was treated with anisole (1.28 mL, 200 equiv) and 1 M chloroacetic acid in methylene chloride (1.18 mL, 20 equiv). After 3.5 h ethyl acetate (30 mL) was added. The resulting purple solid was collected by filtration, washed with ethyl acetate and air-dried (97.8 mg, 82%). The product appeared to decompose in solution to one product by HPLC. $^1$H-NMR (CDCl$_3$/CH$_3$OD) δ 1.33 (m, 4H), 1.63 (s and M, 12H), 1.77 (m, 2H), 2.52 (m, 2H), 2.82 (m, 6H), 3.03 (m, 2H), 3.10 (s and brs, 10H), 3.27 (m, 2H), 3.53 (ABq, 2H), 3.96 (brs, 4H), 4.11 (m, 2H), 4.35 (d and m, 3H), 4.53 (m, 2H), 4.78 (ABq, 2H), 4.94 (m, 4H), 6.62 (s, 2H), 7.10 (m, 10H), 7.19 (d, 4H), 7.41 (d, 4H). MS (FAB) 1738.3 (M+Na)$^+$, 1776.4 (M+K)$^+$.

EXAMPLE 32

2'-Methoxytrityl-Paclitaxel

A stirred solution of paclitaxel (0.51 g, 0.597 mmol) and p-methoxytrityl chloride (4.63 g, 25 equiv) in methylene chloride (14 mL) under nitrogen at rt was treated with pyridine (1.23 mL, 25 equiv). After 16 h at rt the solvent was evaporated and the residue dissolved in ethyl acetate. The solution was washed with cold pH 5 buffer (2×100 mL), water and brine, dried and evaporated. The residue was chromatographed on silica, eluting with 3% methanol/methylene chloride, to give the product as a white solid (482 mg, 72%). $^1$H NMR (CDCl$_3$) δ 1.11 (s, 3H), 1.17 (s, 3H), 1.55 (s, 3H), 1.67 (s, 3H), 1.90 and 2.54 (m, 2H), 2.26 (s, 3H), 2.51 (s, 3H), 2.54 (m, 2H), 3.66 (d, 1H), 3.78 (s, 3H), 4.21 (ABq, 2H), 4.41 (m, 1H), 4.63 (d, 1H), 4.92 (d, 1H), 5.62 (d, 1H), 5.70 (m, 2H), 6.22 (s, 1H), 6.74 (d, 2H), 7.09–7.60 (m, 23H), 7.80 (d, 2H), 8.09 (d, 2H). MS (FAB) 1148 (M+Na)$^+$, 1164 (M+K)$^+$.

EXAMPLE 33

MEt-IDA-(Phe-Lys(Mtr)-PABC-7-Paclitaxel)$_2$

A solution of paclitaxel-2'-Mtr 32 (789.3 mg, 0.701 mmol) in methylene chloride (5 mL) at 0° C. under argon was treated with DIEA (0.122 mL, 1 equiv), pyridine (0.057 mL, 1 equiv) and diphosgene (0.043 mL, 0.5 equiv). The mixture was allowed to warm to rt for 1.5 h and then it was added, via syringe, to a stirred suspension of MEt-IDA-(Phe-Lys(Mtr)-PABOH)$_2$ 26a (547.3 mg, 0.5 equiv) in methylene chloride (5 mL) and DIEA (0.122 mL, 1 equiv) at rt. After 16 h the mixture was diluted with ethyl acetate and washed with pH 5 buffer (0.5M biphthalate), water and brine, dried over sodium sulfate, and concentrated in vacuo. The residue was chromatographed on silica, eluting with 1) 5:1 and 2) 3:1 methylene chloride/(5:1 ethyl acetate/methanol), to give the product as a colorless glass (859.2 mg, 63%). Also recovered was a small amount of the mono-taxol adduct (172.0 mg, 18%). $^1$H-NMR (CDCl$_3$/CH$_3$OD) δ 1.05–1.80 (4×m, 12H), 1.12 (s, 6H), 1.14 (s, 6H), 1.61 (s, 6H), 1.79 (s, 6H), 1.90 (m, 2H), 2.09 (m, 4H), 2.16 (s, 6H) 2.28 (s, 6H), 2.58 (m, 3H), 2.98 (brs, 4H), 3.05 (m, 4H), 3.37 (m, 2H), 3.75 (s, 6H), 3.78 (s, 6H), 4.16 (d, 2H), 4.27 (d, 2H), 4.32 (m, 2H), 4.63 (d and m, 4H), 4.92 (d, 2H), 5.16 (m, 4H), 5.49 (ABq, 2H), 5.62 (d, 2H), 5.71 (m, 4H), 6.33 (s, 2H), 6.53 (s, 2H), 6.75 (q, 8H), 6.97 (brd, 2H), 7.05–7.65 (m, 96H), 7.81 (d, 4H), 8.08 (d, 4H), 8.68 (brs, 2H).

EXAMPLE 34

MEt-IDA-(Phe-Lys-PABC-7-Paclitaxel)$_2$·2ClCH$_2$CO$_2$H

MEt-IDA-(Phe-Lys(Mtr)-PABC-7-Paclitaxel)$_2$ 33 (333.0 mg, 0.0861 mmol) in methylene chloride (3 mL) was treated with anisole (1.87 mL, 200 equiv) and 1 M chloroacetic acid in methylene chloride (1.72 mL, 20 equiv). After 4 h the mixture was diluted with ether (30 mL). The resulting suspension was sonicated for several minutes and then the solid was collected by filtration and washed with ether (256.3 mg, 97%). The product was shown to decompose slowly in solution. $^1$H-NMR (DMF-d$_7$) δ 1.15 (s, 6H), 1.19 (s, 6H), 1.77 (s, 6H), 1.94 (s, 6H), 1.30–2.00 (m, 12H), 2.15 (m, 4H), 2.59 (m, 4H), 3.09 (m, 8H), 3.93 (d, 2H), 4.16 (s, 4H), 4.69 (m, 4H), 4.90 (d, 2H), 5.07 (d, 2H), 5.16 (m, 4H), 5.56 (ABq, 2H), 5.67 (d, 2H), 5.70 (ABq, 2H), 6.14 (t, 2H), 6.42 (s, 2H), 6.49 (m, 2H), 7.02 (s, 2H), 7.10–7.90 (m, 44H), 8.11 (d, 4H), 9.09 (br, 2H). MS (ESI) 2778.2 (MH)$^+$.

EXAMPLE 35

N-Carbobenzyloxy-N',N'-bis-(t-butoxycarbonylmethyl)propylenediamine

This was prepared from N-carbobenzyloxypropylenediamine hydrochloride (3.4624 g, 14.15 mmol) as described above for 22 (5.3017 g, 86%). $^1$H-NMR (CDCl$_3$) δ 1.45 (s, 18H), 1.63 (m, 2H), 2.72 (t, 2H), 3.32 (t, 2H), 3.38 (s, 4H), 5.11 (s, 2H), 6.26 (brt, 1H), 7.33 (m, 5H). MS (ESI) 437.5 (MH)$^+$.

EXAMPLE 36

N,N-Bis-(t-butoxycarbonylmethyl)propylenediamine Diacetic Acid

A solution of N-carbobenzyloxy-N',N'-bis-(t-butoxycarbonylmethyl)-propylenediamine 35 (5.3017 g, 12.144 mmol) in ethanol (75 mL) was filtered through a bed of Raney nickel into a solution of acetic acid (2.1 mL, 3 equiv) in ethanol (75 mL). The filtrate was degassed with nitrogen and treated with 10% palladized charcoal (0.4 g). The mixture was hydrogenated at 50 psi on a Parr apparatus for 16 h and then the catalyst was filtered off on a bed of celite. The filtrate was concentrated in vacuo and the residue flushed with chloroform (150 mL). The crude product was carried on without further purification.

EXAMPLE 37

N-Maleoyl-N',N'-bis-(t-butoxycarbonylmethyl)-propylenediamine

This was prepared from N,N-bis-(t-butoxycarbonylmethyl)propylenediamine diacetic acid 36 (12.14 mmol) as described above for 24. The crude product was chromatographed on silica, eluting with 3:1 hexane/ethyl acetate, to give the product as a pale-yellow oil (2.0653 g, 44% (3 steps)). $^1$H-NMR (CDCl$_3$) δ 1.42 (s, 18H), 1.74 (m, 2H), 2.72 (t, 2H), 3.40 (s, 4H), 3.60 (t, 2H), 6.68 (s, 2H). MS (DCI) 383 (MH)$^+$, 327 (MH-C$_4$H$_9$)$^+$.

EXAMPLE 38

N-Maleoyl-N',N'-bis-(carboxymethyl)propylenediamine·p-toluenesulfonic Acid

A stirred solution of N-maleoyl-N',N'-bis-(t-butoxycarbonylmethyl)-propylenediamine 37 (2.06 g, 5.39 mmol) in methylene chloride (25 mL) at rt was treated with p-toluenesulfonic acid monohydrate (3.07 g, 3 equiv). After 16 h the solvent was removed in vacuo. The residue was triturated with ether four times (each time the ether was decanted off). The resulting semi-sold material was flushed with chloroform (2×150 mL). NMR showed 1.4- 1.5 moles of p-toluenesulfonic acid per mole of product (2.68 g, 97%). $^1$H-NMR (CD$_3$OD) δ 1.96 (m, 2H), 2.29 (s, 4.2H), 3.31 (m, 2H), 3.51 (t, 2H), 4.13 (s, 4H), 6.78 (s, 2H), 7.15 (d, 2.8H), 7.62 (d, 2.8H).

EXAMPLE 39

MPr-IDA-(Phe-Lys(Mtr)-PABOH)$_2$

This was prepared from N-maleoyl-N',N'-bis-(carboxymethyl)propylenediamine-p-toluenesulfonic acid 38 (2.6842 g, 5.25 mmol) and Phe-Lys(Mtr)-PABOH 10a (7.0432 g, 2 equiv) as described above for 26a, except that the crude product was chromatographed on silica, eluting with 1) 2:1 and 2) 1.5:1 methylene chloride/(5:1 ethyl acetate/methanol), to give the product as a white solid (4.5253 g, 55%). $^1$H-NMR (CDCl$_3$/CD$_3$OD) δ 1.24 (m, 4H), 1.41 (m, 4H), 1.52 (m, 2H), 1.83 (m, 2H), 2.06 (brt, 4H), 2.23 (brt, 2H), 2.88 (ABq, 4H), 3.09 (m, 4H), 3.27 (t, 2H), 3.73 (s, 6H), 4.36 (q, 2H), 4.53 (brs, 4H), 4.71 (q, 2H), 6.61 (s, 2H), 6.75 (d, 4H), 7.05–7.48 (m, 42H), 8.74 (brs, 2H). MS (ESI) 1576.4 (MH)$^+$, 1303.6 (M-Mtr)$^+$.

EXAMPLE 40

MPr-IDA-(Phe-Lys(Mtr)-PABC-PNP)$_2$

This was prepared from MPr-IDA-(Phe-Lys(Mtr)-PABOH)$_2$ 39 (1.7993 g, 1.143 mmol) as described above for 27a (1.8909 g, 87%). $^1$H-NMR (CDCl$_3$) δ 1.29 (m, 4H), 1.42 (m, 4H), 1.60 (m, 2H), 1.88 (m, 2H), 2.07 (brt, 4H), 2.32 (brt, 2H), 2.92 (ABq, 4H), 3.08 (m, 4H), 3.29 (t, 2H), 3.72 (s, 6H), 4.35 (q, 2H), 4.66 (q, 2H), 5.20 (s, 4H), 6.63 (s, 2H), 6.75 (d, 4H), 7.05–7.45 (m, 42H), 7.52 (d, 4H), 8.21 (d, 4H), 8.71 (brs, 2H). MS (ESI) 1906.0 (MH)$^+$, 1634.4 (M-Mtr)$^+$. MS (ESI) 1907.8 (MH)$^+$.

EXAMPLE 41

MPr-IDA-(Phe-Lys(Mtr)-PABC-DOX)$_2$

This was prepared from MPr-IDA-(Phe-Lys(Mtr)-PABC-PNP)2 40 (722.7 mg, 0.379 mmol) as described above for 28a. The crude product was chromatographed on silica, eluting with 1) 20:1 and 2) 15:1 methylene chloride/methanol, to give the product as an orange solid (869.4 mg, 84%). $^1$H-NMR (CDCl$_3$/CD$_3$OD) δ 1.16 (d, 10H), 1.42 (m, 4H), 1.49 (m, 4H), 1.82 (m, 6H), 2.00, (m, 2H), 2.12 (m, 4H), 2.19 (m, 4H), 2.53 (brt, 2H), 2.89 (brs, 4H), 2.99 (m, 4H), 3.25 (brs, 4H), 3.49 (m, 2H), 3.67 (s, 6H), 3.73 (m, 2H), 3.99 (s, 6H), 4.12 (m, 2H), 4.31 (m, 2H), 4.55 (m, 2H), 4.71 (s, 4H), 4.92 (ABq, 4H), 5.15 (brs, 2H), 5.40 (brs, 2H), 6.55 (s, 2H), 6.69 (d, 4H), 7.00–7.50 (m, 44H), 7.70 (t, 2H), 7.96 (d, 2H), 8.71 (br, 2H). MS (ESI) 2716.8 (MH)$^+$.

EXAMPLE 42

MPr-IDA-(Phe-Lys-PABC-DOX)$_2$.92Cl$_2$CHCO$_2$H

This was prepared from MPr-IDA-(Phe-Lys(Mtr)-PABC-DOX)$_2$ 41 (714.3 mg, 0.263 mmol) as described above for 29a.(645.9 mg, 96%). $^1$H-NMR (DMF-d$_7$) δ 1.23 (d, 6H), 1.54 (m, 6H), 1.73 (m, 6H), 2.02 (m, 2H), 2.26 (ABq, 2H), 2.48 (m, 4H), 3.09 (m, 4H), 3.12 (brs, 4H), 3.29 (m, 6H), 3.91 (m, 2H), 4.10 (s, 6H), 4.32 (q, 2H), 4.56 (m, 2H), 4.80 (s and m, 6H), 5.13 (brs, 2H), 5.41 (brs, 2H), 5.68 (br, 2H), 6.17 (s, 2H), 6.72 (d, 2H), 6.99 (s, 2H), 7.27 (m, 18H), 7.70 (m, 4H), 7.92 (m, 2H), 8.52 (d, 2H), 8.69 (d, 2H), 10.22 (brs, 2H). MS (ESI) 2171.3 (MH)$^+$.

EXAMPLE 43

Di-t-Butyliminodiacate

A stirred mixture of glycine t-butyl ester hydrochloride (5.0811 g, 30.31 mmol) and potassium bicarbonate (6.3730 g, 2.1 equiv) in DMF (40 mL) at 0° C. was treated with t-butyl bromoacetate (4.9 mL, 1 equiv). The ice bath was removed and the mixture was allowed to stir at rt for 14 h. The solvent was removed in vacuo at 300C and the residue was partitioned between ethyl acetate and 50% sat. sodium bicarbonate. The organic phase was washed with water (3×) and brine, dried over sodium sulfate, and concentrated in vacuo. The residue was chromatographed on silica, eluting with 1) 5% and 2) 25% ehtyl acetate/hexane, to give the product as a colorless oil (4.9310 g, 66%). $^1$H-NMR (CDCl$_3$) δ 1.46 (s, 18H), 3.55 (s, 4H). MS (DCl) 246 (MH)$^+$, 190 (MH-C$_4$H$_9$)$^+$.

EXAMPLE 44

N-Maleoyl-N',N'-bis-(t-Butoxycarbonyl-methyl) propionamide

A suspension of 2-maleimidopropionic acid (1.0007 g, 5.916 mmol) in methylene chloride (12 mL) at rt was treated with oxalyl chloride (1.2 mL, 2.1 equiv) and DMF (1 drop). After 4 h the solvents were evaporated. The residue was flushed with dry methylene chloride (2×20 mL) and dissolved in methylene chloride (2 mL). To this was added a solution of di-t-butyliminodiacetate 43 (1.4510 g, 1 equiv) and DIEA (1.24 mL, 1.2 equiv) in methylene chloride (6 mL), dropwise over 15 min. After 14 h the mixture was diluted with ethyl acetate and washed with 15% citric acid, water and brine. The organic phase was dried over sodium sulfate and concentrated in vacuo to give a pale-yellow glass which was pure enough by NMR to carry to the next step (2.3448 g, 100%). $^1$H-NMR (CDCl$_3$) δ 1.43 (s, 9H), 1.46 (s, 9H), 2.64 (t, 2H), 3.88 (t, 2H), 3.97 (s, 2H), 4.04 (s, 2H), 6.69 (s, 2H). MS (DCl) 397 (MH)$^+$, 341 (MH-C$_4$H$_9$)$^+$.

EXAMPLE 45

N-Maleoyl-N',N'-bis-(Carboxymethyl)-propionamide

A stirred mixture of N-maleoyl-N',N'-bis-(t-butoxycarbonylmethyl)propionamide 44 (1.9100 g, 4.82 mmol) in methylene chloride (40 mL) at rt was treated with trifluoroacetic acid (20 mL). The mixture was sonicated at rt for 20 min and then left to stand for 3.5 h. The reaction was concentrated in vacuo and the residue flushed with chloroform (2×50 mL) and then triturated with ether. The resulting pale-yellow solid was collected by filtration and washed with ether (1.2273 g, 90%). $^1$H-NMR (CD$_3$OD/CDCl$_3$) δ 2.61 (t, 2H), 3.69 (t, 2H), 4.02 (s, 2H), 4.13 (s, 2H), 6.71 (s, 2H). MS (FAB$^-$) 283.1 (M-H)$^-$. HRMS Calcd: 285.0723. Found: 285.0712.

EXAMPLE 46

MP-IDA-(Phe-Lys(Mtr)-PABOH)$_2$

This was prepared from N-maleoyl-N',N'-bis-(carboxymethyl)propionamide 45 (142.1 mg, 0.500 mmol) and Phe-Lys(Mtr)-PABOH 10a (671.0 mg, 2 equiv) as described above for 26a, except that the crude product was chromatographed on silica, eluting with 1) 2:1 and 1.5:1 methylene chloride/(5:1 ethyl acetate/methanol), to give the product as a white solid (349.7 mg, 44%). $^1$H-NMR (CDCl$_3$/CD$_3$OD) δ 1.00–1.90 (m, 12H), 2.07 (brt, 4H), 2.27. (brt, 2H), 3.06 (m, 4H), 3.32–3.82 (m, 6H), 3.70 (s, 6H), 4.26 (m, 1H), 4.35 (m, 2H), 4.52 (d, 4H), 4.62 (m, 1H), 6.51 (s, 2H), 6.72 (q, 4H), 7.00–7.52 (m, 42H). MS (FAB) 1612.5 (M+Na)$^+$, 1628 (M+K)$^+$.

EXAMPLE 47

MP-IDA-(Phe-Lys(Mtr)-PABC-PNP)$_2$

This was prepared from MP-IDA-(Phe-Lys(Mtr)-PABOH)$_2$ 46 (225.4 mg, 0.142 mmol) as described above for 27a (195.5 mg, 72%). $^1$H-NMR (CDCl$_3$/CD$_3$OD) δ 1.05–1.95 (m, 12H), 2.05 (brt, 4H), 2.33 (m, 2H), 3.08 (m, 4H), 3.55 (t, 2H), 3.70 (s, 6H), 3.60–3.99 (m, 4H), 4.52 (m, 2H), 4.63 (m, 2H), 5.21 (d, 4H), 6.57 (s, 2H), 6.74 (q, 4H), 7.00–7.65 (m, 46H), 8.20 (q, 4H). MS (ESI) 1920.8 (MH)$^+$, 1647.8 (MH-Mtr)$^+$.

EXAMPLE 48

MP-IDA-(Phe-Lys(Mtr)-PABC-DOX)$_2$

This was prepared from MP-IDA-(Phe-Lys(Mtr)-PABC-PNP)$_2$ 47 (195.0 mg, 0.102 mmol) as described above for 28a. The crude product was chromatographed on silica, eluting with 1) 20:1 and 2) 15:1 methylene chloride/methanol, to give the product as an orange solid (117.7 mg, 42%). $^1$H-NMR (CDCl$_3$/CD$_3$OD) δ 1.21 (m and d, 1OH), 1.42 (m, 4H), 1.59 (m, 2H), 1.80 (m, 4H), 2.06 (m, 6H), 3.02 (m, 8H), 3.40–3.90 (m, 6H), 3.69 (s, 6H), 4.00 (s, 6H), 4.07 (m, 2H), 4.29 (m, 2H), 4.48 (m, 4H), 4.72 (s, 4H), 4.90 (m, 4H), 5.19 (brs, 2H), 5.42 (brs, 2H), 6.51 (s, 2H), 6.71 (m, 4H), 6.90–7.55 (m, 44H), 7.70 (t, 2H), 7.92 (m, 2H). MS (ESI) 1365.4 (MH$_2$)$^{+2}$, 2728.8 (MH)$^+$.

EXAMPLE 49

MP-IDA-(Phe-Lys-PABC-DOX)$_2$·2Cl$_2$CHCO$_2$H

This was prepared from MP-IDA-(Phe-Lys(Mtr)-PABC-DOX)$_2$ 48 (91.0 mg, 0.033 mmol) as described above for 29a (76.4 mg, 94%). $^1$H-NMR (CDCl$_3$/CD$_3$OD) δ 1.21 (d, 6H), 1.30–1.1.82 (m, 14H), 2.01 (t, 2H), 2.30 (m, 4H), 2.53 (m, 2H), 3.04 (m, 12H), 3.50 (m, 2H), 3.72 (m, 2H), 3.92 (s, 6H), 4.03 (m, 2H), 4.19 (m, 2H), 4.52 (m, 2H), 4.65 (s, 4H), 4.84 (m, 4H), 5.12 (brs, 2H), 5.37 (brs, 2H), 5.79 (s, 2H), 6.57 (s, 2H), 6.73 (d, 2H), 6.95–7.50 (m, 20H), 7.68 (t, 2H), 7.89 (m, 2H). MS (ESI) 1092.4 (MH$_2$)$^{+2}$, 2185.6 (MH)$^+$.

EXAMPLE 50

Z-βAla

A stirred solution of β-alanine (50.10 g, 0.562 mol) in 2M NaOH (281 mL) at 0° C. was treated with benzyl chloroformate (88 mL, 1.1 equiv), dropwise over 1 h. Stirring was continued for 1.5 h at 0° C., followed by 1.5 h at rt. The resulting mixture was extracted with ether (4×500 mL). The aqueous phase was acidified with 5M HCl (120 mL). The resulting white precipitate was collected by filtration, washed with water and dissolved in methylene chloride. The solution was dried over sodium sulfate and concentrated in vacuo to give a white solid (114.95 g, 92%). $^1$H-NMR (CDCl$_3$) 6 2.61 (t, 2H), 3.48 (q, 2H), 5.12 (s, 2H), 5.29 (br, 1H), 7.37 (s, 5H). MS (DCl) 224 (MH)$^+$.

EXAMPLE 51

Z-βAla-OSu

A mixture of Z-βAla 50 (37.42 g, 0.168 mol) and N-hydroxysuccinimide (19.34 g, 1 equiv) in methylene chloride (700 mL) was stirred at 0° C. and treated with DCC (34.69 g, 1 equiv). The reaction was allowed to warm to rt. After 16 h the DCU was removed by filtration and the filtrate was concentrated in vacuo to give a white foam (53.80 g, 100%). $^1$H-NMR (CDCl$_3$) δ 2.86 (s and m, 6H), 3.60 (q, 2H), 5.12 (s, 2H), 5.41 (m, 1H), 7.37 (m, 5H). MS (DCl) 321 (MH)$^+$.

EXAMPLE 52

Z-βAla-lDA

A stirred solution of iminodiacetic acid (16.84 g, 84.32 mmol) and lithium hydroxide monohydrate (10.62 g, 2 equiv) in water (240 mL) at 0° C. was treated with a solution of Z-βAla-OSu 51 (27.01 g, 0.667 equiv) in DME (130 mL). After 15 min the ice bath was removed and the reaction was stirred at rt for 16 h. The mixture was concentrated to a volume of 200 mL on the rotary evaporator. The resulting suspension was extracted with ethyl acetate (2×250 mL), and then the aqueous phase was acidified to pH 1–2 with 85% phosphoric acid. The mixture was extracted with 10% isopropanollethyl acetate (3×200 mL). The combined organic phases were washed with 2% phosphoric acid and brine, dried over sodium sulfate, and evaporated to give a colorless glass which was flushed with chloroform, giving a foam (21.36 g, 75%). $^1$H-NMR (CD3OD) δ 2.51 (t, 2H), 3.32 (t, 2H), 4.04 (s, 2H), 4.15 (s, 2H), 4.98 (s, 2H), 7.25 (m, 5H). MS (FAB) 339 (MH)$^+$, 361 (M+Na)$^+$, 377 (M+K)$^+$. Anal. Calcd for C$_{15}$H$_{18}$N$_2$O$_7$—H$_2$O: C-50.56, H-5.66, N-7.86. Found: C-50.56, H-5.45, N-8.21.

EXAMPLE 53

Z-βAla-IDA-(OSu)$_2$

This was prepared from Z-βAla-IDA 52 (21.36 g, 63.12 mmol) as described above for 51. The crude product was used without purification. $^1$H-NMR (CDCl$_3$/CD$_3$OD) δ 2.62 (t, 2H), 2.83 (s, BH), 3.53 (m, 2H), 4.56 (s, 4H), 5.08 (s, 2H), 5.58 (brt, 1H), 7.35 (m, 5H). Anal. Calcd for C$_{23}$H$_{24}$N$_4$O$_{11}$·0.5H$_2$O: C-51.02, H-4.65, N-10.35. Found: C-50.83, H-5.13, N-10.75.

EXAMPLE 54

Z-βAla-IDA-(βAla-O-t-Bu)$_2$

A stirred suspension of Z-βAla-IDA-(OSu)2 53 (ca. 63.12 mmol) and β-alanine t-butyl ester hydrochloride (25.80 g, 2.25 equiv) in DME (250 mL) at rt were treated with DIEA (24.7 mL, 2.25 equiv). After 12 h the solvents were evaporated and the residue partitioned between ethyl acetate (400 mL) and 2% phosphoric acid. The organic phase was washed with water and brine, dried over sodium sulfate and evaporated. The residue was chromatographed on silica, eluting with 1) ethyl acetate, 2) 15:1, and 3) 10:1 ethyl acetate/methanol, to give the product as a thick, colorless oil (26.56 g, 71%). $^1$H-NMR (CDCl$_3$) δ 1.41 (s, 18H), 2.46 (m, 6H), 3.49 (m, 6H), 3.88 (s, 2H), 3.97 (s, 2H), 5.09 (s, 2H), 5.56 (brt, 1H), 6.89 (brt, 1H), 7.33 (m, 5H), 8.74 (brt, 1H). MS (FAB) 593 (MH)$^+$, 615 (M+Na)$^+$, 631 (M+K)$^+$. Anal. Calcd for C$_{29}$H$_{44}$N$_4$O$_9$—H$_2$O: C-57.04, H-7.59, N-9.17. Found: C-57.15, H-7.36, N-9.46.

EXAMPLE 55

βAla-IDA-(βAla-O-t-Bu)$_2$

Z-βAla-IDA-(O-t-Bu)$_2$ 54 (16.93 g, 28.56 mmol) in absolute ethanol (100 mL) was degassed by bubbling nitrogen through it for 30 min. Palladized charcoal (10%, 1 g) was carefully added and the mixture was hydrogenated on a Parr apparatus at 50 psi for 16 h. The catalyst was then filtered off on a bed of celite and the filtrate concentrated in vacuo. The residue was flushed with methylene chloride, giving a colorless foam (13.11 g, 100%). $^1$H-NMR (CDCl$_3$) δ 1.47 (s, 18H), 2.45 (q, 6H), 3.01 (t, 2H), 3.51 (m, 4H), 3.91 (s, 2H), 4.04 (s, 2H), 6.98 (brt, 1H), 8.93 (brt, 1H). MS (FAB) 459 (MH)$^+$, 481 (M+Na)$^+$, 497 (M+K)$^+$. Anal. Calcd for C$_{21}$H$_{38}$N$_4$O$_7$·2.5H$_2$O: C-50.09, H-8.61, N-11.12. Found: C-50.17, H-8.61, N-10.51.

EXAMPLE 56

Maleoyl-βAla-IDA-(βAla-O-t-Bu)$_2$

A stirred solution of βAla-IDA-(O-t-Bu)$_2$ 55 (6.20g, 13.5 mmol) in chloroform (100 mL) at rt was treated with maleic anhydride (1.46 g, 1.1 equiv). After 1.5 h the mixture was concentrated in vacuo. The residue was flushed with hexane and carried on without further purification. $^1$H-NMR (CDCl$_3$) δ 1.50 (s, 18H), 2.48 (m, 4H), 2.57 (m, 2H), 3.48

(m, 4H), 3.67 (q, 2H), 3.92 (s, 2H), 4.06 (s, 2H), 6.38 (ABq, 2H), 7.39 (brt, 1H), 7.91 (brt, 1H), 8.22 (brt, 1H). MS (FAB) 459.1 (MH)$^+$, 481.2 (M+Na)$^+$, 497.1 (M+K)$^+$.

EXAMPLE 57

MP-IDA-(βAla-O-t-Bu)$_2$

A solution of maleoyl-βAla-IDA-(βAla-O-t-Bu)$_2$ 56 (7.50 g, 13.5 mmol) in acetonitrile (150 mL) under argon at 0° C. was treated with trimethylsilyl chloride (8.6 mL, 5.02 equiv) followed by triethylamine (9.4 mL, 5.02 equiv). The mixture was heated at reflux for 4 h, cooled to rt, and then stored overnight at −20° C. The resulting solid triethylamine hydrochloride was filtered off and the filtrate concentrated in vacuo. The residue was partitioned between ethyl acetate and water. The aqueous phase was extracted with more ethyl acetate. The combined organic phases were dried over sodium sulfate and evaporated. The residue was chromatographed on silica, eluting with 1) 5%, 2) 7%, and 3) 10% methanol/methylene chloride, to give the product as a pale-yellow gum (4.83 g, 66%). $^1$H-NMR (CDCl$_3$) δ 1.42 (s, 18H), 2.47 (m, 4H), 2.61 (t, 2H), 3.50 (m, 4H), 3.81 (t, 2H), 3.88 (s, 2H), 3.99 (s, 2H), 6.60 (brt, 1H), 6.69 (s, 2H), 8.82 (brt, 1H). MS (FAB) 561.2 (M+Na)$^+$, 577 (M+K)$^+$. Anal. Calcd for C$_{25}$H$_{38}$N$_4$O$_7$-1.5H$_2$O: C-53.09, H-7.30, N-9.91. Found: C-53.13, H-6.98, N-10.05.

EXAMPLE 58

MP-IDA-(βAla)$_2$

A solution of MP-IDA-(βAla-O-t-Bu)$_2$ 57 (3.50 g, 6.50 mmol) in methylene chloride (40 mL) at rt was treated with trifluoroacetic acid (30 mL). The mixture was sonicated for 10 min and then left to stand for 1 h. The solvents were evaporated on the rotovap and the residue flushed with chloroform (3×) and ether (4×). The crude product was carried on without further purification. $^1$H-NMR (CD$_3$OD) δ 2.47 (m, 4H), 2.53 (m, 2H), 3.40 (m, 4H), 3.69 (t, 2H), 3.89 (s, 2H), 4.04 (s, 2H), 6.71 (s, 2H). MS (FAB) 433.0 (M+Li)$^+$. Anal. Calcd for C$_{17}$H$_{22}$N$_4$O$_9$-3H$_2$O: C-42.50, H-5.87, N-11.66. Found: C-42.44, H-5.92, N-11.54.

EXAMPLE 59

MP-IDA-(βAla-OSu)$_2$

A stirred solution of MP-IDA-(βAla)$_2$ 58 (136.0 mg, 0.319 mmol) and NHS (73.5 mg, 2 equiv) in DMF (2 mL) at rt was treated with DCC (265.0 mg, 4.01 equiv). The mixture was stirred at rt for 16 h and then was carried on directly to the next step without isolation of the product.

EXAMPLE 60

MP-IDA-(βAla-Phe-Lys(Mtr)-PABOH)$_2$

The crude reaction mixture containing MP-IDA-(βAla)$_2$ 58 (ca. 0.319 mmol) was diluted with DMF (5 mL) and then treated with Phe-Lys(Mtr)-PABOH 10a (429.1 mg, 2.0 equiv). After stirring at rt for 5 h the solvents were removed under high vacuum and the residue was triturated with ether. The resulting solid was collected by filtration and then chromatographed on silica, eluting with 5% methanol/ethyl acetate to remove impurities, and 10% methanoy/methylene chloride to elute the product (220.1 mg, 40%). $^1$H-NMR (DMSO-d$_6$) δ 1.15–1.75 (m, 12H), 1.92 (m, 4H), 2.21 (m, 4H), 2.41 (t, 2H), 2.72 (m, 2H), 3.01 (m, 2H), 3.13 (m, 4H), 3.58 (m, 2H), 3.67 (s, 6H), 3.78 (d, 2H), 3.90 (brs, 2H), 4.38 (m, 2H), 4.42 (d, 4H), 4.53 (m, 2H), 5.09 (t, 2H), 7.80 (d, 4H), 6.96 (s, 2H), 7.05–7.30 (m, 32H), 7.38 (d, 6H), 7.52 (d, 4H), 8.08 (m, 2H), 8.13 (d, 2H), 9.91 (brs, 2H). MS (FAB) 1754.0 (M+Na)$^+$, 1770.0 (M+K)$^+$.

EXAMPLE 61

MP-IDA-(βAla-Phe-Lys(Mtr)-PABC-PNP)$_2$

A stirred solution of MP-IDA-(βAla-Phe-Lys(Mtr)-PABOH)$_2$ 60 (95 mg, 0.0548 mmol) in 1:1 DMF/methylene chloride (6 mL) at rt was treated with bis-p-nitrophenylcarbonate (100 mg, 6 equiv) and DIEA (0.057 mL, 6.0 equiv). After 16 h the solvents were removed under high vacuum and the residue was triturated with 1:1 methylene chloride/ether until it became a solid. This suspension was stored in the freezer for 1.5 h and then the solid was collected by filtration and washed with ether (105 mg, 95%). $^1$H-NMR (DMSO-d$_6$) δ 1.20–1.75 (m, 12H), 1.93 (m, 4H), 2.21 (m, 4H), 2.41 (m, 2H), 2.71 (t, 2H), 3.01 (d, 2H), 3.14 (m, 4H), 3.56 (m, 2H), 3.67 (s, 6H), 3.78 (brs, 2H), 3.91 (brs, 2H), 4.37 (m, 2H), 4.56 (m, 2H), 5.23 (s, 4H), 6.80 (d, 4H), 6.94 (s, 2H), 7.05–7.50 (m, 38H), 7.56 (d, 4H), 7.64 (d, 4H), 8.09 (m, 2H), 8.18 (d, 2H), 8.30 (d, 4H), 10.08 (brs, 2H). MS (ESI) 2062.8 (MH)$^+$.

EXAMPLE 62

MP-IDA-(βAla-Phe-Lys(Mtr)-PABC-DOX)$_2$

MP-IDA-(βAla-Phe-Lys(Mtr)-PABC-PNP)2 61 (1.445 g, 0.701 mmol) and doxorubicin hydrochloride (1.010 g, 2.48 equiv) in DMF (55 mL) were treated with DIEA (0.31 mL, 2.50 equiv). After 40 h at rt the solvent was evaporated under high vacuum and the residue was triturated with 1:1 methylene chloride/ether. The resulting suspension was sonicated briefly and then the solid was collected by filtration and washed with ether. The solid was dissolved as far as possible in 10% methanol/chloroform (100 mL). The mixture was filtered and the filtrate was concentrated on the rotovap to ca. 50 mL. Chloroform (50 mL) was added and the procedure was repeated two more times. The resulting solid was collected by filtration and washed with chloroform and then ether (1.22 g, 61%). $^1$H-NMR (DMSO-d$_6$) δ 1.13 (d, 6H), 1.20–1.75 (m, 12H), 1.81 (m, 2H), 1.92 (m, 4H), 2.19 (m, 6H), 2.30 (m, 2H), 2.72 (m, 2H), 2.98 (m, 6H), 3.12 (m, 2H), 3.45 (m, 2H), 3.56 (t, 2H), 3.69 (s, 6H), 3.73 (m, 2H), 3.89 (m, 2H), 3.96 (s, 6H), 4.14 (m, 2H), 4.33 (m, 2H), 4.57 (d and m, 6H), 4.70 (d, 2H), 4.84 (t, 2H), 4.91 (m, 4H), 5.22 (brs, 2H), 5.46 (s, 2H), 6.79 (d, 4H), 6.93 (s, 2H), 7.05–7.30 (m, 32H), 7.33 (d, 6H), 7.52 (d, 4H), 7.60 (m, 2H), 7.88 (d, 2H), 8.06 (m, 2H), 8.13 (d, 2H), 9.96 (brs, 2). MS (ESI) 2872.6 (MH)$^+$.

EXAMPLE 63

MP-IDA-(βAla-Phe-Lys-PABC-DOX)$_2$·2Cl$_2$CHCO$_2$H

A stirred suspension of MP-IDA-(βAla-Phe-Lys(Mtr)-PABC-DOX)$_2$ 62 (132 mg, 0.0459 mmol) in methylene chloride (8 mL) was treated with anisole (1 mL, 200 equiv) and dichloroacetic acid (0.076 mL, 20 equiv). The mixture immediately became homogeneous. After 5 min an orange precipitate began to form. After 2 h ethyl acetate (25 mL) was added and the suspension stirred for 30 min. The solid was collected by filtration and washed with ethyl acetate and then ether (89 mg, 80%). $^1$H-NMR (DMSO-d$_6$) δ 1.12 (d, 6H), 1.22–1.90 (14H), 2.20 (m, 8H), 2.74 (m, 6H), 2.97 (m, 6H), 3.15 (m, 2H), 3.43 (brs, 2H), 3.56 (m, 2H), 3.72 (m, 2H), 3.97 (s, 6H), 4.14 (m, 2H), 4.38 (m, 2H), 4.56 (s and m, 6H), 4.70 (m, 2H), 4.89 (m, 4H), 5.21 (brs, 2H), 5.46 (brs, 2H), 6.01 (s, 2H), 6.81 (d, 2H), 6.97 (s, 2H), 7.21 (m, 14H), 7.56 (d, 4H), 7.61 (m, 2H), 7.77 (m, 2H), 7.89 (d, 2H), 8.12 (m, 2H), 10.01 (m, 2H). MS (ESI) 2325.6 (MH)$^+$.

EXAMPLE 64

M-Et-IDA-(Phe-Lys-PABC-DOX=β-Ala-mTEG)$_2$

MTEG-β-Ala Hydrazide (254 mg, 866 umole) was dissolved in 10 ml methanol along with 50 ul TFA. This solution was added to a suspension of M-Et-IDA-(Phe-Lys-PABC-DOX)$_2$ (276 mg, 108 umole) in 40 ml anhydrous methanol. The reaction was stirred for 3.5 hr. at room temperature. The reaction mixture was rotary evaporated to the point of precipitation, then 1 ml CH$_2$Cl$_2$ was added to redissolve. This was added dropwise to 250 ml ether, precipitating a red solid. The solid was filtered, washed with ether, and dried under high vacuum to yield M-Et-IDA-(Phe-Lys-PABC-DOX=β-Ala-mTEG)$_2$ (300 mg, 90%). $^1$H-NMR (d$^7$-DMF): (selected peaks) δ 1.23 (d, 6H), 2.34 (t, 4H), 3.28 (s, 6H), 3.55 (s, 24H), 4.03 (s, 6H), 4.10 (t, 4H), 6.98 (s, 2H). Mass Spec.: FAB 1354.6 (M+2H)$^{2+}$ Elemental Analysis for C$_{132}$H$_{164}$N$_{18}$O$_{44}$·4.0H$_2$O·3.0TFA: Theoretical C, 53.11; H, 5.65; N, 8.08. Found C, 52.99; H, 5.96; N, 8.64. FTIR: 3412, 2938, 1702, 1681, 1616, 1520, 1412, 832, 696 cm$^{-1}$.

EXAMPLE 65

M-Et-IDA-(Phe-Lys-PABC-DOX=β-Ala)$_2$

β-Ala Hydrazide triflouroacetate-(578 mg, 1.75 mmole) was dissolved in 10 ml methanol along with 50 ul TFA. This solution was added to a suspension of M-Et-IDA-(Phe-Lys-PABC-DOX)$_2$ (111 mg, 43.6 umole) in 15 ml anhydrous methanol. The reaction was stirred for 1.5 hr. at room temperature. The reaction mixture was rotary evaporated to a volume of 3 ml, then added dropwise to 200 ml acetonitrile, precipitating a red solid. The solid was filtered, washed with acetonitrile, and dried under high vacuum to yield M-Et-IDA-(Phe-Lys-PABC-DOX=β-Ala)$_2$ (117 mg, 99%). $^1$H-NMR (d$^6$-DMSO): (selected peaks) δ 1.13 (d, 6H), 3.95 (s, 6H), 6.96 (s, 2H).

EXAMPLE 66

N-t-Butoxycarbonyl-3-aminopropanol

A solution of 3-aminopropanol (15 mL, 0.20 mol) in methylene chloride (50 mL) at rt was treated with t-butylpyrocarbonate (42.02 g, 1 equiv) in methylene chloride (25 mL), dropwise over 2 h. After stirring overnight the mixture was evaporated, flushed with heptane (3×), and dried in vacuo to give the product as a thick oil (34.31 g, 100%). $^1$H NMR δ 1.48 (s, 9H), 3.12 (br, 1H), 3.22 (q, J=7.5 Hz, 2H), 3.60 (q, J=7.8 Hz, 2H), 4.81 (br, 1H). MS (DCl) 176 (MH)$^+$. Anal calcd for C$_8$H$_{17}$NO$_3$: C-54.84, H-9.78, N-7.99. Found: C-54.80, H-9.82, N-7.97.

EXAMPLE 67

N-t-Butoxycarbonyl-3-aminopropyl Mesylate

The protected amino alcohol 64 (6.601 g, 37.67 mmol) in methylene chloride (45 mL) at 0° C. under argon was treated with methanesulfonyl chloride (2.92 mL, 1.0 equiv) and triethylamine (5.25 mL, 1.0 equiv), dropwise over 30 min. The mixture was stirred for 16 h and then the solvent was evaporated. The residue was partitioned between ether (200 mL) and water (250 mL) and the organic phase was washed with 10% citric acid, water and brine, dried over sodium sulfate and evaporated. The residue was chromatographed on silica, eluting with 2% methanol/methylene chloride. The product was fourld to be unstable over extended periods at rt (5.800 g, 61%). $^1$H NMR δ 1.34 (s, 9H), 1.86 (q, J=7.2 Hz, 2H), 2.95 (s, 3H), 3.19 (m, 2H), 4.12 (t, J=8.0 Hz, 2H), 4.79 (br, 1H).

EXAMPLE 68

Diethyl 2-(N-t-Butoxycarbonylaminopropyl)-malonate

Sodium hydride (60% in mineral oil, 01.84 g, 46 mmol) suspended in THF (20 mL) at 0° C. under argon was carefully treated with diethyl malonate (7 mL, 1.0 equiv) and the mixture was allowed to warm to rt. When it became homogeneous the mesylate 65 (5.84 g, 0.5 equiv) in THF (15 mL) was added all at once. The mixture was heated at reflux overnight, diluted with 1:1 hexane/ethyl acetate and washed with water and brine, dried over sodium sulfate and evaporated. The residue was chromatographed on silica, eluting with 25–35% EtOAc/hexane (5.751 g, 79%) $^1$H NMR δ 1.18 (t, J=7.9 Hz, 6H), 1.35 (s, 9H), 1.81 (m, 2H), 3.04 (q, J=7.4 Hz, 2H), 3.24 (t, J=6.2 Hz, 1H), 4.10 (q, J=7.9 Hz, 4H), 4.62 (br, 1H). MS (FAB) 318 (MH)$^+$, 262 (M—C$_4$H$_9$), 218 (M—C$_5$H$_9$O$_2$). Anal calcd for C$_{15}$H$_{27}$NO$_6$: C-56.77, H-8.57, N-4.41. Found: C-56.65, H-8.45, N-4.42.

EXAMPLE 69

N-t-Butoxycarbonyl-5-amino-2-hydroxymethylpentanol

The diester 66 (4.957 g, 15.62 mmol) in ether (100 mL) under argon at 0° C. was treated with lithium borohydride (2M in THF, 24 mL, 3 equiv) and then with methanol (1.9 mL, 3 equiv). The mixture was heated at reflux for 2.5 h and then carefully quenched with methanol (25 mL) followed by acetic acid (2.7 mL, 3 equiv) upon cooling to rt. The mixture was evaporated and flushed with methylene chloride (2×). The residue was dissolved in methanol (100 mL) and the mixture heated at reflux overnight and then evaporated. The resulting oil was dissolved as far as possible in chloroform (100 mL) with sonication and then the solid inorganics were removed by filtration. The filtrate was evaporated and the residue chromatographed on silica, eluting with 9% methanol/methylene chloride, to give the product as a thick oil (2.770 g, 76%) $^1$H NMR δ 1.21 and 1.41 (m, each 2H), 1.37 (s, 9H), 1.60 (m, 1H), 2.98 (q, J=7.4 Hz, 2H), 3.68 (m, 4H), 3.96 (br, 1H), 4.97 (brt, 1H). MS (DCl) 234 (MH)$^+$, 178 (M—C$_4$H$_9$)$^+$, 134 (M—C$_5$H$_9$O$_2$)$^+$. Anal calcd for C$_{11}$H$_{23}$NO$_4$: C-56.63, H-9.94, N-6.00. Found: C-56.16, H-9.83, N-5.94.

EXAMPLE 70

5-Amino-2-Hydroxymethylpentanol·CF$_3$CO$_2$H

A solution of 5% water in 50% TFAlmethylene chloride (4 mL) was added to the diol 67 (0.145 g, 0.621 mmol) and the mixture was stirred for 1 h. The solvents were evaporated and the residue flushed with methylene chloride (2×) (0.153 g, 100%). $^1$H NMR δ 1.22 and 1.50 (m, each 2H), 1.69 (m, 1H), 2.82 (br, 2H), 3.51 (d, J=6.9 Hz, 4H), 7.78 (br, 3H). MS (DCl) 134 (MH)$^+$.

EXAMPLE 71

5-Maleimido-2-Hydroxymethylpentanol

The aminodiol 68 in dry acetonitrile under argon at 0° C. is treated with maleic anhydride (1 equiv) and DIEA (1 equiv). The mixture is allowed to stir at rt for 4 h. The reaction is re-cooled to 0° C. and treated with trimethylsilyl chloride (3 equiv) and DIEA (3 equiv). The mixture is heated at reflux for 4 h and then, after cooling to rt, is evaporated. The residue is partitioned between ethyl acetate and water. The organic phase is washed with 10% citric acid, water and brine, dried over sodium sulfate and evaporated. The residue is chromatographed on silica gel to give the product.

EXAMPLE 72

5-Maleimido-2-Hydroxymethylpentanol bis-chlorotormate

A solution of the diol 69 in dry methylene chloride is added dropwise to a vigorously stirred solution of 1 M phosgene in toluene (20 equiv) at 0° C. After addition is complete the mixture is stirred at rt for 16 h and then the solvents are removed on the rotary evaporator. The residue is flushed with dry methylene chloride and dried in vacuo. The crude bis-chloroformate is used without further purification.

EXAMPLE 73

MPr-BHP-(Phe-Lys(MMT)-PABOH)$_2$

To a stirred solution of the crude bis-chloroformate 70 in dry methylene chloride at 0° C. is added a solution of Phe-Lys(MMT)-PABOH 10a (2 equiv) and DIEA (2 equiv) in methylene chloride all at once. The mixture is allowed to stir at rt for 16 h and then the solvent is evaporated. The residue is partitioned between ethyl acetate and water. The organic phase is washed with brine, dried over sodium sulfate and evaporated. The product is purified by column chromatography using silica gel.

EXAMPLE 74

MPr-BHP-(Phe-Lys(MMT)-PABC-PNP)$_2$

A stirred mixture of 71, bis-p-nitrophenylcarbonate (6 equiv) and freshly-activated 4 Å powdered sieves in dry methylene chloride under argon at rt is treated with DIEA (6 equiv). After continued stirring for 16 h the mixture is filtered and the filtrate evaporated. The residue is dried in vacuo for several hours and then dissolved in a minimum volume of methylene chloride. To this is added two-times the volume of ether. The resulting solid is collected by filtration, washed with 2:1 ether/methylene chloride, and dried in vacuo.

EXAMPLE 75

MPr-BHP-(Phe-Lys(MMT)-PABC-DOX)$_2$

A stirred solution of the bis-p-nitrophenylcarbonate 72 and DOX hydrochloride (1.1 equiv) in DMF is treated with DIEA (1.1 equiv). After stirring for 2 d the mixture is diluted with ethyl acetate. The solution is washed with water (4×) and brine, dried over sodium sulfate and evaporated. The residue is chromatographed on silica gel to give the product.

EXAMPLE 76

MPr-BHP-(Phe-Lys-PABC-DOX)$_2$·2Cl$_2$CHCO$_2$H

A stirred solution of 73 in methylene chloride is treated with anisole (100 equiv) and then dichloroacetic acid (10 equiv). After 1.5 h the mixture is diluted with ethyl acetate. The resulting suspension is stirred at rt for 1 h and then the orange solid product is collected by filtration, washed with ethyl acetate and dried in vacuo.

EXAMPLE 77

N-Adpoc-3-hydroxyaminopropane

A stirred solution of 3-hydroxyaminopropane and sodium bicarbonate (1 equiv) in water at rt is treated with 1-(1'-adamantyl)-1-methyl-ethoxycarbonyl chloride (1 equiv). After 6 h the resulting solid product is collected by filtration, washed with water, and lyophilized in vacuo. The crude product is carried on without further purification.

EXAMPLE 78

N-Adpoc-3-methanesulfonyloxyaminopropane

To a stirred solution of the alcohol 75 in methylene chloride at 0° C. is added methanesulfonyl chloride (1.05 equiv) and then triethylamine (1.05 equiv). The mixture is allowed to warm to rt and stirred overnight at rt. The solvents is evaporated and the residue partitioned between ethyl acetate and pH 5 buffer (biphthalate). The organic phase is washed with water and brine, dried over sodium sulfate and evaporated to give the product which is carried on without further purification.

EXAMPLE 79 t-Butyl N-Adpoc-5-amino-2-t-butoxycarbonyl-pentanoate

A stirred suspension of sodium hydride in dry tetrahydrofuran at 0° C. under argon is carefully treated with di-t-butylmalonate (1 equiv). The mixture is gradually allowed to warm to rt. When the mixture is homogeneous it is re-cooled to 0° C. and then treated all at once with a solution of the mesylate 76 (0.8 equiv) in tetrahydrofuran. The mixture is allowed to warm to rt and then is heated at reflux for 16 h. Upon cooling to rt the mixture is diluted with ether and the solution is washed with sat. ammonium chloride, water and brine, dried over sodium sulfate and evaporated. The residue is chromatographed on silica gel-to give the product.

EXAMPLE 80 t-Butyl 5-Amino-2-t-butoxycarbonyl-pentanoate

The Adpoc substrate 77 is dissolved in 5% trifluoroacetic acid/methylene chloride containing anisole (100 equiv). After 30 min the solvents are removed under high vacuum at rt and the residue dried in vacuo for several hours. The crude product is carried on immediately without further purification.

EXAMPLE 81 t-Butyl 5-Maleimido-2-t-butoxycarbonyl-pentanoate 79

The aminodiester 78 in dry acetonitrile under argon at 0° C. is treated with maleic anhydride (1 equiv) and the stirred mixture is allowed to stir at rt for 4 h. The mixture is re-cooled to 0° C. and treated with trimethylsilyl chloride (3 equiv) and DIEA (3 equiv). The mixture is heated at reflux for 4 h and then, after cooling to rt, is evaporated. The residue is partitioned between ethyl acetate and water. The organic phase is washed with 10% citric acid, water and brine, dried over sodium sulfate and evaporated. The residue is chromatographed on silica to give the product.

EXAMPLE 82

2-(3'-Maleimidopropyl)-malonic Acid

The di-t-butyl ester 79 is dissolved in 20% trifluoroacetic acid and the mixture is stirred at rt for 5 h. The solvents are evaporated and the residue flushed with methylene chloride several times. The residue is triturated with ether and the resulting solid product is collected by filtration, washed with ether, and dried in vacuo.

EXAMPLE 83

MPr-Mal-(Phe-Lys(MMT)-PABOH)$_2$

A stirred solution of the diacid 80 in dimethoxyethane at 0° C. is treated with n-hydroxysuccinimide (2.2 equiv) and 0.5 M DCC in methylene chloride (2.2 equiv). The mixture is allowed to warm to rt. After 4 h a solution of Phe-Lys (MMT)-PABOH 10a (2 equiv) in dimethoxyethane is added and the mixture is stirred at rt for 16 h. The mixture is then filtered and the filtrate evaporated. The residue is partitioned between ethyl acetate and water. The organic phase is washed with water and brine, dried over sodium sulfate and evaporated. The product is purified by chromatography on silica gel.

EXAMPLE 84

MPr-Mal-(Phe-Lys(MMT)-PABC-PN P)$_2$

A stirred mixture of 81, bis-p-nitrophenylcarbonate (6 equiv) and freshly activated 4 Å powdered sieves in dry methylene chloride under argon at rt is treated with DIEA (6 equiv). After continued stirring for 16 h the mixture is filtered and the filtrate evaporated. The residue is dried in vacuo for several hours and then dissolved in a minimum volume of methylene chloride. To this is added two-times the volume of ether. The resulting solid is collected by fiftration, washed with 2:1 ether/methylene chloride, and dried in vacuo.

EXAMPLE 85

MPr-Mal-(Phe-Lys(M MT)-PABC-DOX)$_2$

A stirred solution of the bis-p-nitrophenylcarbonate 82 and DOX hydrochloride (1.1 equiv) in DMF is treated with DIEA (1.1 equiv). After stirring for 2 d the mixture is diluted with ethyl acetate. The solution is washed with water (4×) and brine, dried over sodium sulfate and evaporated. The residue is chromatographed on silica gel to give the product.

EXAMPLE 86

MPr-Mal-(Phe-Lys-PABC-DOX)$_2$·2Cl$_2$CHCO$_2$H

A stirred solution of 83 in methylene chloride is treated with anisole (100 equiv) and then dichloroacetic acid (10 equiv). After 1.5 h the mixture is diluted with ethyl acetate. The resulting suspension is stirred at rt for 1 h and then the orange solid product is collected by filtration, washed with ethyl acetate and dried in vacuo.

EXAMPLE 87

N-Carbobenzyloxy-N',N'-bis-(carboxymethyl)-ethylenediamine

The di-t-butyl ester 22 is dissolved in 20% trifluoroacetic acid and the mixture is stirred at rt for 5 h. The solvents are evaporated and the residue flushed with methylene chloride several times. The residue is triturated with ether and the resulting solid product is collected by filtration, washed with ether, and dried in vacuo.

EXAMPLE 88

N-Carbobenzyloxy-N',N'-bis-(2-hydroxyethyl)-ethylenediamine 86

A solution of the bis-carboxylic acid 85 in diglyme at 0° C. is treated with N-hydroxysuccinimide (2.2 equiv) and DCC (2.2 equiv). The mixture is allowed to warm to rt and then stirred for 16 h. The resulting solid is removed by filtration. The filtrate is cooled to 0° C. under an argon atmosphere and then treated with 0.5 M sodium borohydride in diglyme. The mixture is allowed to warm to rt for 16 h and is then poured into ice water. The resulting mixture is extracted with ethyl acetate. The organic phase is washed with water and brine, dried over sodium sulfate and evaporated to give the product which is carried on without further purification.

EXAMPLE 89

Bis-(2-Hydroxyethyl)ethylenediamine Hydrochloride

A solution of diol 86 and conc. HCl (1 equiv) in methanol is degassed by bubbling nitrogen through it for 30 min. To this is added 10% palladized charcoal (5 wt. percent). The resulting mixture is shaken on a Parr apparatus under 50 psi of hydrogen gas for 16 h. The mixture is then filtered and the filtrate evaporated. The residue is flushed several times with chloroform to drive off traces of methanol. The crude product is carried on without further purification.

EXAMPLE 90

Bis-(2-Hydroxyethyl)-2'-maleimidoethylamine

The aminodiol 87 in dry acetonitrile under argon at 0° C. is treated with maleic anhydride (1 equiv) and DIEA (1 equiv). The mixture is allowed to stir at rt for 4 h. The mixture is re-cooled to 0° C. and treated with trimethylsilyl chloride (3 equiv) and DIEA (3 equiv). The reaction is heated at reflux for 4 h and then, after cooling to rt, is evaporated. The residue is partitioned between ethyl acetate and water. The organic phase is washed with 10% citric acid, water and brine, dried over sodium sulfate and evaporated. The residue is chromatographed on silica gel to give the product.

EXAMPLE 91

Bis-(2-Chlorocarbonyloxyethyl)-2'-maleimidoethylamine

A solution of the diol 88 in dry methylene chloride is added dropwise to a vigorously stirred solution of 1 M phosgene in toluene (20 equiv) at 0° C. After addition is complete the mixture is stirred at rt for 16 h and then the solvents are removed on the rotary evaporator. The residue is flushed with dry methylene chloride and dried in vacuo. The crude bis-chloroformate is used without further purification.

EXAMPLE 92

MEt-IBHE-(Phe-Lys(MMT)-PABOH)$_2$

To a stirred solution of the crude bis-chloroformate 89 in dry methylene chloride at 0° C. is added a solution of Phe-Lys(MMT)-PABOH 10a (2 equiv) and DIEA (2 equiv) in methylene chloride all at once. The mixture is allowed to stir at rt for 16 h and then the solvent is evaporated. The residue is partitioned between ethyl acetate and water. The organic phase is washed with brine, dried over sodium sulfate and evaporated. The product is purified by column chromatography using silica gel.

EXAMPLE 93

MEt-IBHE-(Phe-Lys(MMT)-PABC-PNP)$_2$

A stirred mixture of 90, bis-p-nitrophenylcarbonate (6 equiv) and freshly activated 4 Å powdered sieves in dry methylene chloride under argon at rt is treated with DIEA (6 equiv). After continued stirring for 16 h the mixture is filtered and the filtrate evaporated. The residue is dried in vacuo for several hours and then dissolved in a minimum volume of methylene chloride. To this is added two-times the volume of ether. The resulting solid is collected by filtration, washed with 2:1 ether/methylene chloride, and dried in vacuo.

EXAMPLE 94

MEt-IBHE-(Phe-Lys(MMT)-PABC-DOX)$_2$

A stirred solution of the bis-p-nitrophenylcarbonate 91 and DOX hydrochloride (1.1 equiv) in DMF is treated with DIEA (1.1 equiv). After stirring for 2 d the mixture is diluted with ethyl acetate. The solution is washed with water (4×) and brine, dried over sodium sulfate and evaporated. The residue is chromatographed on silica gel to give the product.

EXAMPLE 95

MEt-IBHE-(Phe-Lys-PABC-DOX)$_2$·2Cl$_2$CHCO$_2$H

A stirred solution of 92 in methylene chloride is treated with anisole (100 equiv) and then dichloroacetic acid (10 equiv). After 1.5 h the mixture is diluted with ethyl acetate. The resulting suspension is stirred at rt for 1 h and then the orange solid product is collected by filtration, washed with ethyl acetate and dried in vacuo.

EXAMPLE 96

114 (257 mg, 0.25 mmole) and Doxorubicin HCl (377 mg, 0.65 mmole) are stirred in 25 ml dry methanol for 24 hour. The reaction is concentrated by rotary evaporation to 4 ml, then purified in two equal portions on Sephadex LH-20 (1"×18") with methanol. Fractions containing pure product are pooled, rotary evaporated, and dried under high vacuum to yield 115 (222 mg, 50%).

EXAMPLE 97

Conjugation of BR96 or IgG and Branched Peptide Linker Thiolation

BR96 and IgG were thiolated (reduced) by a variation of previously reported method[1]. In a typical example, 1.27 g BR96 (75 ml at 105.7 uM, 7.93 umole) was de-oxygenated by several cycles of alternating vacuum and Ar atmosphere. This was then treated with 7.4 mM DTT (8.6 ml, 63.6 umole in Ar-bubbled PBS, pH 7.0) and stirred at 37° C. under Ar for 3 hr. Removal of low molecular weight compounds was accomplished by ultrafiltration against PBS, pH 6.0 in an Amicon stirred cell at 4° C. A 400 ml Amicon cell was fitted with an Amicon YM30 filter (molecular weight cut-off 30,000), and charged to 40 psi with Ar. Cell eluant was monitored for thiol content with Ellman's reagent[2] until a baseline reading at 412 nm was obtained. Concentration of protein and thiol groups were determined according to the previously reported method[1]. In this example, 1.10 g reduced BR96 (85 ml at 80.8 uM MAb, 619.1 uM thiol) was obtained, for a yield of 87% and a thiol titer of 7.7 mole thiol groups/mole BR96.

EXAMPLE 98

Conjugation:

The following procedure,[1] for the conjugation of BR96 and M-Et-IDA-(Phe-Lys-PABC-DOX=β-Ala-mTEG)$_2$, is typical of that used for all branched peptide linkers modified with the β-Ala-mTEG hydrazone or β-Ala hydrazone. To reduced BR96 (83 ml, 6.70 umole MAb, 51.6 umole thiol) was added dropwise at 0° C. under Ar a solution of M-Et-IDA-(Phe-Lys-PABC-DOX=β-Ala-mTEG)$_2$ (239 mg, 77.3 umole) in 4.0 ml DMSO. After stirring for 30 min., the reaction was filtered through a 0.22u sterile filter. Conjugate was purified at 4° C. by percolation (approximately 2 ml/min.) through a 1"×24" Bio-Beads column (initially prepared by swelling and packing in methanol, then equilibrated in H$_2$O, and finally PBS, pH 7.4). The purified conjugate was filtered again through a 0.22u sterile filter to yield 95 ml of BR96-S-Et-IDA-(Phe-Lys-PABC-DOX=β-Ala-mTEG)$_2$ (BR96, 76.1 uM; DOX, 1.11 mM; MR, 14.6 mole DOX/mole BR96; yield, 100%). Conjugate was frozen in liquid N2 and stored at −80° C.

For more guidance, see Willner, D., Trail, P. A., Hofstead, S. J., King, H. D., Lasch, Braslawsky, G. R., Greenfield, R. S., Kaneko, T., Firestone, R. A. (1993) (6-Maleimidocaproyl)hydrazone of Doxorubicin: A new derivative for the preparation of immunoconjugates of Doxorubicin. Bioconjugate Chem., 4, 521 and Riddles, P. W., Blakeley, R. L., Zerner, B., (1979) Ellman's reagent: 5,5'-Dithiobis(2-nitrobenzoic acid)-A reexamination. Anal. Biochem., 94, 75.

What is claimed is:

1. A compound of the following formula II:

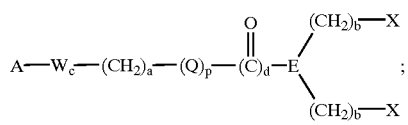

(II)

wherein

A is a thiol acceptor;

W is a bridging moiety;

c is an integer of 0 to 1;

a is an integer of 2 to 12;

Q is O, NH, or N-lower alkyl;

p is an integer of 0 or 1;

d is an integer of 0 or 1;

E is a polyvalent atom;

each b is an integer of 1 to 10;

each X is of the formula

—CO—Y—$Z_m$—$G_n$D wherein

Y is two amino acid residues in the L form;

Z is one or two amino acid residues;

m is an integer of 0 or 1;

G is a self-immolative spacer;

n is a integer of 0 or 1; provided that when n is 0 then —Y—$Z_m$— an amino acid sequence of SEQ ID NO:1 or SEQ ID NO:2; and D is a Drug moiety having a backbone and at least one chemically reactive functional group pendant thereto chemically reacted to the self-immolative spacer or terminal amino acid residue to form a covalent bond, said functional group selected from the group consisting of a primary amine or secondary amine, hydroxyl, sulfhydryl, carboxyl, aldehyde therefore ketone;

or each X is of the formula

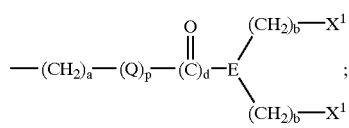

wherein each $X^1$ is of the formula

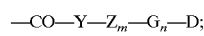

—CO—Y—$Z_m$—$G_n$—D;

wherein Y, Z, G, D, Q, E, m, d, p and n are as defined above;

or each $X^1$ is of the formula

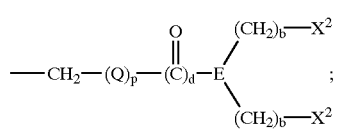

wherein each $X^2$ is of the formula

—CO—Y—$Z_m$—$G_n$—D;

and wherein Y, Z, G, D, Q, E, m, d, p, a, b and n are as defined above;

or each $X^2$ is of the formula

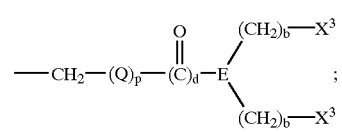

wherein each $X^3$ is of the formula

—CO—Y—$Z_m$—$G_n$—D;

and whereinr Z, G, D, Q, E, m, d, p, a, b and n are as defined above;

or each X3 is of the formula $$-CH_2-(C)_d-N\begin{matrix}(CH_2)_b-X^4\\(CH_2)_b-X^4\end{matrix}$$ with O double-bonded to C;

and wherein each $X^4$ is of the formula

—CO—Y—$Z_m$—$G_n$—D;

and wherein Y, Z, G, D, Q, E, m, d, p, a, b and n are as defined above.

2. The compound of claim 1 wherein each X is of the formula

—CO—Y—$Z_m$—$G_n$—D wherein Y, m, Z, n, and D are as defined above.

3. The compound of claim 1 wherein each $X^1$ is of the formula

—CO—Y—$Z_m$—$G_n$—D wherein Y, m, n, Z, n, and D are as defined above.

4. The compound of claim 1 wherein each $X^2$ is of the formula

CO—Y—$Z_m$—$G_n$—D wherein Y, m, Z, n, and D are as defined above.

5. The compound of claim 1 wherein each $X^3$ is of the formula

—CO—Y—$Z_m$—$G_n$—D wherein Y, m, Z, n, and D are as defined above.

6. The compound of claim 1 wherein —Y—$Z_m$ is a dipeptide, tripeptide or tetrapeptide containing amino acids selected from the group consisting of alanine, valine, leucine, isoleucine, methionine, phenylalanine, tryptophan, proline, lysine, lysine protected with acetyl or formyl, arginine, arginine protected with tosyl or nitro groups, histidine, ornithine, ornithine protected with acetyl or formyl, and citrulline.

7. The compound of claim 1 wherein the —Y—$Z_m$ group is phenylalanine-lysine.

8. The compound of claimn 1 wherein the —$Y_m$—$Z_m$ group is valine-citrulline.

9. The compound of claim 1 wherein the —Y—$Z_m$ group is valine-lysine.

10. The compound of claim 1 wherein E is nitrogen.

11. The compound of claim 1 wherein E is carbon.

12. The compound of claim 1 wherein D is an amino group-containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, N8-acetyl spermidine, 1-(2chloroethyl)-1,2-dimethanesulfonyl hydrazide, tallysomycin, and derivatives thereof.

13. The compound of claim 1 wherein D is doxorubicin.
14. The compound of claim 1 wherein D is mitomycin-C.
15. The compound of claim 1 wherein D is mitomycin-A.
16. The compound of claim 1 wherein D is tallysomycin.
17. The compound of claim 1 wherein D is N-(5,5-diacetoxypentyl)doxorubicin.
18. The compound of claim 1 wherein D is a hydroxyl containing drug moiety selected from the group consisting of etoposide, camptothecin, taxol, esperamicin, 1,8-dihydroxy-bicyclo[7.3.1]trideca-4-ene-2,6-diyne-13-one, anguidine, doxorubicin, morpholine-doxorubicin, N-(5,5-diacetoxypentyl)doxorubicin, vincristine, vinblastine and derivatives thereof.

19. The compound of claim 1 wherein D is a sulfhydryl containing drug moiety selected from the group consisting of esperamicin and 6-mercaptopurine, and derivatives thereof.

20. The compound of claim 1 wherein D is a carboxyl containing drug moiety selected from the group consisting of methotrexate, campothecin (ring-opened form of the lactone), butyric acid, retinoic acid, and derivatives thereof.

21. The compound of claim 1 wherein D is an anthracycline.

22. The compound of claim 1 wherein G is

[structure: p-aminobenzyl with acetate ester]

23. The compound of claim 1 wherein G is p-aminobenzyl-carbonyl.

24. The compound of claim 1 wherein G has the formula

—HN—$R^1$—CO— wherein
$R^1$ is $C_1$–$C_5$ alkyl,
T is O, N or S.

25. The compound of claim 1 wherein G has the formula $$-HN-\overset{T}{C}H-COOR^2$$

wherein
T is O, N or S; and
$R^2$ is H or $C_1$–$C_5$ alkyl.

26. A compound of the following formula III:

$$L-\left[A-W_c-(CH_2)_a-(Q)_p-(C)_d-E\begin{matrix}(CH_2)_b-X\\(CH_2)_b-X\end{matrix}\right]_q$$ (III)

wherein
L is a ligand;
q is an integer of 1 to 10;
A is a thiol acceptor;
W is a bridging moiety;
c is an integer from 0 to 1;
a is an integer of 2 to 12;
Q is O, NH, or N-lower alkyl;
p is an integer of 0 or 1;
d is an integer of 1 or 2;
E is a polyvalent atom;
each b is an integer of 1 to 10;
each X is of the formula

wherein
Y is two amino acid residues in the L form;
Z is one or two amino acid residues;
m is an integer of 0 or 1;
G is a self-immolative spacer; and
n is a integer of 0 or 1; provided that when n is 0 then —Y—$Z_m$— is an amino acid sequence of SEQ ID NO:1 or SEQ ID NO:2;
D is a drug moiety having a backbone and at least one chemically reactive functional group pendant thereto reacted to the self-immolative spacer to form a covalent bond, said funtional group selected from the group consisting of a primary amine secondary amine, hydroxyl, carboxyl, sulfhydryl, aldehyde, therefore ketone;
or X is of the formula

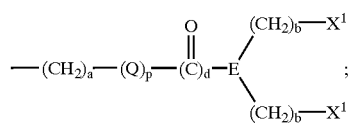

wherein each $X^1$ is of the formula

—CO—Y—$Z_m$—$G_n$—D;

and wherein Y, Z, G, D, Q, E, m, d, p, a, b and n are as defined above;
or each $X^1$ is of the formula

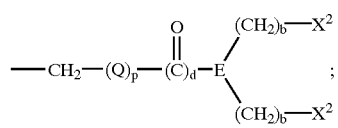

wherein each $X^2$ is of the formula

—CO—Y—$Z_m$—$G_n$—D;

and wherein Y, Z, G, D, Q, E, m, d, p, a, b and n are as defined above;
or each $X^2$ is of the formula

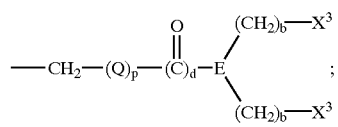

wherein each $X^3$ is of the formula

—CO—Y—$Z_m$—$G_n$—D;

wherein Y, Z, G, D, Q, E, m, d, p, a, b and n are as defined above;
or each $X^3$ is of the formula

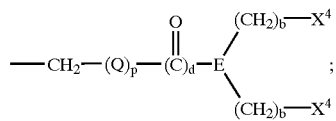

wherein end $X^4$ is of the formula

—CO—$Y_m$—$Z_m$—$G_n$—D;

wherein Y, Z, G, D, Q, E, m, d, p, a, b and n are as defined above.

27. The compound of claim 26 wherein L is an immunoglobulin, or antigen-recognizing fragment thereof.

28. The branched peptide linker of claim 27 covalently bonded to an antibody or antigen-recognizing fragment thereof.

29. The branched peptide linker of claim 26 constantly bonded to drug moieties which are anthracyclines.

30. The compound of claim 26 wherein L is an immunoglobulin selected from the group consisting of BR96, BR64, L6, a relaxed BR96, a relaxed BR64, a chimeric L6, a relaxed chimeric BR96, a relaxed chimeric BR64, a relaxed chimeric L6; and antigen-recognizing fragments thereof.

31. The compound of claim 26 wherein L is a ligand selected from the group consisting of bombesin, EDG, transferrin, gastrin, gastrin-releasing peptide, platelet-derived growth factor, IL-2, Il-6, TFG-α, TFG-β, VGF, insulin, insulin-like growth factors I and II, carbohydrates, lectins, and apoproteins from low density lipoproteins.

32. A pharmaceutical composition comprising a compound of claim 26 and a pharmaceutically acceptable carrier.

33. A method of controlling the growth of cells which comprises administering a compound of claim 26 to a host in need of treatment.

34. The method of claim 33 wherein the cells are cancer cells.

35. A method of cancer treatment of a warm blooded animal in need thereof which comprises administering to said animal an effective tumor inhibiting amount of a compound of claim 26.

* * * * *